United States Patent
De Groot

(10) Patent No.: US 7,321,431 B2
(45) Date of Patent: Jan. 22, 2008

(54) METHOD AND SYSTEM FOR ANALYZING LOW-COHERENCE INTERFEROMETRY SIGNALS FOR INFORMATION ABOUT THIN FILM STRUCTURES

(75) Inventor: Peter De Groot, Middletown, CT (US)

(73) Assignee: Zygo Corporation, Middlefield, CT (US)

(*) Notice: Subject to any disclaimer, the term of this patent is extended or adjusted under 35 U.S.C. 154(b) by 0 days.

(21) Appl. No.: 11/437,002

(22) Filed: May 18, 2006

(65) Prior Publication Data

US 2006/0262321 A1    Nov. 23, 2006

Related U.S. Application Data

(60) Provisional application No. 60/682,742, filed on May 19, 2005.

(51) Int. Cl.
*G01B 11/06* (2006.01)
(52) U.S. Cl. .................. 356/497; 356/504; 356/511
(58) Field of Classification Search ............... 356/479, 356/497, 503, 504, 511–514
See application file for complete search history.

(56) References Cited

U.S. PATENT DOCUMENTS

| | | | |
|---|---|---|---|
| 4,355,903 A | 10/1982 | Sandercock | |
| 4,576,479 A | 3/1986 | Downs | |
| 4,618,262 A | 10/1986 | Maydan et al. | |
| 4,660,980 A | 4/1987 | Takabayashi et al. | |
| 4,818,110 A | 4/1989 | Davidson | |
| 4,999,014 A | 3/1991 | Gold et al. | |
| 5,042,949 A | 8/1991 | Greenberg et al. | |
| 5,042,951 A | 8/1991 | Gold et al. | |
| 5,112,129 A | 5/1992 | Davidson et al. | |
| 5,129,724 A | 7/1992 | Brophy et al. | |
| 5,133,601 A | 7/1992 | Cohen et al. | |
| 5,135,307 A | 8/1992 | de Groot et al. | |

(Continued)

FOREIGN PATENT DOCUMENTS

DE    4108944    9/1992

(Continued)

OTHER PUBLICATIONS

C. Akcay et al., "Spectral shaping to improve the point spread function in optical coherence tomography", *Optics Letters*, vol. 28 No. 20, pp. 1921-1923 (Oct. 15, 2003).

(Continued)

*Primary Examiner*—Samuel A. Turner
(74) *Attorney, Agent, or Firm*—Fish & Richardson P.C.

(57) ABSTRACT

Methods and systems are disclosed for analyzing a scanning interferometry signal. A scanning interferometry signal is provided that is produced by a scanning interferometer for a first location of a test object (e.g., a sample having a thin film). A model function of the scanning interferometry signal is provided which is produced by the scanning interferometer. The model function is parametrized by one or more parameter values. The model function is fit to the scanning interferometry signal for each of a series of shifts in scan position between the model function and the scanning interferometry signal by varying the parameter values. Information is determined about the test object (e.g., a surface height or height profile, and/or a thickness or thickness profile for a thin film in the test object) at the first location based on the fitting.

46 Claims, 32 Drawing Sheets

U.S. PATENT DOCUMENTS

| | | | |
|---|---|---|---|
| 5,301,010 | A | 4/1994 | Jones et al. |
| 5,398,113 | A | 3/1995 | de Groot |
| 5,587,792 | A | 12/1996 | Nishizawa et al. |
| 5,589,938 | A | 12/1996 | Deck |
| 5,602,643 | A | 2/1997 | Barrett |
| 5,774,224 | A | 6/1998 | Kerstens |
| 5,900,633 | A | 5/1999 | Solomon et al. |
| 6,242,739 | B1 | 6/2001 | Cherkassky |
| 6,249,351 | B1 | 6/2001 | de Groot |
| H1972 | H | 7/2001 | Inoue |
| 6,259,521 | B1 | 7/2001 | Miller et al. |
| 6,275,297 | B1* | 8/2001 | Zalicki ..................... 356/504 |
| 6,377,349 | B1 | 4/2002 | Fercher |
| 6,500,591 | B1 | 12/2002 | Adams |
| 6,507,405 | B1 | 1/2003 | Grek et al. |
| 6,545,763 | B1 | 4/2003 | Kim et al. |
| 6,597,460 | B2 | 7/2003 | Groot et al. |
| 6,636,322 | B1 | 10/2003 | Terashita |
| 6,721,094 | B1 | 4/2004 | Sinclair et al. |
| 6,940,604 | B2 | 9/2005 | Jung et al. |
| 7,018,271 | B2* | 3/2006 | Wiswesser et al. ............ 451/8 |
| 2002/0135775 | A1 | 9/2002 | de Groot et al. |
| 2002/0196450 | A1 | 12/2002 | Olszak et al. |
| 2003/0112444 | A1 | 6/2003 | Yang et al. |
| 2004/0085544 | A1 | 5/2004 | de Groot et al. |
| 2004/0185582 | A1* | 9/2004 | Kueny ........................ 438/7 |
| 2004/0189999 | A1 | 9/2004 | de Groot et al. |
| 2005/0057757 | A1 | 3/2005 | de Lega et al. |
| 2005/0068540 | A1 | 3/2005 | de Groot et al. |
| 2005/0073692 | A1 | 4/2005 | de Groot et al. |
| 2005/0078318 | A1 | 4/2005 | de Groot |
| 2005/0078319 | A1 | 4/2005 | de Groot |
| 2005/0088663 | A1 | 4/2005 | de Groot et al. |
| 2005/0146727 | A1 | 7/2005 | Hill |
| 2005/0237534 | A1 | 10/2005 | Deck |
| 2006/0012582 | A1 | 1/2006 | de Lega |

FOREIGN PATENT DOCUMENTS

| | | |
|---|---|---|
| DE | 4309056 | 9/1994 |
| EP | 0 929 094 A2 | 7/1990 |
| EP | 0 397 388 A2 | 11/1990 |
| EP | 0 549 166 A2 | 6/1993 |
| EP | 0 617 255 A1 | 9/1994 |
| GB | 2385417 | 8/2003 |
| WO | WO 97/44633 | 11/1997 |
| WO | WO 02/082008 | 10/2002 |
| WO | WO 03/062802 | 7/2003 |

OTHER PUBLICATIONS

R.M.A. Azzam et al., "Reflection and Transmission of Polarized Light by Stratified Planar Structures", *Ellipsometry and Polarized Light*, Elsevier Science B.V. ISBN 0 444 87016 4 (Paperback) pp. 267-363 (1987).

R.M.A. Azzam et al., "Ellipsometric function of a film-substrate system: Applications to the design of reflection-type optical devices and to ellipsometry", *Journal of the Optical Society of America*, vol. 5, No. 3, pp. 252-260, (1975).

M. Bashkansky et al., "Signal Processing for Improving Field Cross-correlation Function in Optical Coherence Tomography", *Supplement to Optics & Photonics News*, 9(5) (May 1998).

Berman et al., "Review of In Situ & In-line Detection for CMP Applications", *Semiconductor Fabtech—8th Edition*, pp. 267-274, (1998).

A. Bosseboeuf et al., "Application of microscopic interferometry techniques in the MEMS field", *Proceedings of SPIE*, vol. 5145, pp. 1-16 (2003).

M. Davidson et al., "An Application of Interference Microscopy to Integrated Circuit Inspection and metrology", *Proceedings SPIE*, vol. 775, pp. 233-247 (1987).

T. Dresel et al., "Three-dimensional sensing of rough surfaces by coherence radar", *Applied Optics*, vol. 31, No. 7, pp. 919-925 (Mar. 1, 1992).

J.E. Greivenkamp, "Generalized data reduction for heterodyne interferometry", *Optical Engineering.*, vol. 23 No. 4, pp. 350-352 (Jul./Aug. 1984).

P. de Groot et al., "Signal modeling for low coherence height-scanning interference microscopy", *Applied Optics*, vol. 43 No. 25, pp. 4821-4830 (Sep. 1, 2004).

P. de Groot, "Derivation of algorithms for phase-shifting interferometry using the concept of a data sampling window", *Appl. O.pt.*, 34(22), p. 4723-4730 (1995).

P. de Groot et al., "Signal modeling for modern interference microscopes", *SPIE Proceedings*, 5457-4 (2004).

Peter de Groot et al., "Determination of fringe order in white-light interference microscopy", *Appl. Opt.*, 41(22) pp. 4571-4578 (2002).

Feke, Gilbert D. et al., "Interferometric back focal plane microellipsometry", *Applied Optics*, vol. 37, No. 10, pp. 1796-1802 (Apr. 1, 1998).

P.A. Flournoy et al., "White-light interferometric thickness gauge", *Appl. Opt.*, 11(9), pp. 1907-1915 (1972).

G. Hausler et al., "Coherence Radar and Spectral Radar—New Tools for Dermatological Diagnosis", *Journal of Biomedical Optics*, vol. 3, No. 1, pp. 21-31 (Jan. 1998).

R.D. Holmes et al., "Scanning microellipsometry for extraction of true topograpy", *Electronics Letters*, vol. 31, No. 5, pp. 358-359 (Mar. 2, 1995).

Kim, Seung-Woo et al., "Thickness-profile measurement of transparent thin-film layers by white-light scanning interferometry", *Applied Optics*, vol. 38, No. 28, pp. 5968-5973 (Oct. 1, 1999).

Kino, Gordon S. et al., "Mirau correlation microscope", *Applied Optics*, vol. 29, No. 26, pp. 3775-3783 (Sep. 10, 1990).

Kieran G. Larkin, "Efficient nonlinear algorithm for envelope detection in white light interferometry", *Journal of the Optical Society of America A*, vol. 13, No. 4, pp. 832-843 (1996).

Kujawinska, Malgorzata, "Spatial Phase Measurement Methods", *Interferogram Analysis: Digital Fringe Pattern Measurement Techniques*, IOP Publishing Ltd. 1993, pp. 141-193.

Lee et al., "Profilometry with a coherence scanning microscope", *Appl. Opt.*, 29(26), pp. 3784-3788 (1990).

I. Lee-Bennett, "Advances in non-contacting surface metrology", *OF&T Workshop*, paper OTuC1 (2004).

K. Leonhardt et al., "Micro-Ellipso-Height-Profilometry", *Optics Communications*, vol. 80, No. 3, 4, pp. 205-209 (Jan. 1, 1991).

Y. Liu et al., "Common path interferometric microellipsometry", *SPIE*, vol. 2782, pp. 635-645 (1996).

Lyakin et al., "The interferometric system with resolution better than coherence length for determination of geometrical thickness and refractive index of a layer object", *Proceedings of the SPIE—The International Society for Optical Engineering SPIE-INT. Soc. Opt. Eng USA*, vol. 4956, pp. 163-169 (Jul. 2003).

C.J. Morgan, "Least-Squares estimation in phase-measurement interferometry", *Optics Letters*, 7(8), pp. 368-370 (1982).

Ngoi et al., "Phase-shifting interferometry immune to vibration", *Applied Optics*, vol. 40, No. 19, pp. 3211-3214 (2001).

A.V. Oppenheim et al., "10.3: The time-dependent Fourier Transform", *Discrete-Time Signal Processing*, 2nd Edition, pp. 714-722 (Prentice Hall, New Jersey, 1999).

M.C. Park et al., "Direct quadratic polynomial fitting for fringe peak detection of white light scanning interferograms", *Optical Engineering*, vol. 39, No. 4, pp. 952-959 (2000).

S. Pettigrand et al., "Mesures 3D de topographies et de vibrations a l'echelle (sub)micrometrique par microscopie optique interferometrique", *Proc. Club CMOI, Methodes et Techniques Optiques pour l'Industrie*, (2002).

M. Pluta, "Advanced light microscopy", vol. 3, PWN—Polish Scientific Publishers (Elsevier, Amsterdam), pp. 265-271 (1993).

W.H. Press et al., "Linear Correlation", *Numerical Recipes in C*, Cambridge University Press, 2nd Edition, pp. 636-639 (1992).

Rosencwaig, Allan et al., "Beam profile reflectometry: A new technique for dielectric film measurements", *Applied Physics Letters*, vol. 60, No. 11, pp. 1301-1303 (Mar. 16, 1992).

P. Sandoz et al., "Optical implementation of frequency domain analysis for white light interferometry", *Proceedings SPIE*, vol. 2545, pp. 221-228 (Jun. 1995).

P. Sandoz et al., "High-resolution profilometry by using phase calculation algorithms for spectroscopic analysis of white-light interferograms", *Journal of Modern Optics*, vol. 43, No. 4, pp. 701-708 (1996).

Sandoz, Patrick, "Wavelet transform as a processing tool in white-light interferometry", *Optics Letters*, vol. 22, No. 14, pp. 1065-1067 (Jul. 15, 1997).

P. Sandoz et al., "Processing of white light correlograms: simultaneous phase and envelope measurements by wavelet transformation", *SPIE*, vol. 3098, pp. 73-82 (1997).

U. Schnell et al., "Dispersive white-light interferometry for absolute distance measurement with dielectric multilayer systems on the target", *Optics Letters*, vol. 21, No. 7, pp. 528-530 (Apr. 1996).

J. Schwider et al., "Dispersive interferometric profilometer", *Optics Letters*, vol. 19, No. 13, pp. 995-997 (Jul. 1994).

C.W. See et al., "Scanning optical microellipsometer for pure surface profiling", *Applied Optics*, vol. 35, No. 34, pp. 6663-6668 (Dec. 1, 1996).

Shatalin, S.V. et al., "Reflection conoscopy and micro-ellipsometry of isotropic thin film structures", *Journal of Microscopy*, vol. 179, Part 3, pp. 241-252 (Sep. 1995).

M. Totzeck, "Numerical simulation of high-NA quantitative polarization microscopy and corresponding near-fields", *Optik*, vol. 112, No. 9, pp. 399-406 (2001).

R. Tripathi et al., "Spectral shaping for non-Gaussian source spectra in optical coherence tomography", *Optics Letters*, vol. 27, No. 6, pp. 406-408 (Mar. 15, 2002).

D. Willenborg et al., "A novel micro-spot dielectric film thickness measurement system", *SPIE*, vol. 1594, pp. 322-333 (1991).

* cited by examiner

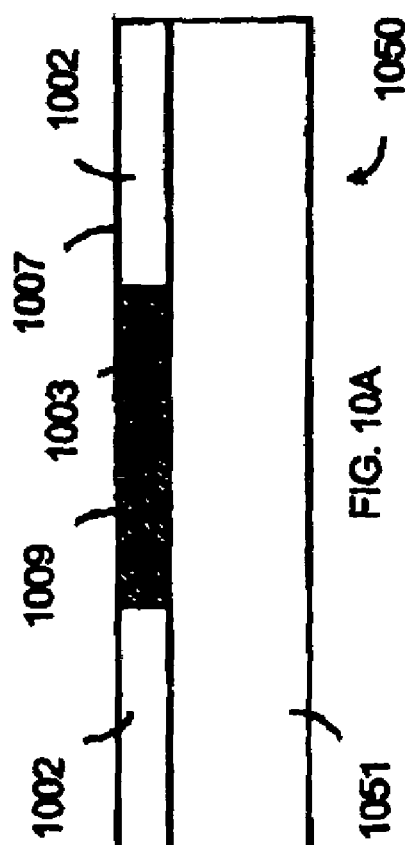
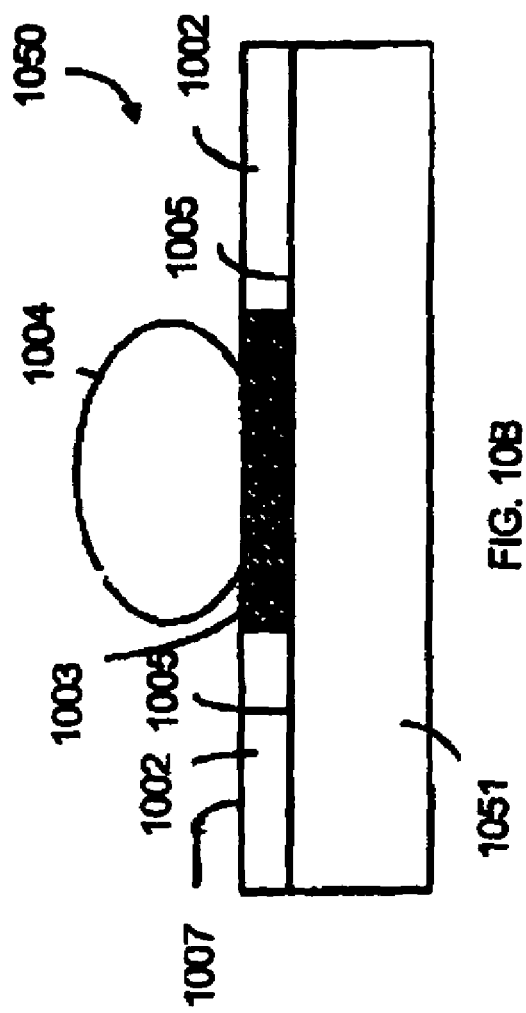

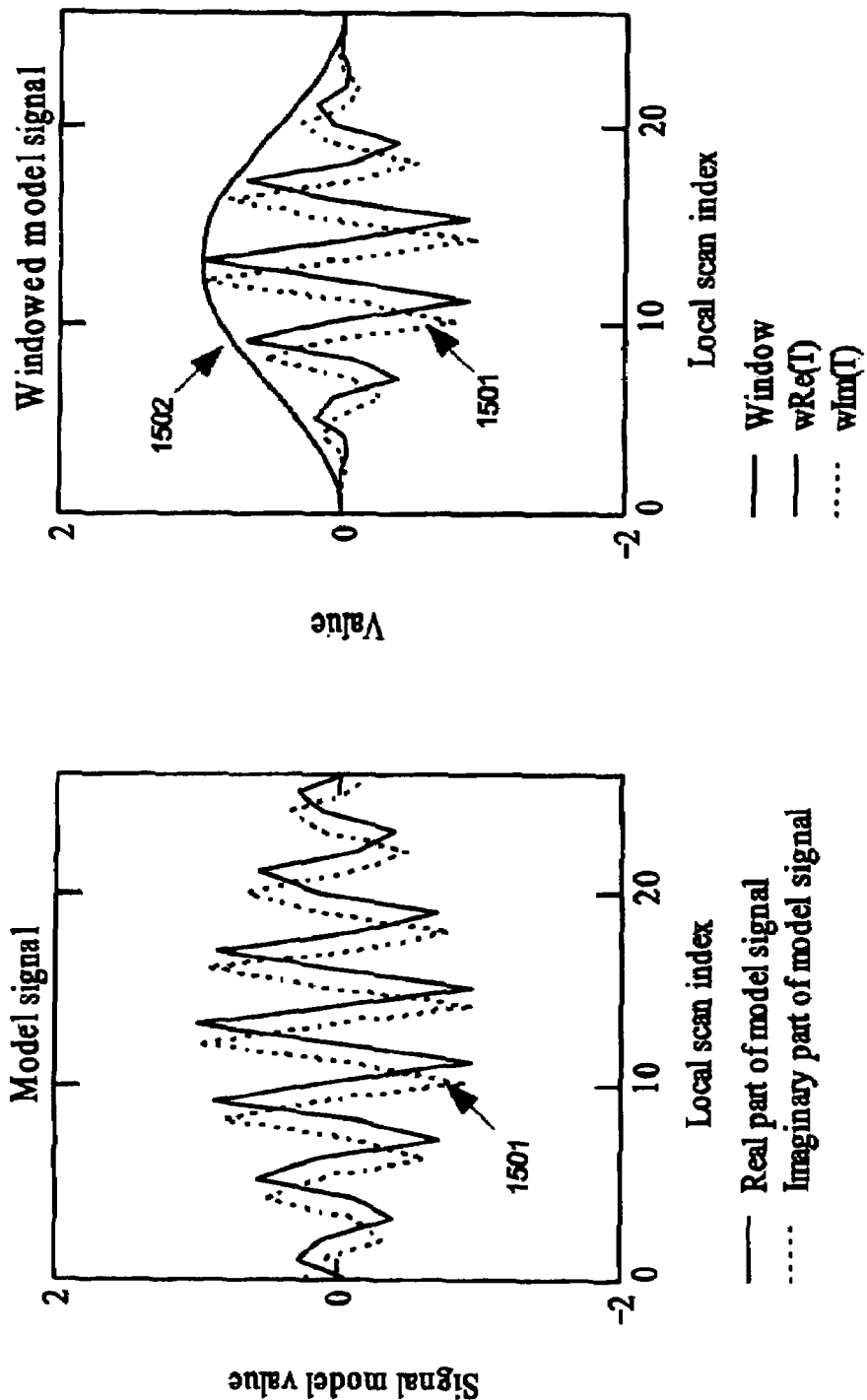

METHOD AND SYSTEM FOR ANALYZING LOW-COHERENCE INTERFEROMETRY SIGNALS FOR INFORMATION ABOUT THIN FILM STRUCTURES

CROSS-REFERENCE TO RELATED APPLICATIONS

Under 35 U.S.C. § 119(e), the present application claims priority to U.S. Provisional Patent Application Ser. No. 60/682,742, filed May 19, 2005 and entitled "METHOD AND SYSTEM FOR ANALYZING LOW-COHERENCE INTERFEROMETRY SIGNALS FOR SURFACE TOPOGRAPHY MEASUREMENT OVER THIN FILM STRUCTURES," the contents of which is incorporated herein by reference.

BACKGROUND

The invention relates to using scanning interferometry to measure surface topography and/or other characteristics of objects having complex surface structures, such as thin film(s), discrete structures of dissimilar materials, or discrete structures that are underresolved by the optical resolution of an interference microscope. Such measurements are relevant to the characterization of flat panel display components, semiconductor wafer metrology, and in-situ thin film and dissimilar materials analysis.

Interferometric techniques ate commonly used to measure the profile of a surface of an object. To do so, an interferometer combines a measurement wavefront reflected from the surface of interest with a reference wavefront reflected from a reference surface to produce an interferogram. Fringes in the interferogram are indicative of spatial variations between the surface of interest and the reference surface.

A scanning interferometer scans the optical path length difference (OPD) between the reference and measurement legs of the interferometer over a range comparable to, or larger than, the coherence length of the interfering wavefronts, to produce a scanning interferometry signal for each camera pixel used to measure the interferogram. A limited (or "low") coherence length can be produced, for example, by using a broadband light source (e.g., a white light source), which is referred to as scanning white light interferometry (SWLI). A typical scanning white light interferometry (SWLI) signal is a few fringes localized near the zero optical path difference (OPD) position. The signal is typically characterized by a sinusoidal carrier modulation (the "fringes") with bell-shaped fringe-contrast envelope. The conventional idea underlying SWLI metrology is to make use of the localization of the fringes to measure surface profiles. Low-coherence interferometry signals can also be produced with narrow band light that illuminates an object over a wide range of angles.

Techniques for processing low-coherence interferometry signals include two principle trends. The first approach is to locate the peak or center of the envelope, assuming that this position corresponds to the zero optical path difference (OPD) of a two-beam interferometer for which one beam reflects from the object surface. The second approach is to transform the signal into the frequency domain and calculate the rate of change of phase with wavelength, assuming that an essentially linear slope is directly proportional to object position. This latter approach is referred to as Frequency Domain Analysis (FDA). In the presence of thin film structures, the analysis can be more complicated.

U.S. patent applications published as US-2005-0078318-A1 entitled "METHODS AND SYSTEMS FOR INTERFEROMETRIC ANALYSIS OF SURFACES AND RELATED APPLICATIONS" and US-2005-0078319-A1 entitled "SURFACE PROFILING USING AN INTERFERENCE PATTERN MATCHING TEMPLATE, both by Peter J. de Groot, disclose additional techniques for analyzing low-coherence interferometry signals from a thin film sample. One of the disclosed techniques identifies the portion of a scanning white light interferometry (SWLI) signal corresponding to the top-surface profile of a thin film structure. For a thin enough film, the individual signals corresponding to the upper and lower interfaces of the film are inseparable, in the sense that the fringe contrast has only one peak; nonetheless, we can argue on physical grounds that the first few fringes on the right most closely relate to the top-surface profile. This technique identifies the trumpet-shaped leading edge of the signal, and ascribes this to the top surface profile. A further technique disclosed in these published applications describes one way of locating the leading edge or other segment of a signal by using a pattern matching technique, one example of which is referred to as correlation template analysis (CTA). Both of said published applications are commonly owned with the present applications and are incorporated herein by reference.

SUMMARY

Preferred embodiments disclosed herein feature a sliding-window least-squares (LSQ) procedure for analyzing low-coherence interferometry signals. The procedure can be used to accurately identify portions of the low-coherence interferometry signals of interest. The procedure performs a fit sequentially through the scan by means of a least-squares optimization. The first step is to create a fitting function based on a model of the signal that we expect to see, then using one or more variable parameters, including an interference phase value, to optimize the fit to the actual signal at each scan position. The scan position for which the LSQ fit is most successful locates the signal, and the phase at this point is the desired final result.

More generally, we now summarize some general aspects, features, and advantages of the invention.

In general, in one aspect, the invention features a method including: providing a scanning interferometry signal produced by a scanning interferometer for a first location of a test object (e.g., a sample having a thin film); providing a model function of the scanning interferometry signal produced by the scanning interferometer, wherein the model function is parametrized by one or more parameter values; fitting the model function to the scanning interferometry signal for each of a series of shifts in scan position between the model function and the scanning interferometry signal by varying the parameter values; and determining information about the test object (e.g., a surface height or height profile, and/or a thickness or thickness profile for a thin film in the test object) at the first location based on the fitting.

Embodiments of the method may further include any of the following features.

The method may further include: providing a scanning interferometry signal produced by the scanning interferometer for each of additional locations of the test object; fitting the model function to each of the scanning interferometry signals corresponding to the additional locations of the test object for each of a series of shifts in scan positions between the model function and the respective scanning interferometry signal by varying the parameter values; and determining information about the test object at the additional locations based on the additional fitting.

For example, the interferometry signal for each location of the test object can be expressed as including an intensity value for each of a series of global scan positions of the scanning interferometer. Furthermore, for example, the model function can be expressed as including an intensity value for each of a series of local scan positions, and wherein the fitting includes fitting the model function to each of the interferometry signals with the model function centered on each of the global scan positions corresponding to the series of shifts in scan position between the model function and the respective scanning interferometry signal by varying the parameter values. Wherein, for each of the locations of the test object, the fitting includes determining which of the series of shifts in scan positions between the model function and the respective scanning interferometry signal produces an optimum fit.

In certain embodiments, for example, the series of global scan positions and the series of local scan positions each correspond to a consecutive series of equal scan increments.

Thereafter, for example, the determining of the information may include determining a surface height profile for the test object based on the shift in scan position corresponding to the optimum fit for each of the locations and/or determining a thickness profile for a thin film in the test object based on the shift in scan position corresponding to the optimum fit for each of the locations.

In some embodiments, the determining which of the series of shifts in scan positions produces the optimum fit includes comparing the model function and the respective interferometry signal to determine the degree of similarity between the model function and the respective interferometry signal. For example, in some embodiments, determining which of the series of shifts in scan positions produces the optimum fit includes determining a shift in scan position for which the corresponding metric indicates a high degree of similarity between the model function and the respective interferometry signal.

In some embodiments, determining which of the series of shifts in scan positions produces the optimum fit includes calculating a metric indicative of the degree of similarity between the model function and the respective interferometry signal. In some embodiments, the metric is additionally based on the magnitude of the model function.

For example, in some embodiments, for each of the locations on the test object, the metric may be related to a sum $$\sum_{z=0}^{N} g(I_z, f_z)$$

where $I_z$ is the intensity value of the interferometer signal at the $z^{th}$ member of the set of global scan positions, $f_z$ is the intensity value of the model function at the $z^{th}$ member of the set of global scan positions, and g is some function which depends on $I_z$ and $f_z$ In further embodiments, for example, the metric is related to the sum of the squares and/or the absolute value of the differences between the intensity value of the model function and the intensity value of the interferometer signal at each of the series of global scan positions.

In some embodiments, the test object includes a thin film. The fitting includes, for each of the locations, determining a first shift of the series of shifts of scan position which corresponds to a first optimal fit and determining a second shift of the series of shifts of scan position which corresponds to a second optimal fit. The determining information includes determining a thickness profile for the thin film based on the first and second shifts in scan position for each of the locations.

In some embodiments, the information about the test object includes a surface height profile for the test object. In some embodiments, the test object includes a thin film, and the information about the test object comprises a thickness profile for the thin film.

In some embodiments, the test object includes a first interface and a second interface. In some embodiments, for example, the first interface is an outer surface of the test object, and the second interface is beneath the test object. In some embodiments, the first and second interfaces are separated by 1000 nm or less.

For each of the locations, the fitting may further include determining an estimate for one or more the parameter values based on the optimum fit. For example, the determining of the information about the test object may be based on the shift in scan position and at least one of the parameter value estimates corresponding to the optimum fit for each of the locations.

The parameter values may include one or more of a phase value, an average magnitude value, and an offset magnitude value. For example, the parameter values may include a phase value, an average magnitude value, and an offset magnitude value.

The fitting may include a least squares optimization.

The model function may be determined theoretically or it may be determined based on empirical data from the scanning interferometer. In either case, in some embodiments, the model function may be a truncated asymmetric function.

The scanning interferometer is typically a low coherence scanning interferometer having a coherence length, and the interferometry signal for the test object typically spans a range larger than the coherence length of the low coherence scanning interferometer.

For each of the locations, the fitting may include determining an estimate for one or more the parameter values based on an optimum fit of the model function to the respective interferometry signal.

The fitting may determine an estimate for an average magnitude parameter value for each of the locations, and the determining of the information about the test object may include determining a fringe-free image of the test object based on the estimates for the average magnitude parameter values. The fitting may further provide surface height information for the test object, and the information about the test object may include the fringe-free image and a surface height profile. Alternatively, or in addition, the fitting may further provide thickness profile information for a thin film in the test object, and the information about the test object may include the fringe-free image and the thickness profile. In some embodiments, the thin film may include a first and second interface separated, for example, by less than 1000 nm.

In some embodiments, the test object includes a first and second interface. For example, the first interface may be an outer surface of the object and the second interface may be beneath the outer surface. In some embodiments, the first and second interfaces may be interfaces of a liquid crystal cell.

In further embodiments, the outer surface is an outer surface of a layer of photoresist overlying a substrate and the second interface is defined between the outer surface of the photoresist and the substrate. In some embodiments, determining a spatial property of the outer surface based on the fitting and modifying a relative position of the object and a photolithography system based on the spatial property.

In further embodiments where the first interface is an outer surface of the object the method may further include, prior to the providing the scanning interferometer signal, removing a material from the outer surface of the object; determining a spatial property of the outer surface of the object based on the fitting; and removing additional material from the outer surface of the object based on the spatial property.

In yet further embodiments where the test object includes a first and second interface, the method may further include, prior to providing the scanning interferometer signal, irradiating the object with a laser to form a scribe line; determining a spatial property of a portion of the object including the scribe line based on the fitting; and performing additional scribing of the same object or a different object based on the spatial property.

In yet further embodiments where the test object includes a first and second interface the method may further include, prior to providing the scanning interferometer signal, forming the first and second interfaces during a solder bump process.

In some embodiments, the method may further include controlling the operation of a semiconductor process tool based on the information determined about the test object at each location. For example, the semiconductor process tool may include one or more of a diffusion tool, rapid thermal anneal tool, a chemical vapor deposition tool (low pressure or high pressure), a dielectric etch tool, a chemical mechanical polisher, a plasma deposition tool, a plasma etch tool, a lithography track tool, and a lithography exposure tool.

In some embodiments, the method may further include controlling a semiconductor process based on the information determined about the test object at each location. For example, the semiconductor process may include one of: trench and isolation, transistor formation, and interlayer dielectric formation (such as dual damascene).

In general, in another aspect, the invention features a system including: a scanning interferometer configured to provide a scanning interferometry signal for each of multiple locations of a test object; and an electronic processor configured to analyze the interferometry signals. The electronic processor is configured to: i) fit a model function of the scanning interferometry signal produced by the scanning interferometer to the scanning interferometry signal corresponding to each of one or more of the locations of the test object, for each of a series of shifts in scan position between the model function and the respective scanning interferometry signal, by varying one or more parameter values parametrizing the model function; and ii) determine information about the test object based on the fit.

Embodiments of the system may further include any of the features described above in connection with the method.

In general, in another aspect, the invention features an apparatus including a computer readable medium storing a program configured to cause a processor to: i) fit a model function of a scanning interferometry signal produced by a scanning interferometer to a scanning interferometry signal corresponding to each of one or more of locations of the test object measured by the scanning interferometer, for each of a series of shifts in scan position between the model function and the respective scanning interferometry signal, by varying one or more parameter values parametrizing the model function; and ii) determine information about the test object based on the fit.

Embodiments of the apparatus may further include any of the features described above in connection with the method.

The techniques disclosed herein may be applicable to any of the following applications: i) simple thin films (e.g., the variable parameter of interest may be the film thickness, the refractive index of the film, the refractive index of the substrate, or some combination thereof); ii) multilayer thin films; iii) sharp edges and surface features that diffract or otherwise generate complex interference effects; iv) unresolved surface roughness; v) unresolved surface features, for example, a sub-wavelength width groove on an otherwise smooth surface; and v) dissimilar materials.

Unless otherwise defined, all technical and scientific terms used herein have the same meaning as commonly understood by one of ordinary skill in the art to which this invention belongs. All patents, patent applications, and references mentioned herein are incorporated herein by reference; in case of conflict, the definitions in the present document control.

Other features, objects, and advantages of the invention will be apparent from the following detailed description.

BRIEF DESCRIPTION OF THE DRAWINGS

FIG. 10a is a schematic diagram of a structure 1050 suitable for use in solder bump processing.

FIG. 10b is a schematic diagram of the structure 1050 from FIG. 10a after solder bump processing has occurred.

FIG. 15a is a plot of the model signal for use in a sliding windows LSQ pattern matching analysis of measurement signal 1201.

FIG. 15b is a plot of the windowed model signal for use in a sliding window LSQ pattern matching analysis of measurement signal 1201.

Like reference numerals in different drawings refer to common elements.

DETAILED DESCRIPTION

In the following, embodiments of a sliding window LSQ pattern matching procedure for analyzing low-coherence interferometry signals are disclosed. An exemplary scanning interferometer system used to acquire an interference signal is described. General pattern matching techniques are discussed. The basic principles of an embodiment of a sliding window LSQ analysis are presented, followed by an example of a sliding window LSQ analysis utilizing discrete sampling. Exemplary applications of the pattern matching procedure are discussed. Finally several simulated and actual experiment examples of embodiments of the pattern matching procedure are presented.

Acquiring the Interference Signal

Figure 1:
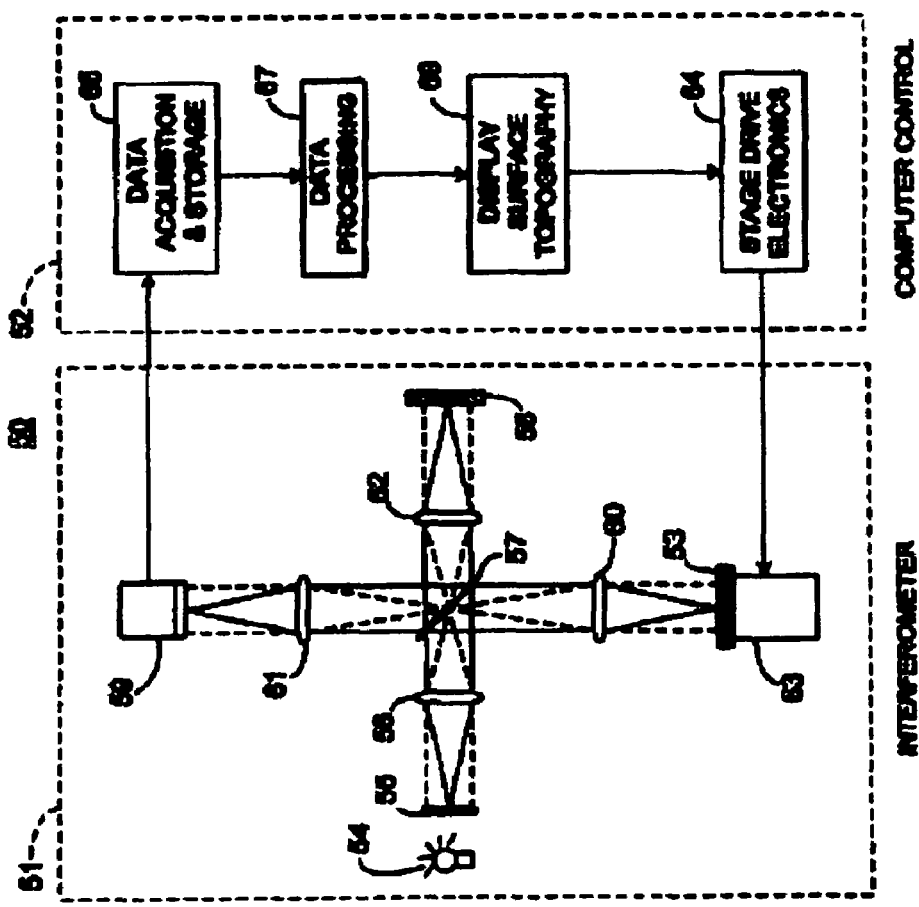
FIG. 1 is a schematic diagram of an interferometry system.

Referring to FIG. 1, an exemplary measurement system 50 for obtaining interference signals includes an interferometer 51 and automated computer control system 52. The measurement system 50 is operable to determine one or more spatial properties of a measurement object 53. In some embodiments, the one or more spatial properties relate to a topography and/or a location of the object 53 with respect to another object, e.g., a portion of system 50. In some embodiments, the other object is a reference portion of a photolithography system. In any event, system 50 is operable to determine one or more spatial properties of objects including one or more at least partially covering layers, e.g., a substrate contacted with a layer of photoresist or solder.

A source 54, which may be a spectrally-broadband source, such as a white-light lamp, or include a plurality of different wavelengths, e.g., resulting from a plurality of light emitting diodes, illuminates a diffusing screen 55. As an alternative or in combination with a broadband source, the source 54 can include a narrow band or quasi-monochromatic source, typically having a high numerical aperture. A low coherence interference signal can be obtained using a monochromatic source in combination with a high numerical aperture, e.g., the coherence length may be on the order of a few microns or less.

Lens 56 transmits a collimated beam to a beam-splitting element 57 that transmits a first portion of the beam to a lens 62 and reference object 58. In some embodiments, reference object 58 is optically flat and includes only a single reflecting surface. For example, reference object 58 can be a reference mirror. In some embodiments, reference object 58 exhibits a three-dimensional surface topography and/or includes more than one spaced-apart layer that reflects light. In the following discussion, it is assumed without limitation that reference object 58 is a reference mirror including a single reflective surface.

Beam-splitting element 57 directs a second portion of the beam to a lens 60, which focuses the beam onto measurement object 53. Beam-splitting element 57 combines light reflected from reference mirror 58 and from measurement object 53. The combined light is directed to a lens 61, which focuses the combined light to a detector 59. Light reflected from measurement object 53 and from mirror 58 interfere at detector 59, which produces detector signals indicative of the resultant beam intensity.

Detector 59 typically includes a plurality of detector elements, e.g., pixels, arranged in at least one and more generally two dimensions. In the following discussion, it is assumed without limitation that detector 59 includes a two-dimensional array of detector elements, such as a CCD includes a plurality of pixels. In the embodiment shown, lens 60 and lens 61 focus light reflected from measurement object 53 onto detector 59 so that each detector element of detector 59 corresponds to a respective point, e.g., a small region or location of measurement object 53. Additionally, lens 62 cooperates with lens 61 to image the reference object 58 onto detector 59. Thus, an interference pattern can be observed at detector 59, even for extended (i.e. spatially incoherent) illumination.

Measurement object 53 can include more than one reflective surface such as a substrate including one or more at least partially optically transmissive layers. A first reflective surface is defined by the interface between the outermost optically transmissive layer and the surrounding atmosphere (or vacuum). Additional reflective surfaces are defined by each interface between layers or between layers and the substrate. In such embodiments, the light reflected from the measurement object 53 can include a contribution, e.g., a separate beam, reflected from each reflective surface or interface. Because each reflective surface or interface is generally spaced apart along the axis of beam propagation, each separate beam generates a different interference pattern when combined with light reflected from the measurement object 53. The interference pattern observed by detector 59 includes the sum of the interference patterns generated by each separate beam reflected from the measurement object.

System 50 is typically configured to create an optical path length difference (OPD) between light directed to and reflected from reference object 58 and light directed to and reflected from measurement object 53. In some embodiments, measurement object 53 can be displaced or actuated by an electromechanical transducer 63, such as a piezoelectric transducer (PZT), and associated drive electronics 64 controlled by computer 52 so as to effect precise scans along a direction that varies the OPD of the interferometer 51. In some embodiments, system 50 is configured to modify the OPD by moving reference object 58. In some embodiments, system 50 is configured to modify the OPD by an amount at least as great as height variations in a topography of the object. In some embodiments, the optical path length is varied by a distance at least as great as a coherence length of the interferometer, e.g., on the order of a few microns.

System 50 can acquire a plurality of detector signals as the OPD is modified, such by scanning a position of measurement object 53. The detector signals thus acquired can be stored in digital format as an array of interference signals, one interference signal acquired from each pixel of detector 59, each interference signal representing the variation in intensity as a function of OPD for a different location of the measurement object 53. For example, if the detector 59 includes a 128.times.128 array of pixels and if 64 images are stored during a scan, then there will be approximately 16,000 interference signals each 64 data points in length. In embodiments using a broadband source 54, the interference signals may be referred to as scanning white light interferometry (SWLI) interference signals, more generally as low coherence length scanning interference signals.

After the data has been acquired, the computer 52 can process 67 the interference signal in accordance with, e.g., pattern matching techniques discussed below, and output data indicative of a surface topography of the measurement object.

The embodiment shown in FIG. 1 schematically shows an interferometer of the Michelson type, in which the beam splitter directs the reference light away from the optical axis of the test light (e.g., the beam splitter can be oriented at 45 degrees to the input light so the test light and reference travel at right angles to one another). In other embodiments, interferometry system 50 can be another type of interferometers. For example, the interferometry system can be include a microscope configured for use with one or more different interference objectives, each providing a different magnification. Each interference objective includes a beam splitter for separating input light into measurement light and reference light.

Examples of different interference objectives include a Michelson-type and Mirau-type interference objective, which includes an objective lens to direct input light towards (and collect light from) the test and reference surfaces, followed by beam splitter to separate the input light into the test and reference light. In the Michelson-type objective, the beam-splitter is oriented at an acute angle to the optical axis defined by the objective lens (e.g., at 45 degrees) to direct the reference light to a side reference mirror. In the Mirau-type object, the beam-splitter is oriented to direct the reference light back along the optical axis to the a small reference mirror in the path of the input light. The reference mirror can be small, and thereby not substantially affect the input light, because of the focusing by the objective lens). In a further embodiment, the interference objective can be of the Linnik-type, in which case the beam splitter is positioned prior to the objective lens for the test surface (with respect to the input light) and directs the test and reference light along different paths. A separate objective lens is used to focus the reference light to the reference lens. In other words, the beam splitter separates the input light into the test and reference light, and separate objective lenses then focus the test and reference light to respective test and reference surfaces. Ideally the two objective lenses are matched to one another so that the test and reference light have similar aberrations and optical paths.

Additional interferometer configurations are also possible. For example, the system can be configured to collect test light that is transmitted through the test sample and then subsequently combined with reference light. For such embodiments, for example, the system can implement a Mach-Zehnder interferometer with dual microscope objectives on each leg.

The light source in the interferometer may be any of: an incandescent source, such as a halogen bulb or metal halide lamp, with or without spectral bandpass filters; a broadband laser diode; a light-emitting diode; a combination of several light sources of the same or different types; an arc lamp; any source in the visible spectral region; any source in the IR spectral region, particularly for viewing rough surfaces & applying phase profiling; and any source in the UV spectral region, particularly for enhanced lateral resolution. For broadband applications, the source preferably has a net spectral bandwidth broader than 5% of the mean wavelength, or more preferably greater than 10%, 20%, 30%, or even 50% of the mean wavelength. For tunable, narrow-band applications, the tuning range is preferably broad (e.g., greater than 50 nm, greater than 100 nm, or greater than even 200 nm, for visible light) to provide reflectivity information over a wide range of wavelengths, whereas the spectral width at any particular setting is preferable narrow, to optimize resolution, for example, as small as 10 nm, 2 nm, or 1 nm. The source may also include one or more diffuser elements to increase the spatial extent of the input light being emitted from the source.

Furthermore, the various translations stages in the system, such as translation stage 150, may be: driven by any of a piezo-electric device, a stepper motor, and a voice coil; implemented opto-mechanically or opto-electronically rather than by pure translation (e.g., by using any of liquid crystals, electro-optic effects, strained fibers, and rotating waveplates) to introduce an optical path length variation; any of a driver with a flexure mount and any driver with a mechanical stage, e.g. roller bearings or air bearings.

Figure 2:
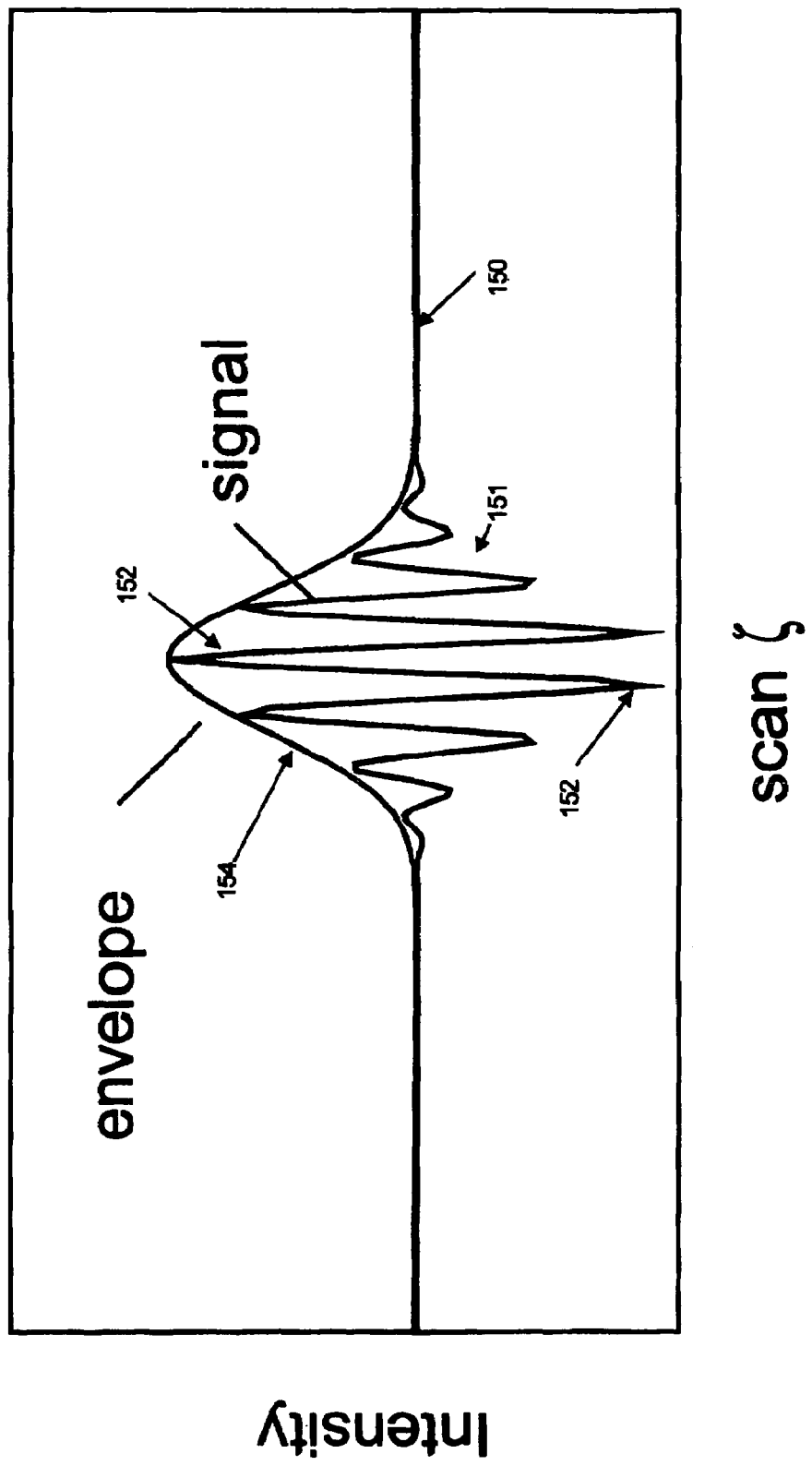
FIG. 2 is a simulated plot of the intensity signal from a typical SWLI system.

The electronic detector can be any type of detector for measuring an optical interference pattern with spatial resolution, such as a multi-element CCD or CMOS detector. Referring to FIG. 2, a simulated low coherence interference signal 150 includes a plurality of detector intensity values obtained from a single point of an object, e.g., a point of a silicon wafer having a single reflective interface. The intensity values are plotted as a function of an optical path length difference (OPD) between light reflected from the object point and light reflected from a reference object. Interference signal 150 is a low coherence scanning white light interferometry (SWLI) signal obtained by scanning the OPD, e.g., by moving an optic and/or the object to vary the optical path traveled by the light reflecting from the object or the reference light. An interferometer may, alternatively or in combination, vary the OPD by detecting a spatial distribution of light reflected from the object and the reference light with the OPD varying as a function of spatial position on a detector.

In FIG. 2, the intensity values are plotted as a function of OPD (here scan position) and map out an interference pattern 151 having a plurality of fringes 152, which decay on either side of a maximum according to a low coherence envelope 154. In the absence of a low coherence envelope, the fringes of an interference pattern typically have similar amplitudes over a wide range of optical path differences. The envelope 154 itself does not expressly appear in such interference signals but is shown for discussion. The location of the interference pattern along the OPD axis is generally related to a position of zero OPD, e.g., a scan position or spatial position corresponding to zero OPD between light reflected from the object point and from a reference object. The zero OPD scan position is a function of the object topography, which describes the relative height of each object point, and the orientation and position of the object itself, which influences the position of each object point with respect to the interferometer. The interference signal also includes instrumental contributions related to, e.g., the interferometer optics, e.g., the numerical aperture (NA) of the optics, the data acquisition rate, the scan speed, the wavelengths of light used to acquire the interference signal, the detector sensitivity as a function of wavelength, and other instrumental properties.

The width of the coherence envelope 154 that modulates the amplitudes of fringes 152 corresponds generally to the coherence length of the detected light. Among the factors that determine the coherence length are temporal coherence phenomena related to, e.g., the spectral bandwidth of the source, and spatial coherence phenomena related to, e.g., the range of angles of incidence of light illuminating the object. Typically, the coherence length decreases as: (a) the spectral bandwidth of the source increases and/or (b) the range of angles of incidence increases. Depending upon the configuration of an interferometer used to acquire the data, one or the other of these coherence phenomena may dominate or they may both contribute substantially to the overall coherence length. The coherence length of an interferometer can be determined by obtaining an interference signal from an object having a single reflecting surface, e.g., not a thin film structure. The coherence length corresponds to the full width half maximum of the envelope modulating the observed interference pattern.

As can be seen from FIG. 2, interference signal 150 results from detecting light having a range of optical path differences that varies by more than the width of the coherence envelope and, therefore, by more than the coherence length of the detected light. In general, a low coherence interference signal can result from obtaining interference fringes that are amplitude modulated by the coherence envelope of the detected light. For example, the interference pattern may be obtained over an OPD for which the amplitude of the observed interference fringes differs by at least 20%, at least 30% or at least 50% relative to one another.

A low coherence interferometer can be configured to detect an interference signal over a range of OPD's that is comparable to or greater than the coherence length of the interferometer. For example, the range of detected OPD's may be at least 2 times greater or at least 3 times greater than the coherence length. In some embodiments, the coherence length of the detected light is on the order of the height variations of features of the object, e.g., on the order of a couple of microns or less but more than a nominal wavelength of the detected light.

In general, instrument related contributions to the interference signal, e.g., to the shape and phase of the interference patterns, tend to vary slowly with the topography and position of the object. On the other hand, interference patterns shift along the scan position axis for interference signals obtained from object points having different spatial properties, e.g., different relative heights or different relative positions with respect to the interferometer. Accordingly, interference patterns obtained from different object points may have similar shapes but are shifted along the scan position axis by an amount related to the spatial properties of each point.

Figure 3:
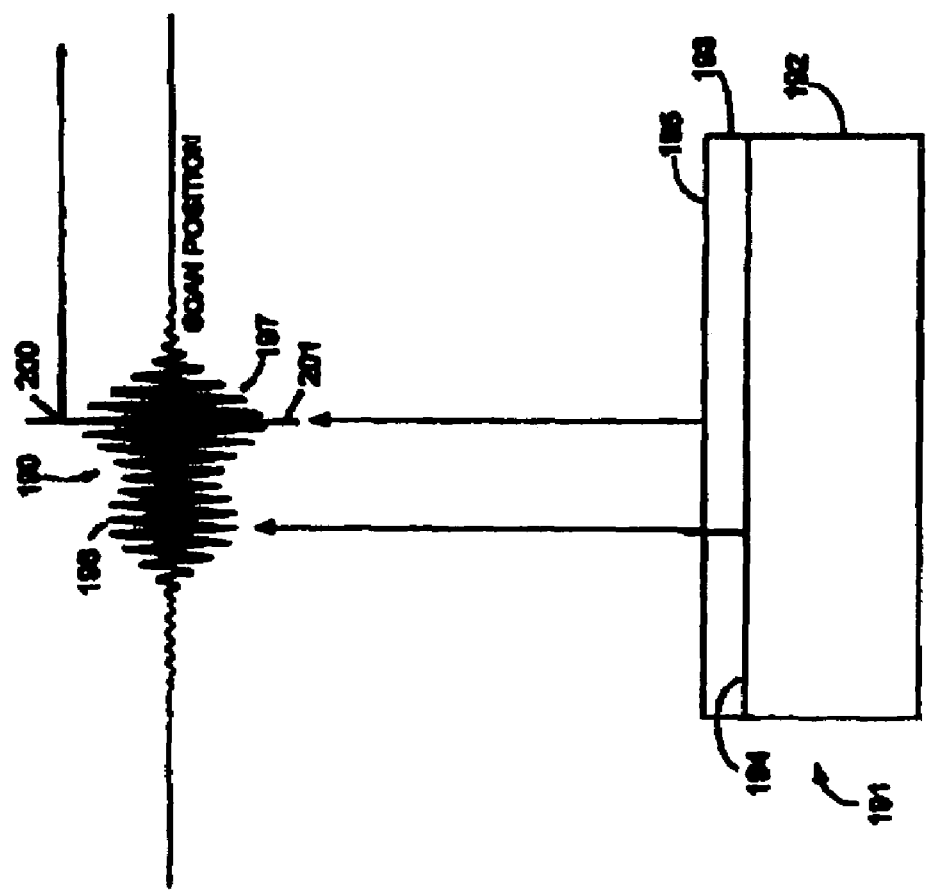
FIG. 3 is a schematic diagram of a measurement object featuring multiple interfaces along with a corresponding SWLI signal.

Referring to FIG. 3, an interference signal 190 is acquired from an object 191, which includes a substrate 192 and an overlying layer, e.g., a thin film 193. The substrate and film define an interface 194 therebetween. An outer surface of the film 195 defines an interface between the object and its surroundings, e.g., the air, other gas, or vacuum. Interfaces are generally defined by a change in refractive index between portions of an object.

Interference signal 190 includes a first interference pattern 196 resulting from interface 194 and a second interference pattern 197 resulting from interface 195. First and second interference patterns 196,197 are overlapping. For example, maxima of the interference patterns 196,197 are separated by an OPD less than the coherence length of the interferometer and patterns 196,197 are not separated by a region of zero intensity. Existing methods for determining spatial properties of an object with interfaces that produce overlapping interference patterns can yield erroneous results because the overlapping interference patterns distort one another.

Figure 4:
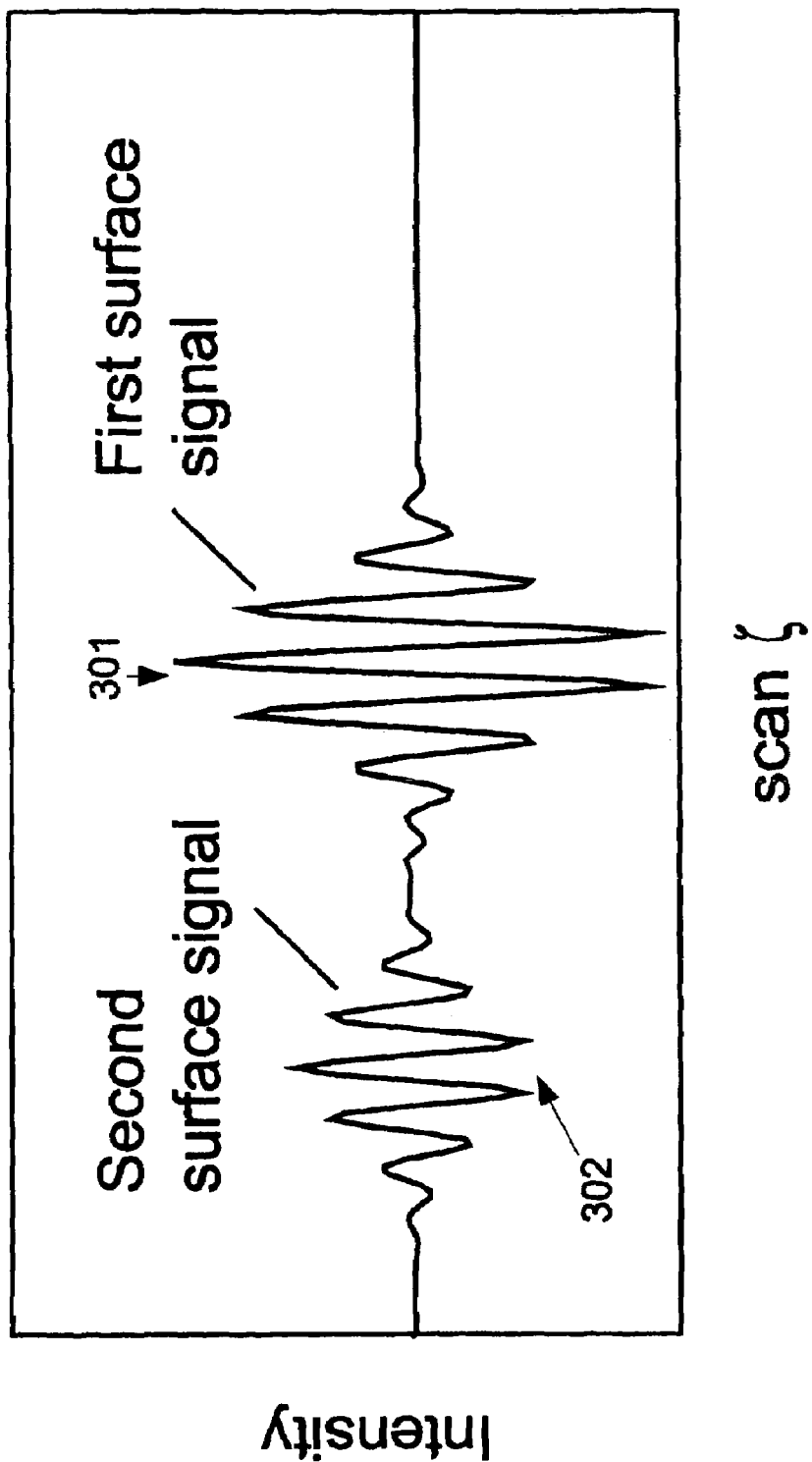
FIG. 4 is a plot of a simulated SWLI signal featuring distinguishable contributions from two interfaces.

Referring to FIG. 4, for thick enough film samples, there are two or more easily identifiable signals 301, 302 corresponding to the interfaces between differing materials in the film stack.

Pattern Matching

One approach to the analysis of the interferometry signals from a thin film sample is the observation that multiple reflections generate multiple signals, which often can be separated from one another. Pattern matching techniques may be employed that operate directly on the interference signals generated by scanning the optical path difference. For complex surface structures of unknown composition and relatively thick films (e.g. >1 micron), this approach is flexible. To the extent that scan-domain pattern matching can be extended to thinner films, this approach generally does not require prior knowledge of the thin film materials.

The idea underlying scan-domain pattern matching is as follows. An experimental signal is generated by varying the OPD using a mechanical scan of the interferometer in the direction of the height coordinate, as shown in FIG. 2. One expects to see interference fringes recorded by as a sinusoidal signal possibly modulated in fringe contrast by coherence effects. Typically SWLI algorithms seek to identify a feature such as the peak of the envelope or the signal centroid, followed by the phase of the underlying fringes for higher resolution.

A pattern matching approach assumes that all pixels in a SWLI data set contain the same basic, localized interference pattern, only rescaled and shifted in position for each pixel, and perhaps duplicated when there are films as shown in FIGS. 3 and 4. One approach to pattern matching is, for example, to model the signal with a simple mathematical function, such as a single-wavelength carrier modulated in contrast by a Gaussian envelope. A simple dot-product correlation can be used to compare this model to the experimentally-acquired data to locate the position of best match.

Correlation template analysis (CTA) goes a step further and generates the correlation kernel empirically from the actual signal from the instrument. As a result, the model signal need not be the usual idealized analytical function such as a gaussian-modulated cosine—it can have any arbitrary envelope or a nonlinear phase component in the carrier fringes. If the test part is, for example, a solid surface, the model signal follows from the experimental data set itself, using a shift-invariant averaging to extract a single interference pattern template representative of the main features of the signal observed repeatedly in all of the pixels. The model signal is therefore well adapted to the instrument, incorporating all specific characteristics of the interferometer, including phase dispersion, mean wavelength, spectral distribution and so on.

CTA may also go beyond the simple dot-product correlation and employs mathematical tools to identify arbitrary features of the signal that may be of greater interest than the peak, centroid or other elementary characteristic of the coherence envelope. For example, in a technique described in U.S. Patent Application Publication US-2005-0078318-A1, the model signal is truncated so that the merit function identifies the leading edge of the signal, rather than its peak.

Figure 5:
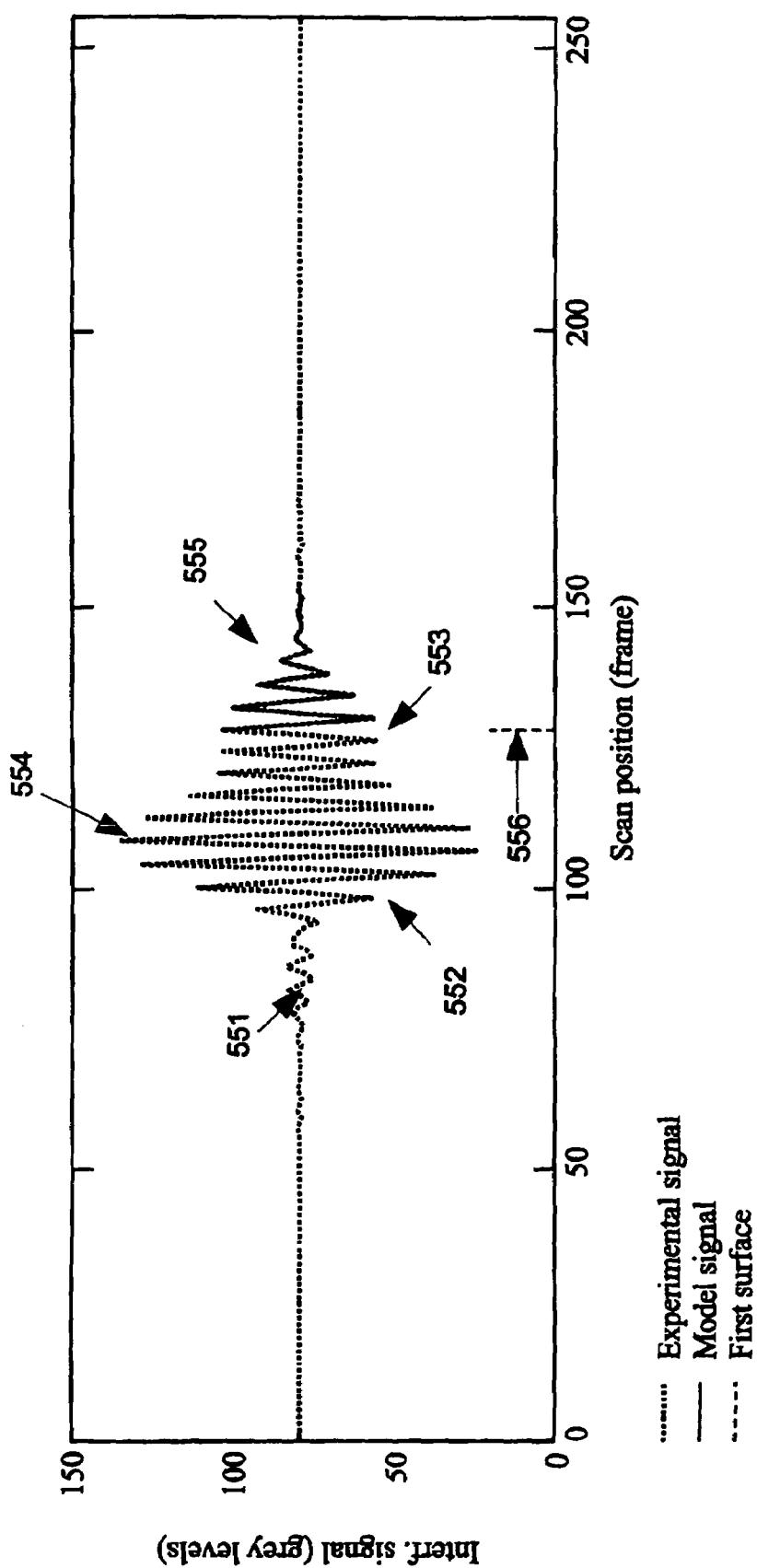
FIG. 5 depicts a truncated model signal fit to a simulated SWLI signal.

Referring to FIG. 5, an illustration of this technique is shown by simulation. An SWLI signal 551 is obtained from a sample object composed of 950 nm of SiO2 on Si. For simplicity, the simulation assumes that the interferometer system has a numerical aperture substantially equal to zero, so that only plane waves need to be considered. The system operates at a central wavelength of 570 nm with a 120 nm bandwidth. The scan is from inside the part to the outside, so greater surface heights are to the right.

As shown in FIG. 5, the interference signal 551 contains two interference patterns 552, 553 because of, for example, a thin film effect as described above. The patterns are inseparable, in the sense that the fringe contrast has only one peak 554; nonetheless, one can argue on physical grounds that the first few fringes on the right most closely relate to the top-surface profile. The truncated model signal 555 therefore includes only the trumpet-shaped right-hand portion of a single-surface signal. This technique, hereinafter referred to as a truncated model technique, uses this truncated model 555 to identify the leading edge 556 by finding the best match position, even though the signal peaks further to the left.

Several other techniques are available for pattern matching. Some CTA techniques use a normalized correlation in the Frequency domain equivalent to the Pearson's product-moment correlation coefficient r familiar from statistics. Relying extensively on Fourier Transforms of large data sets, this frequency-domain can be too slow for some production applications. To speed up the analysis, the Pearson's correlations can be replaced with standard dot products in the time or scan domain, as disclosed in U.S. Patent Application Publication US-2005-0078318-A1, described above. The resulting algorithm is herein referred to as a dot product based technique. With this simplification, the signal location is effectively defined by the peak signal strength within the frequency range defined by the model signal. The dot product based technique retains the idea of a model signal generated directly from the instrument; but in some ways it has lost the ability to effectively implement the truncated model technique. This is a sensible trade off for thicker films found, e.g., on flat panel displays, and where time is at a premium.

In what follows, the applicant discloses yet further techniques to extract accurate information about the test object in the presence of even thinner films. The techniques reintroduces the truncated model technique described above using a significantly more powerful sliding-window least-squares (LSQ) technique that provides better results than Pearson's-r techniques while retaining the speed advantages of dot product based techniques.

Sliding window LSQ: Basic Principle

Figure 6:
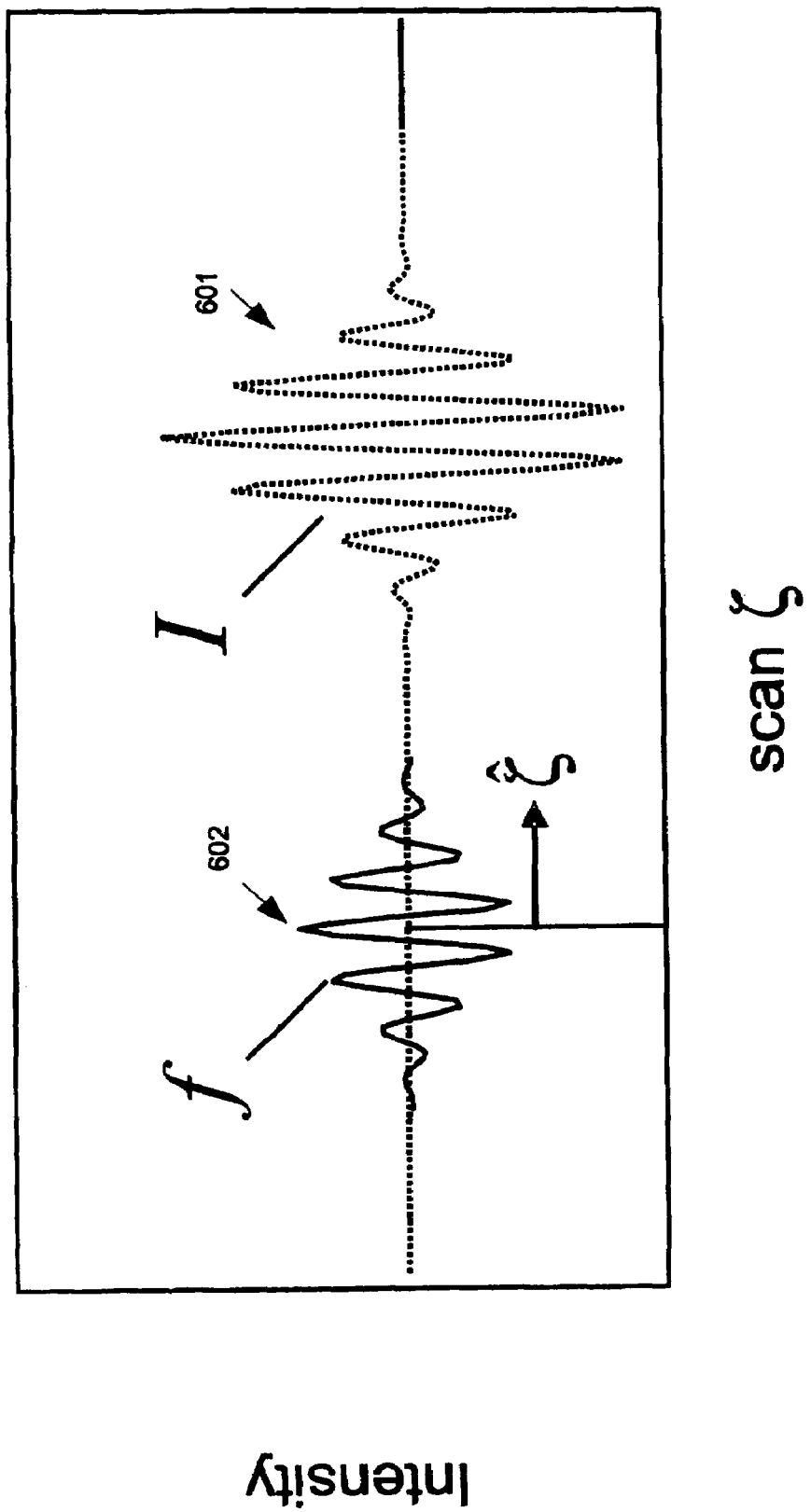
FIG. 6 depicts a model signal used in a sliding window LSQ pattern matching technique and a simulated SWLI signal.

Referring to FIG. 6, an interference signal 601 is recorded for a plurality of interferometer scan positions. The first step is to create a fitting function 602 based on a model of the expected signal which includes one or more variable parameters, e.g., an interference phase value. At a given scan position, the parameters are varied to optimize the fit to the actual signal at each scan position by means of, for example, a least-squares optimization (although other optimizations techniques may be used). Next, the pattern matching technique performs a fit sequentially through the scan by means of a least-squares optimization (although other optimizations techniques may be used). The scan position for which the LSQ fit is most successful locates the signal, and the phase at this point is the desired final result.

A suitable fitting function $f$ comprising a complex, oscillating signal model $\tilde{T}$ with separated offset $m^{dc}$, average magnitude $m$ and local phase $\phi$ at $K^0$:

$$f(y,\xi) = m^{dc}(y) + m(y) Re\{\tilde{T}(\xi) \exp[i\phi(y)]\} \tag{1}$$

For simplicity, a single lateral coordinate y is used to show a dependence on the location within the image, although for full imaging there would of course be two coordinates x, y. As shown in FIG. 6, there is global scan position $\zeta$ for the experimental signal I and a local scan coordinate $\hat{\zeta}$ associated with the fitting function $f$ of Eq.(1). The tilde over $\tilde{T}$ denotes complex quantity, potentially with a nonlinear, scan-dependent phase and magnitude. An illustrative example of a complex signal model with a linear phase passing through zero at $\hat{\zeta}=0$ is $$\tilde{T}(\hat{\zeta}) = C(\hat{\zeta})\exp(-i\hat{\zeta}K^0) \quad (2)$$

where C is the coherence envelope.

Next, the location of this signal is adjusted and ($m^{dc}$, m, $\phi$) are allowed to vary with the scan position $\zeta$, as needed to optimize the fit of $f$ to the signal I:

$$f(y,\zeta,\hat{\zeta}) = m^{dc}(y,\zeta) + m(y,\zeta)Re\{\tilde{T}(\hat{\zeta})\exp[i\phi(y,\zeta)]\}. \quad (3)$$

The sliding window LSQ technique solves for the parameters ($m^{dc}$, m, $\phi$) using by fit optimization within a tapered window w at each of the scan positions $\zeta$. The goal therefore is to minimize the following square difference function at each $\zeta$:

$$\chi^2(y,\zeta) = \int w(\hat{\zeta})[I(y,\zeta+\hat{\zeta}) - f(y,\zeta,\hat{\zeta})]^2 d\hat{\zeta}. \quad (4)$$

The window w places range limits on the local scan $\hat{\zeta}$ and allows us to concentrate on certain features of the signal with few computations. As is known in the art, a tapered window such as a raised cosine is more forgiving of imperfections in the scan $\zeta$ than a simple square window. See, e.g., P. de Groot, "Derivation of phase shift algorithms for interferometry using the concept of a data sampling window," Appl. Opt. 34(22) 4723-4730 (1995), incorporated by reference herein.

The best-fit solution for the signal strength m at each scan position $\zeta$ is expected to rise and fall according to the envelope of the experimental signal I. The scan position that minimizes the square difference $\chi^2$ while the signal strength m is strong locates the signal. We infer the phase $\theta$ at $K^0$ and $\zeta=0$ from the phase value $\phi$ for this best fit position, and hence the high-resolution surface height measurement. The offset $m^{dc}$ is the local DC offset value, useful for generating and analyzing the fringe-free image of the object.

Discrete Sampling

In an actual scanning interferometer instrument, the interference signal is typically recorded by a CCD camera configured to capture multiple images, or camera frames, each at a different scan position. Thus, the interferometer signal intensity I is typically sampled at a total of Y discrete field positions y indexed by the pixel number j=0 ... (Y−1) and discrete scan positions $\zeta$ indexed by the camera frame number z=0 ... (N−1). The scan increment is $\zeta^{step}$ and therefore a scan centered about zero is $$\zeta_z = [z - (N-1)/2]\zeta^{step} \quad (5)$$

The square difference function translates to the discrete equivalent $$\chi^2_{j,z} = \sum_{\hat{z}=0}^{\hat{N}-1} (I_{j,z+\hat{z}-\hat{\Delta}} - f_{j,z,\hat{z}})^2 w_{z,\hat{z}} \quad (6)$$

where $\hat{N}$ is the number of local scan positions within the window w, the fitting function $f$ is $$f_{j,z,\hat{z}} = m_{j,z}^{dc} + m_{j,z}Re[\tilde{T}_{\hat{z}}\exp(i\phi_{j,z})] \quad (7)$$

and $\hat{\Delta}$ is an integer offset that centers the window w with respect to the scan index z, required because many programming languages require vector indices such as z, $\hat{z}$ to start from zero. The window width $\hat{N}$ is established by balancing performance and speed—better robustness and repeatability implies a larger $\hat{N}$, at the cost of more computations. A typical compromise is $\hat{N}=21$ for a data acquisition of four frames per fringe.

For a symmetric fitting function, the offset $\hat{\Delta}$ is $$\hat{\Delta} = round[(\hat{N}-1)/2] \quad (8)$$

and the local scan position is $$\hat{\zeta}_{\hat{z}} = [\hat{z} - (\hat{N}-1)/2]\zeta^{step}. \quad (9)$$

For a truncated LSQ technique, the fitting function may be asymmetric, incorporating only the right half of the model signal:

$$\hat{\Delta} = 0 \quad (10)$$

$$\hat{\zeta}_{\hat{z}} = \hat{z}\zeta^{step}. \quad (11)$$

Other signal segments or derived patterns are possible as needed to isolate specific portions of the experimental signal.

Signal Model

There are (at least) two ways to create the complex model signal $\tilde{T}$: from theory or from experiment.

In some cases, it is sufficient to describe the signal theoretically as a carrier evolving at a frequency $K^0$ modulated by a fringe contrast envelope C, as in Eq.(2). A discretely-sampled complex model signal following this approach is $$\tilde{T}_{\hat{z}} = C_{\hat{z}}\exp[-i\hat{\zeta}_{\hat{z}}K^0]. \quad (12)$$

A negative phase term in Eq.(12) preserves the traditional sign convention, for which an increasing scan corresponds to moving the interference objective away from the part. This is opposite to an increase in surface height, which by definition corresponds to a positive change in phase. Eq.(12) is a reasonable idealized model of the kind of signal that we expect to see in a SWLI system.

A second approach is to use empirical data acquired from the instrument itself, in which case we use an inverse Discrete Fourier Transform (DFT) based on the frequency-domain representation $\tilde{q}^{sys}$ of a typical signal:

$$\tilde{T}_{\hat{z}} = \sum_{v=vmin}^{vmax} \overline{\tilde{q}_v^{sys}}\exp[-i\hat{\zeta}_{\hat{z}}K_v]. \quad (13)$$

The $\overline{\tilde{q}}^{sys}$ is the average over many pixels of data of the frequency-domain representation of a typical interference signal for the instrument. Note that this model signal may have a complicated envelope and nonlinear phase, depending on the actual instrument characteristics. The variables vmin, vmax define the range of positive frequencies K (e.g. in units of radians of phase per micron of scan) within a region of interest (ROI) in the spectrum that we wish to include in the reconstruction of a model signal $\tilde{T}$. The ROI may, for example, be defined as twice the full width at 30% of maximum of the spectrum peak in the frequency domain. Other definitions for the ROI are also possible. Generally, the ROI is selected to capture the meaningful part of the frequency spread, while de-emphasizing parts including mostly noise.

System characterization problem of calculating $\tilde{q}^{sys}$ starting from scan-domain intensity data $I^{sys}$, is discussed in detail below.

LSO Solutions

The discrete square-difference function of Eq.(6) after substituting Eq.(3) is $$\chi_{j,z}^2 = \sum_{\hat{z}=0}^{\hat{N}-1} \{I_{j,z+\hat{z}-\hat{\Delta}} - m_{j,z}^{dc} - m_{j,z}\mathrm{Re}[\tilde{T}_{\hat{z}}\exp(i\varphi_{j,z})]\}^2 w_{\hat{z}}, \quad (14)$$

which can be expanded to $$\chi_{j,z}^2 = \qquad (15)$$
$$\sum_{\hat{z}=0}^{\hat{N}-1}[I_{j,z+\hat{z}-\hat{\Delta}} - m_{j,z}^{dc} - m_{j,z}\cos(\varphi_{j,z})\mathrm{Re}(\tilde{T}_{\hat{z}}) + m_{j,z}\sin(\varphi_{j,z})\mathrm{Im}(\tilde{T}_{\hat{z}})]^2 w_{\hat{z}}.$$

Defining a Solution Vector $$\Lambda_{j,z} = \begin{bmatrix} m_{j,z}^{dc} \\ m_{j,z}\cos(\varphi_{j,z}) \\ m_{j,z}\sin(\varphi_{j,z}) \end{bmatrix}, \quad (16)$$

Eq.(15) can be rewritten as $$\chi_{j,z}^2 = \sum_{\hat{z}=0}^{\hat{N}-1}[I_{j,z+\hat{z}-\hat{\Delta}} - (\Lambda_{j,z})_0 - (\Lambda_{j,z})_1\mathrm{Re}(\tilde{T}_{\hat{z}}) + (\Lambda_{j,z})_2\mathrm{Im}(\tilde{T}_{\hat{z}})]^2 w_{\hat{z}}. \quad (17)$$

The minimum for the square difference function $\chi^2$ can be found by setting to zero the partial derivatives $$\frac{\partial \chi_{j,z}^2}{\partial (\Lambda_{j,z})_0} = -2\sum [\,]w_{\hat{z}} \quad (18)$$

$$\frac{\partial \chi_{j,z}^2}{\partial (\Lambda_{j,z})_1} = -2\sum [\,]\mathrm{Re}(\tilde{T}_{\hat{z}})w_{\hat{z}} \quad (19)$$

$$\frac{\partial \chi_{j,z}^2}{\partial (\Lambda_{j,z})_2} = 2\sum [\,]\mathrm{Im}(\tilde{T}_{\hat{z}})w_{\hat{z}}, \quad (20)$$

where [ ] refers to the term within the brackets of Eq.(15) and the sums are understood be over the local scan index $\hat{z}=0\ldots\hat{N}-1$. Setting Eqs.(18)-(20) to zero results in the following matrix equation for the solution vector $\Lambda$:

$$\Lambda_{j,z} = \Xi_z D_{j,z} \quad (21)$$

for $$\Xi_z = \begin{bmatrix} \sum w_{\hat{z}} & \sum w_{\hat{z}}\mathrm{Re}(\tilde{T}_{\hat{z}}) & -\sum w_{\hat{z}}\mathrm{Im}(\tilde{T}_{\hat{z}}) \\ \sum w_{\hat{z}}\mathrm{Re}(\tilde{T}_{\hat{z}}) & \sum w_{\hat{z}}\mathrm{Re}(\tilde{T}_{\hat{z}})^2 & -\sum w_{\hat{z}}\mathrm{Re}(\tilde{T}_{\hat{z}})\mathrm{Im}(\tilde{T}_{\hat{z}}) \\ \sum w_{\hat{z}}\mathrm{Im}(\tilde{T}_{\hat{z}}) & \sum w_{\hat{z}}\mathrm{Re}(\tilde{T}_{\hat{z}})\mathrm{Im}(\tilde{T}_{\hat{z}}) & -\sum w_{\hat{z}}\mathrm{Im}(\tilde{T}_{\hat{z}})^2 \end{bmatrix}^{-1} \quad (22)$$

$$D_{j,z} = \begin{bmatrix} \sum w_{\hat{z}} I_{j,z+\hat{z}-\hat{\Delta}} \\ \sum w_{\hat{z}}\mathrm{Re}(\tilde{T}_{\hat{z}}) I_{j,z+\hat{z}-\hat{\Delta}} \\ \sum w_{\hat{z}}\mathrm{Im}(\tilde{T}_{\hat{z}}) I_{j,z+\hat{z}-\hat{\Delta}} \end{bmatrix}. \quad (23)$$

The results for the key parameters are:

$$m_{j,z}^{dc} = (\Lambda_{j,z})_0 \quad (24)$$

$$m_{j,z}^2 = (\Lambda_{j,z})_1^2 + (\Lambda_{j,z})_2^2 \quad (25)$$

$$\phi_{j,z}''' = \arctan[(\Lambda_{j,z})_2/(\Lambda_{j,z})_1] \quad (26)$$

where the triple prime to indicates that there is a three-fold uncertainty in the fringe order of the local phase $\phi$, first across scan position, then from pixel to pixel, and finally overall with respect to an absolute starting position for the scan.

Merit Function

The definition of the merit function for locating the signal and determining the surface profile is flexible and depends largely on what one is trying to achieve. For example, if it is sufficiently certain that the peak signal strength corresponds to the signal location, then the simplest merit function is directly proportional to the signal magnitude m that follows from Eq.(25). Define this peak signal strength merit function as $$\Pi_{j,z}^m = m_{j,z}^2. \quad (27)$$

This is a perfectly reasonable general-purpose merit function similar to the dot product merit function used in dot product based techniques such as those disclosed in U.S. patent application US-2005-0078319-A1.

The fitting process used in sliding window LSQ techniques provides additional information useful for locating the signal and determining surface or thickness profiles. The signal can be located by, for each scan position, comparing the model function to the measurement signal. The location of the signal can be identified by finding the scan position corresponding to an optimum fit of the model function to the measurement signal. In cases where the measurement object is made up of multiple surfaces, the signal from each surface can be located by identifying multiple scan positions, each corresponding to an optimum fit.

For example, one may define a merit functions which depends on the similarity between the interferometer signal and the model signal obtained at each global scan position after the least squares fitting has been performed. Such fit-based merit functions can be more effective at locating the signal and determining the surface profile than simple magnitude based merit functions, particularly for applications involving measurement objects with multiple, closely spaces surfaces. The degree of similarity between the interferometer signal and the model function can be quantified in any number of ways, including, for example, the sum of the square differences between the intensity values of the interferometer signal and the intensity values of the model function, or the sum of the absolute value of the differences between the intensity values of the interferometer signal and the intensity values of the model function.

For example, one can define a merit function that depends on the similarity between the model function and the interferometer signal as quantified by the inverse of the $\chi$ minimization function of Eq.(15) after solving for the parameters ($m^{dc}$, m, $\phi$). In order to ensure that the signal magnitude m is still reasonably strong at the selected position, signal magnitude is included in the definition of a best-fit merit function $$\prod_{j,z}^{\chi} = \frac{m_{j,z}^2}{1+\chi_{j,z}^2}. \tag{28}$$

The 1 added to the $\chi^2$ in the denominator prevents accidental division by zero. Most of a SWLI signal has magnitude values too low to be considered in the merit function, so it is sensible to apply a MinMod criterion based on the magnitude m. Those scan positions for which m<MinMod should have the corresponding merit function value $\Pi$ set to zero As in previous thin film algorithms, several measurement modes are available according to the task at hand, with associated peak search logic. When determining the top surface height profile of a test object, the rightmost peak in the merit function along the direction of the scan is identified. If a fit based merit function is used, the location of this peak is the scan position corresponding to an optimum fit of the model function to the measurement signal. When determining film thickness, the strongest two peaks of the merit function are used. If a fit based merit function is used, the location of each peak is a scan position corresponding to an optimum fit of the model function to the measurement signal. When determining the thickness of the topmost thin film in an object composed of multiple films, the first two rightmost peaks along the direction of the scan are identified. Examples of surface height and film thickness calculations are provided below.

Surface Height Calculation

The sliding window LSQ approach can provide both a normal resolution and a high resolution mode. The normal resolution or LSQ-Norm follows directly from a peak search result of the merit function. The high resolution LSQ-High mode uses the phase of the underlying fringes at the identified signal location to refine the normal resolution measurement, as described below.

The peak (or sequence of peaks) locates the integer frame number corresponding to the best fit camera frame number. For the moment, let's assume that there is only one peak of interest and call this $z^{best}$. Interpolation locates the optimum scan position $z^{fine}$ in continuous units of camera frames, for example by quadratic fit to the merit function in the neighborhood of $z^{best}$. The corresponding scan position provides directly the LSQ-Norm height measurement:

$$h_j^{\Theta} = \zeta^{step} z_j^{fine} \tag{29}$$

where the superscript $\Theta$ indicates that the height measurement $h^{\Theta}$ (as opposed to the true height h) is based on a coherence or fringe-contrast analysis.

For the high-resolution measurement, the phase is found by interpolating the phase values $\phi$ calculated from Eq.(26). The result is the phase gap $$A_j'' = \left(\frac{\varphi_{j,z_j^{best}-1}'' + \varphi_{j,z_j^{best}+1}''}{2}\right) + \left(\frac{\varphi_{j,z_j^{best}-1}'' - \varphi_{j,z_j^{best}+1}''}{2}\right)(z_j^{fine} - z_j^{best}). \tag{30}$$

which defines the phase at the frame position $z^{fine}$ of best fit.

The phase gap A" is expected to evolve with scan position because of the accumulated phase at $K^0$. To obtain the phase value $\theta$ at zero scan position, this trend is first removed with $$\theta_j'' = A_j'' + \Theta_j \tag{31}$$

where $\Theta$ is the coherence profile in units of phase at the nominal angular frequency $K^0$:

$$\Theta_j = K^0 h_j^{\Theta}. \tag{32}$$

There remains a fringe-order uncertainty between pixels, which may now be removed with a field-connected, approximate phase gap $\alpha'$ and $$\theta_j' = \theta_j'' - 2\pi \text{Round}\left[\frac{A_j'' - \alpha'}{2\pi}\right] \tag{33}$$

where Round function returns the nearest integer to its argument. The simplest approximate phase gap $\alpha'$ uses a sin-cosine averaging technique described in U.S. Patent Application published as US 2004-0027585 A1 entitled "PHASE GAP ANALYSIS FOR SCANNING INTERFEROMETRY" the contents of which are incorporated herein by reference. Alternatively, the technique disclosed in, e.g., "Determination of fringe order in white-light interference microscopy," Appl. Opt. 41(22) 4571 (2002), can be used. Finally, the surface height profile is given by $$h_j^{\Theta} = \theta_j'/K^0. \tag{34}$$

Film Thickness

The sliding window LSQ technique provides the ability to measure film thickness using a symmetric model signal. The procedure begins with a second-surface merit peak camera frame $z^{best2}$ and interpolated position $z^{fine2}$ in addition to a first surface merit peak camera frame $z^{best1}$ and interpolated position $z^{fine1}$. An initial quantification of thin film thickness is $$L_j^{\Theta} = \frac{\zeta^{step}}{nc_{\Theta}}\left[z_j^{fine2} - z_j^{fine1}\right], \tag{35}$$

where n is the index of the thin film and the factor $c_{\Theta}$ is a correction for the geometric effect of oblique illumination, which because of refraction tends to make the film look thinner that it actually is. The correction factor $c_{\Theta}$ can be determined theoretically, experimentally, or by the compromise technique of a simulation. It does not deviate significantly from 1 unless the illumination NA is large. For this reason it may be preferable to use aperture stops on the higher-magnification objectives, which in any case improve the signal quality for film thickness applications (they are not needed for top-surface only measurements).

A higher-resolution quantification of the measurement starts with the thin-film phase gap $$A'^L_j = A''^{n(2)}_j - A''^{n(1)}_j \tag{36}$$

where $A'^{(1)} = A''$ calculated in Eq.(30) and $A'''^{(2)}$ is calculated in the same manner as Eq.(30) using $z^{best2}$ and $z^{fine2}$ in place of $z^{best}$ and $z^{fine}$. There is only a single prime for the fringe order uncertainty of $A'^L_j$, because it is a phase for the second peak referenced to the first peak so there is no prime associated with a fixed datum plane. The phase profile is then $$\theta'^L_j = A'^L_j + \Theta^L_j \tag{37}$$

where $$\Theta^L_j = K^0 c^\Theta n L^\Theta_j. \tag{38}$$

The field-depending portion of the fringe order uncertainty in $\theta'^L_j$ vanishes with a field-connected, approximate phase gap $\alpha^L$:

$$\theta^L_j = \theta'^L_j - 2\pi \text{Round}\left(\frac{A'^L_j - \alpha^L}{2\pi}\right) \tag{39}$$

Finally $$L^\Theta_j = \theta^L_j / n K^0. \tag{40}$$

This completes the LSQ analysis for profiling a film thickness.

System Characterization

The above sections describe how to generate a complex model signal $\tilde{T}$ empirically from system characterization (SysChar) data. The SysChar data may be identical to the measurement data if the part is a homogeneous solid surface. For complicated surface structure such a thin film, we use a separate SysChar measurement and store the results in a file, using a frequency-domain representation $\overline{\tilde{q}}^{sys}$ of the averaged signal spectrum. As noted above, calculation of the complex model signal $\tilde{T}$ follows from an inverse DFT of $\overline{\tilde{q}}^{sys}$ using a selected range of frequencies within the ROI.

If the scan domain SysChar signal $I^{sys}$ has uniform sampling, then a forward Fourier Transform (FT) provides directly $q^{sys}$ for each pixel to contribute to the positive frequency average $\overline{\tilde{q}}^{sys}$:

$$\tilde{q}^{sys}_{j,v>0} = \sum_{z=0}^{N_{sys}-1} I^{sys}_j \exp[i\zeta_z K_v]. \tag{41}$$

The ~ over $q^{sys}$ indicates that the spectrum in Eq.(41) contains only the positive nonzero frequencies. The next step is to extract and average the magnitudes and phases within the ROI defined by the frequency indices (or bins) vmin<v<vmax:

$$\overline{P^{sys}_v} = \frac{1}{Y}\sum_{j=0}^{Y-1} P^{sys}_{j,v} \tag{42}$$

$$\overline{\phi'^{sys}_{j,v}} = \frac{1}{Y}\sum_{j=0}^{Y-1} \phi''^{sys}_{j,v} \tag{43}$$

where $$P^{sys}_{j,v} = |\tilde{q}^{sys}_{j,v}| \tag{44}$$

and the measured phase as a function of angular frequency is $$\phi''^{sys}_{j,v} = \text{connect}(\phi'''^{sys}_{j,v}) \tag{45}$$

for $$\phi'''^{sys}_{j,v} = \arg(\tilde{q}^{sys}_{j,v}). \tag{46}$$

The spectral contributions outside the ROI are set to zero. The three primes for the phase data $\phi'''^{sys}$ in the frequency domain indicate that there are multiple $2-\pi$ uncertainties in the phase information: from angular frequency to angular frequency K, from pixel to pixel, and overall with respect to an absolute reference. The connect function in Eq.(45) removes one of these primes by connecting across angular frequencies for each pixel, similarly to the way it is done in FDA. The field averaging in Eq.(43) removes another prime, leaving only the single prime that reminds us that the overall offset value for the phase is unknown. After field-averaging the phase and the magnitudes independently we construct the height-independent partial spectrum $$\overline{\tilde{q}^{sys}_v} = \overline{P^{sys}_{v>0}} \exp[\text{nonlin}(\overline{\phi'^{sys}_{v>0}})] \tag{47}$$

where the function nonlin returns that portion of the argument that is nonlinear with respect to angular frequency K, thereby removing the linear change of phase with angular frequency associated with surface profile.

Note that using the correct value of $K^0$ is a key parameter in determining the high-resolution profile $h^\Theta$, because we make the assumption that the phase values $\phi$ relate to this frequency. An excellent estimate of $K^0$ follows from the weighted average or centroid of the frequencies in the spectrum:

$$K^0 = \sum_{v=vmin}^{vmax}(\overline{P^{sys}_{j,v>0}})^2 K_v \bigg/ \sum_{v=vmin}^{vmax}(\overline{P^{sys}_{j,v>0}})^2. \tag{48}$$

Fringe-Removed Imaging Using the Signal Offset

The offset parameter $m^{dc}$ calculated at the best fit camera frame number $z^{best}$ is an excellent estimate of the fringe-removed intensity $I^0$:

$$I^0_j = m_{j,z^{best}}^{dc} \tag{49}$$

Although one could argue for interpolation to the $z^{fine}$ value, $m^{dc}$ varies slowly enough that this seems unnecessary.

Computational Efficiency

This LSQ calculations include the matrix multiplication of Eq.(21) and related sums which in principle are performed for every camera frame z and at every pixel j. Although this calculation seems at first to be excessive and time consuming, it is not as intensive as one might suppose.

With some care, the total number of calculations is comparable (although certainly greater) to that required in dot product dot product based techniques. Thus, LSQ techniques are rapid enough for production applications.

Firstly note that the 3×3 fit matrix $\Xi$ does not include the experimental signal and therefore can be calculated in advance of data acquisition. Next, the last two elements $D_1$, $D_2$ given in Eq.(23) are the real and imaginary parts, respectively, of the dot product of the windowed complex signal model $w\hat{T}$ and the experimental signal I, a calculation of the type already required by dot product based techniques. The same comparison applies to the number of arctangent calculations, which are the same. The additional in-process calculations therefore with respect to dot product based techniques for the simple merit function of Eq.(27) are the windowed summation $D_0$ given in Eq.(23), which requires $\hat{N}$ multiplies and additions, and the matrix calculation of Eq.(21), which involves 9 multiplies and additions. These operations are generally fast, as they do not involve trigonometric functions or divides.

The more aggressive fit-based merit function of Eq.(28) evaluates the square difference function $\chi$ for the found values of $\Lambda_1$, $\Lambda_2$ at each scan position and at each pixel using in Eq.(17). In essence this requires recovering for use and performing something like $4\hat{N}$ multiplies and additions, which could impact processing time. There are no extra trigonometric functions and only one additional divide.

Sliding-window LSQ is a scan-domain signal algorithm similar to the dot product technique and therefore a candidate for several speedup strategies, including sparse sampling of the merit function, pre-testing estimated signal modulation to reduce the number of needless calculations, and rapid searching for only the top-surface reflection of a multilayer film.

Flowchart

Figure 7:
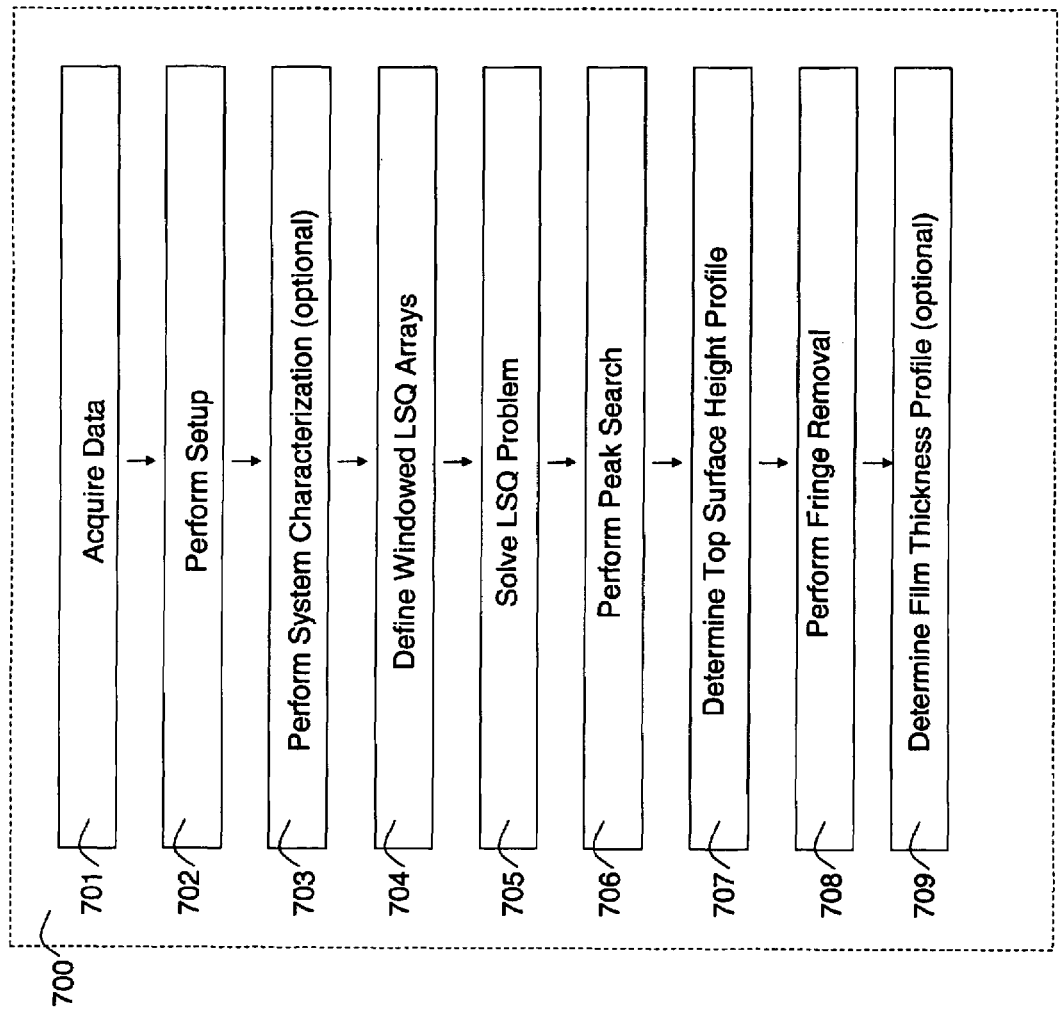
FIG. 7 is a flow chart showing the flow of an exemplary embodiment of the sliding window LSQ pattern matching technique.

In light of the above, referring to FIG. 7, a flowchart 700 for an exemplary application of the sliding window LSQ technique is shown. In the first step 701, SWLI measurement data $I_{j,z}$ is acquired, for example, directly from an interferometer system or from a data file. If a system characterization has previously been performed, system characterization data $\tilde{q}_{j,\nu}^{sys}$ is read from a file. Alternatively, SWLI system characterization data $I_{j,z}^{sys}$ is acquired to be used in system characterization step 703. The SWLI system characterization data can be the measurement data itself.

In step 702, set up is performed. Various parameters, e.g. N, $\hat{N}$, Y, are set. The global and local scans $\zeta^{step}$, $\zeta_z$, $\hat{\zeta}_z$ are set, and the frequency domain scale K is established.

If system characterization data $\tilde{q}_{j,\nu}^{sys}$ is not read from a file in step 701, it is calculated from SWLI system characterization data $I_{j,z}^{sys}$ in step 703. The system characterization data is frequency analyzed, and the positive nonzero frequency components are chosen, yielding $\tilde{q}_{j,\nu}^{sys}$. The frequency domain magnitudes and phases are averaged over the image field, yielding $\overline{P_\nu^{sys}}$ and $\overline{\phi'}_{j,\nu}^{sys}$ respectively. The frequency domain region of interest (ROI) where the useful signal resides is established. Finally, the linear portion of the phase is removed (thereby removing height bias of the system characterization) and a partial spectrum $\overline{\tilde{q}_\nu^{sys}}$ is created from the field averaged magnitude and phases. This spectrum is stored as system characterization data.

In step 704, the windowed LSQ arrays are defined. The model signal $\hat{T}_z$ is calculated by taking the discrete Fourier transform (DFT) of the frequency-domain system characterization data $\tilde{q}^{sys}$. A tapered evaluation window $w_z$ is defined. The signal model and window are used to define the LSQ fit matrix $\Xi$, as described above.

In step 705, the LSQ problem is solved. The dot product vector $D_{j,z}$ is calculated using the measurement data. Optionally, in order to improve computational efficiency, a pre-scan may be used initially to identify areas of strong signal strength. The LSQ problem is solved to find the best phase and magnitude values $\Lambda_{j,z}$ for an optimum fit of the model signal to the data at each scan position. Those scan positions having insufficient signal strength for further processing are identified and discarded. If a fit based merit function is to be used, the resulting square-difference value for the LSQ solutions $\chi_{j,z}^2$ is calculated. Finally either a magnitude based merit function $\Pi_{j,z}^m$, or a fit based merit function $\Pi_{j,z}^\chi$ is calculated.

In step 706, a peak search is performed. The merit function $\Pi$ is searched to find the optimum camera frame $z_j^{best1}$ for either the first valid peak or the highest peak. If a film thickness calculation is desired, the merit function $\Pi$ is searched to find a second (or further) optimum camera frame $z_j^{best2}$ for a second valid peak.

In step 707, a top surface height profile is determined. The mean or nominal interference data frequency $K^0$ is determined from the weighted averages of the system characterization spectrum. An improved scan position estimate $z_j^{fine1}$ is determined based on $z_j^{best}$ by interpolating between discrete scan positions. A normal resolution surface height profile $h_j^\Theta$ is determined by equating the measured surface height with the scan position $\zeta^{step}z_j^{fine1}$. The phase gap $A''_j$ is determined by interpolating to find the phase $\phi''$ at $z_j^{fine1}$. Phase gap analysis is used to find a field-connected, approximate phase gap $\alpha'$. The fringe order uncertainty is removed and the high-resolution surface height profile $h_j^\Theta$ is calculated.

In step 708, fringe removal is performed. The offset at the optimum camera frame $z_j^{best1}$ is identified and equated to the fringe-removed intensity $I^0$ at each pixel, yielding a fringe removed intensity profile $I_j^0$.

If a film thickness profile measurement is desired, step 709 is performed. An improved scan position estimate $z_j^{fine2}$ is determined based on $z_j^{best2}$ by interpolating between discrete scan positions. A normal resolution film thickness profile $h_j^\Theta$ is determined by equating the measured thickness profile $L_j^\Theta$ with the difference in scan positions $z_j^{best1}$ and $z_j^{best2}$, scaled by the index of refraction. The film thickness phase gap $A'_j^L$ is determined by interpolating to find the phase values at the two peak positions $z_j^{fine1}$ and $z_j^{fine2}$. Phase gap analysis is used to find a field-connected, approximate phase gap $\alpha'^L$. The fringe order uncertainty is removed and the high-resolution film thickness profile $L_j^\Theta$ is calculated.

Exemplary Applications

The low coherence interferometry methods and systems described above may used for any of the following surface analysis problems: simple thin films; multilayer thin films; sharp edges and surface features that diffract or otherwise generate complex interference effects; unresolved surface roughness; unresolved surface features, for example, a sub-wavelength width groove on an otherwise smooth surface; dissimilar materials; polarization-dependent properties of the surface; and deflections, vibrations or motions of the surface or deformable surface features that result in incident-angle dependent perturbations of the interference phenomenon. For the case of thin films, the variable parameter of interest may be the film thickness, the refractive index of the film, the refractive index of the substrate, or some combination thereof. Exemplary applications including objects and devices exhibit such features are discussed next.

Semiconductor Processing

The systems and methods described above can be used in a semiconductor process for tool specific monitoring or for controlling the process flow itself. In the process monitoring application, single/multi-layer films are grown, deposited, polished, or etched away on unpatterned Si wafers (monitor wafers) by the corresponding process tool and subsequently the thickness and/or optical properties are measured using the interferometry system employing the sliding window LSQ technique disclosed herein. The average, as well as within wafer uniformity, of thickness (and/or optical properties) of these monitor wafers are used to determine whether the associated process tool is operating with targeted specification or should be retargeted, adjusted, or taken out of production use.

In the process control application, latter single/mulit-layer films are grown, deposited, polished, or etched away on patterned Si, production wafers by the corresponding process tool and subsequently the thickness and/or optical properties are measured with the interferometry system employing the sliding window LSQ technique disclosed herein. Production measurements used for process control typical include a small measurement site and the ability to align the measurement tool to the sample region of interest. This site may consists of multi-layer film stack (that may itself be patterned) and thus requires complex mathematical modeling in order to extract the relevant physical parameters. Process control measurements determine the stability of the integrated process flow and determine whether the integrated processing should continue, be retargeted, redirected to other equipment, or shut down entirely.

Specifically, for example, the interferometry system disclosed herein can be used to monitor the following equipment: diffusion, rapid thermal anneal, chemical vapor deposition tools (both low pressure and high pressure), dielectric etch, chemical mechanical polishers, plasma deposition, plasma etch, lithography track, and lithography exposure tools. Additionally, the interferometry system disclosed herein can be used to control the following processes: trench and isolation, transistor formation, as well as interlayer dielectric formation (such as dual damascene).

Copper Interconnect Structures And Chemical Mechanical Polishing

It is becoming common among chip makers to use the so-called 'dual damascene copper' process to fabricate electrical interconnects between different parts of a chip. This is an example of a process which may be effectively characterized using a suitable surface topography system. The dual damascene process may be considered to have six parts: (1) an interlayer dielectric (ILD) deposition, in which a layer of dielectric material (such as a polymer, or glass) is deposited onto the surface of a wafer (containing a plurality of individual chips); (2) chemical mechanical polishing (CMP), in which the dielectric layer is polished so as to create a smooth surface, suitable for precision optical lithography, (3) a combination of lithographic patterning and reactive ion etching steps, in which a complex network is created comprising narrow trenches running parallel to the wafer surface and small vias running from the bottom of the trenches to a lower (previously defined) electrically conducting layer, (4) a combination of metal deposition steps which result in the deposition of copper trenches and vias, (5) a dielectric deposition step in which a dielectric is applied over the copper trenches and vias, and (6) a final CMP step in which the excess copper is removed, leaving a network of copper filled trenches (and possibly vias) surrounded by dielectric material.

Figure 9A:
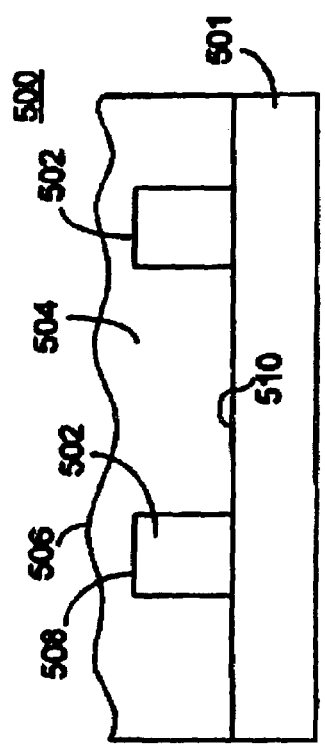
FIG. 9a is a schematic showing a device 500 exemplary of the film structure resulting from the deposition of a dielectric 504 over copper features 502 deposited on a substrate 501.

Referring to FIG. 9a, a device 500 is exemplary of the film structure resulting from the deposition of a dielectric 504 over copper features 502 deposited on a substrate 501. The dielectric 504 has a non-uniform outer surface 506 exhibiting height variations therealong. Interference signals obtained from device 500 can include interference patterns resulting from surface 506, an interface 508 between copper features 502 and dielectric 504, and an interface 510 between substrate 501 and dielectric 504. The device 500 may include a plurality of other features that also generate interference patterns.

Figure 9B:
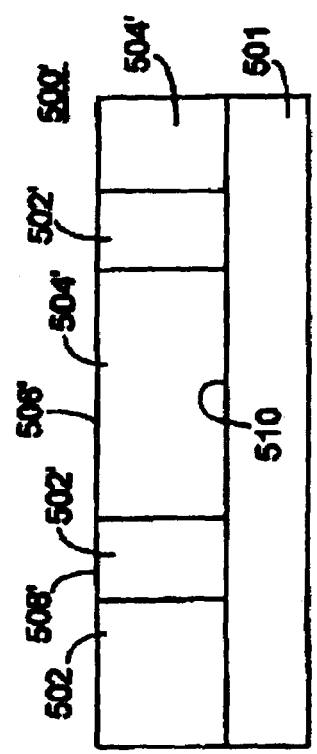
FIG. 9b is a schematic diagram of the device 500 shown in FIG. 9a after undergoing chemical mechanical processing.

Referring to FIG. 9b, a device 500' illustrates the state of device 500 after the final CMP step. The upper surface 506 has been planarized to a surface 506', and interface 508 may now be exposed to the surroundings. Interface 510 at the substrate surface remains intact. Device performance and uniformity depends critically on monitoring the planarization of surface 504. It is important to appreciate that the polishing rate, and therefore the remaining copper (and dielectric) thickness after polishing, depends strongly and in a complex manner on the polishing conditions (such as the pad pressure and polishing slurry composition), as well as on the local detailed arrangement (i.e., orientation, proximity and shape) of copper and surrounding dielectric regions. Hence, portions of surface 506 over copper elements 502 may etch at different rates than other portions of surface 506. Additionally, once interface 508 of copper elements 502 is exposed, the dielectric and copper elements may exhibit different etch rates.

This 'position dependent polishing rate' is known to give rise to variable surface topography on many lateral length scales. For example, it may mean that chips located closer to the edge of a wafer on aggregate are polished more rapidly than those located close to the center, creating copper regions which are thinner than desired near the edges, and thicker than desired at the center. This is an example of a 'wafer scale' process nonuniformity—i.e., one occurring on length scale comparable to the wafer diameter. It is also known that regions which have a high density of copper trenches polish at a higher rate than nearby regions with low copper line densities. This leads to a phenomenon known as 'CMP induced erosion' in the high copper density regions. This is an example of a 'chip scale' process non-uniformity—i.e., one occurring on a length scale comparable to (and sometimes much less than) the linear dimensions of a single chip. Another type of chip scale nonuniformity, known as 'dishing', occurs within single copper filled trench regions (which tend to polish at a higher rate than the surrounding dielectric material). For trenches greater than a few microns in width dishing may become severe with the result that affected lines later exhibit excessive electrical resistance, leading to a chip failure.

CMP induced wafer and chip scale process nonuniformities are inherently difficult to predict, and they are subject to change over time as conditions within the CMP processing system evolve. To effectively monitor, and suitably adjust the process conditions for the purpose of ensuring that any nonuniformities remain within acceptable limits, it is important for process engineers to make frequent non-contact surface topography measurements on chips at a large number and wide variety of locations. This is possible using embodiments of the interferometry methods and systems described above.

In some embodiments one or more spatial properties, e.g., the topography of surface 506 and/or the thickness of dielectric 504, are monitored by obtaining low coherence interference signals from the structure before and/or during CMP. Based on the spatial properties, the polishing conditions can be changed to achieve the desired planar surface 506'. For example, the pad pressure, pad pressure distribution, polishing agent characteristics, solvent composition and flow, and other conditions can be determined based on the spatial properties. After some period of polishing, the spatial property can again be determined and the polishing conditions changed as needed. The topography and/or thickness is also indicative of the end-point at which, e.g., surface 504' is achieved. Thus, the low coherence interference signals can be used to avoid depressions caused by over polishing different regions of the object. The low coherence interference methods and systems are advantageous in this respect because spatial properties of the device, e.g., the relative heights of the surface of the dielectric (a) over copper elements 502 and (b) over substrate surface 510 but adjacent copper elements 502 can be determined even in the presence of the multiple interfaces.

Photolithography

Figure 8A:
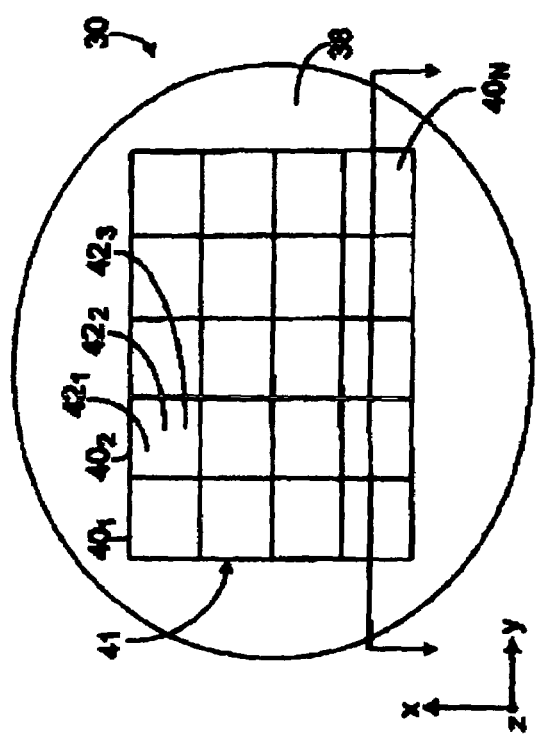
FIG. 8a is a schematic diagram showing a top down view of an object 30 which includes a substrate, e.g., a wafer, 32 and an overlying layer, e.g., photoresist layer 34.
Figure 8B:
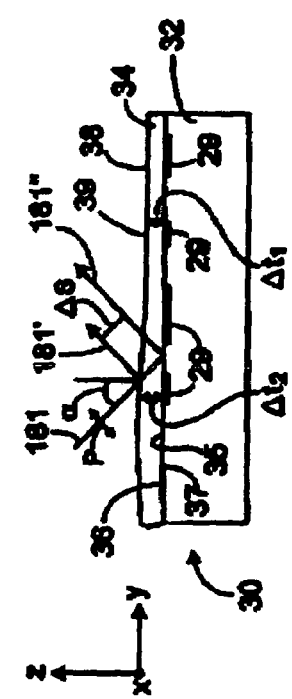
FIG. 8b is a schematic diagram showing a side on view of the object 30.

In many microelectronics applications, photolithography is used to pattern a layer of photoresist overlying a substrate, e.g., a silicon wafer. Referring to FIGS. 8a and 8b, an object 30 includes a substrate, e.g., a wafer, 32 and an overlying layer, e.g., photoresist layer 34. Object 30 includes a plurality of interfaces as occur between materials of different refractive index. For example, an object-surroundings interface 38 is defined where an outer surface 39 of photoresist layer 34 contacts the environment surrounding object 30, e.g., liquid, air, other gas, or vacuum. A substrate-layer interface 36 is defined between a surface 35 of wafer 32 and a bottom surface 37 of photoresist layer 34. Surface 35 of the wafer may include a plurality of patterned features 29. Some of these features have the same height as adjacent portions of the substrate but a different refractive index. Other features may extend upward or downward relative to adjacent portions of the substrate. Accordingly, interface 36 may exhibit a complex, varying topography underlying the outer surface of the photoresist.

A photolithography apparatus images a pattern onto the object. For example, the pattern may correspond with elements of an electronic circuit (or the negative of the circuit). After imaging, portions of the photoresist are removed revealing the substrate underlying the removed photoresist. The revealed substrate can be etched, covered with deposited material, or otherwise modified. Remaining photoresist protects other portions of the substrate from such modification.

To increase manufacturing efficiencies, more than one device is sometimes prepared from a single wafer. The devices may be the same or different. Each device requires that a subset of the wafer be imaged with a pattern. In some cases, the pattern is sequentially imaged onto different subsets. Sequential imaging can be performed for several reasons. Optical aberrations can prevent achieving adequate pattern focus quality over larger areas of the wafer. Even in the absence of optical aberrations, the spatial properties of the wafer and photoresist may also prevent achieving adequate pattern focus over large areas of the wafer. Aspects of the relationship between the spatial properties of the wafer/resist and focus quality are discussed next.

Referring back to FIG. 8b, object 30 is shown with a number N subsets $40_i$, each smaller than a total area 41 the object to be imaged. Within each subset $40_i$, spatial property variations, e.g., height and slope variations of the wafer or photoresist, are typically smaller than when taken over the total area 41. Nonetheless, the wafer or photoresist of different subsets $40_i$ typically have different heights and slopes. For example, layer 34 exhibits thicknesses $\Delta t_1$ and $\Delta t_2$, which vary the height and slope of surface 39 (FIG. 7a). Thus, each subset of the object may have a different spatial relationship with the photolithography imager. The quality of focus is related to the spatial relationship, e.g., the distance between the object and the photolithography imager. Bringing different subsets of the object into proper focus may require relative repositioning of the object and imager. Because of the object height and slope variations, proper subset focus cannot be achieved solely by determining the position and orientation of the object with respect to a portion of the object that is remote to the imaged subset, e.g., a side 43 of the object.

Proper focus can be achieved by determining a spatial property of an object within a subset of the object to be imaged (or otherwise processed). Once the position of the subset has been determined, the object (and/or a portion of the photolithography imager) can be moved, e.g., translated, rotated, and/or tilted, to modify the position of the subset with respect to a reference, e.g., a portion of the photolithography imager. The determination and movement (if necessary) can be repeated for each subset to be imaged.

The determination of the spatial property of the subset can include determining a position and/or height of one or more points of an outer surface of a thin layer of the object, the one or more points lying within the subset of the object to be imaged. For example, the position and orientation of the outer surface 39 of subset $40_2$ (FIG. 8a) can be determined based upon the positions of points $42_1$-$42_3$ within the subset. The determination of the spatial property of the subset to be imaged can include using an interferometer to illuminate the subset with light and detecting an interference signal including light reflected from the illuminated subset. In some embodiments, a plurality of subsets are simultaneously imaged with light to obtain a plurality of interference signals. Each interference signal is indicative of one or more spatial properties of a subset. Thus, the interference signals can be used to prepare an image indicative of the topography of the object over a plurality of the subsets. During photolithography of the subsets, the wafer is positioned based upon the topography of the individual subsets as determined from the plurality of interference signals. Hence, each subset can be positioned for optimum focus with respect to the photolithography apparatus.

Detecting an interference signal from each subset of an object to be imaged can include detecting light reflected from the subset and reference light over an OPD range that is at least as large as a coherence length of the detected light. For example, the light may be detected at least over its coherence length. In some embodiments, the interferometer is configured so that the light reflected from the illuminated subset is dominated by light reflected from either an outer interface (such as outer surface 39) or an inner interface (such as interface 36). In some embodiments, a spatial property of an object is determined based on only a portion of the interference signal. For example, if the interference signal includes two or more overlapping interference patterns, a spatial property of the object can be determined based upon a portion of one of the interference patterns that is dominated by contributions from a single interface of the object.

Solder Bump Processing

Referring to FIGS. 10a and 10b, a structure 1050 is exemplary of a structure produced during solder bump processing. Structure 1050 includes a substrate 1051, regions 1002 non-wettable by solder, and a region 1003 wettable by solder. Regions 1002 have an outer surface 1007. Region 1003 has an outer surface 1009. Accordingly, an interface 1005 is formed between regions 1002 and substrate 1001.

During processing a mass of solder 1004 is positioned in contact with wettable region 1003. Upon flowing the solder, the solder forms a secure contact with the wettable region 1003. Adjacent non-wettable regions 1002 act like a dam preventing the flowed solder from undesirable migration about the structure. It is desirable to know spatial properties of the structure including the relative heights of surfaces 1007, 1009 and the dimensions of solder 1004 relative to surface 1002. As can be determined from other discussions herein, structure 1050 includes a plurality of interfaces that may each result in an interference pattern. Overlap between the interference patterns prevents accurate determinate of the spatial properties using known interference techniques. Application of the systems and methods discussed herein allow the spatial properties to be determined.

Spatial properties determined from structure 1050 can be used to change manufacturing conditions, such as deposition times for layers 1002, 1003 and the amount of solder 1004 used per area of region 1003. Additionally, heating conditions used to flow the solder can also be changed based on the spatial properties to achieve adequate flow and or prevent migration of the solder.

Liquid Crystal Displays

Figure 11:
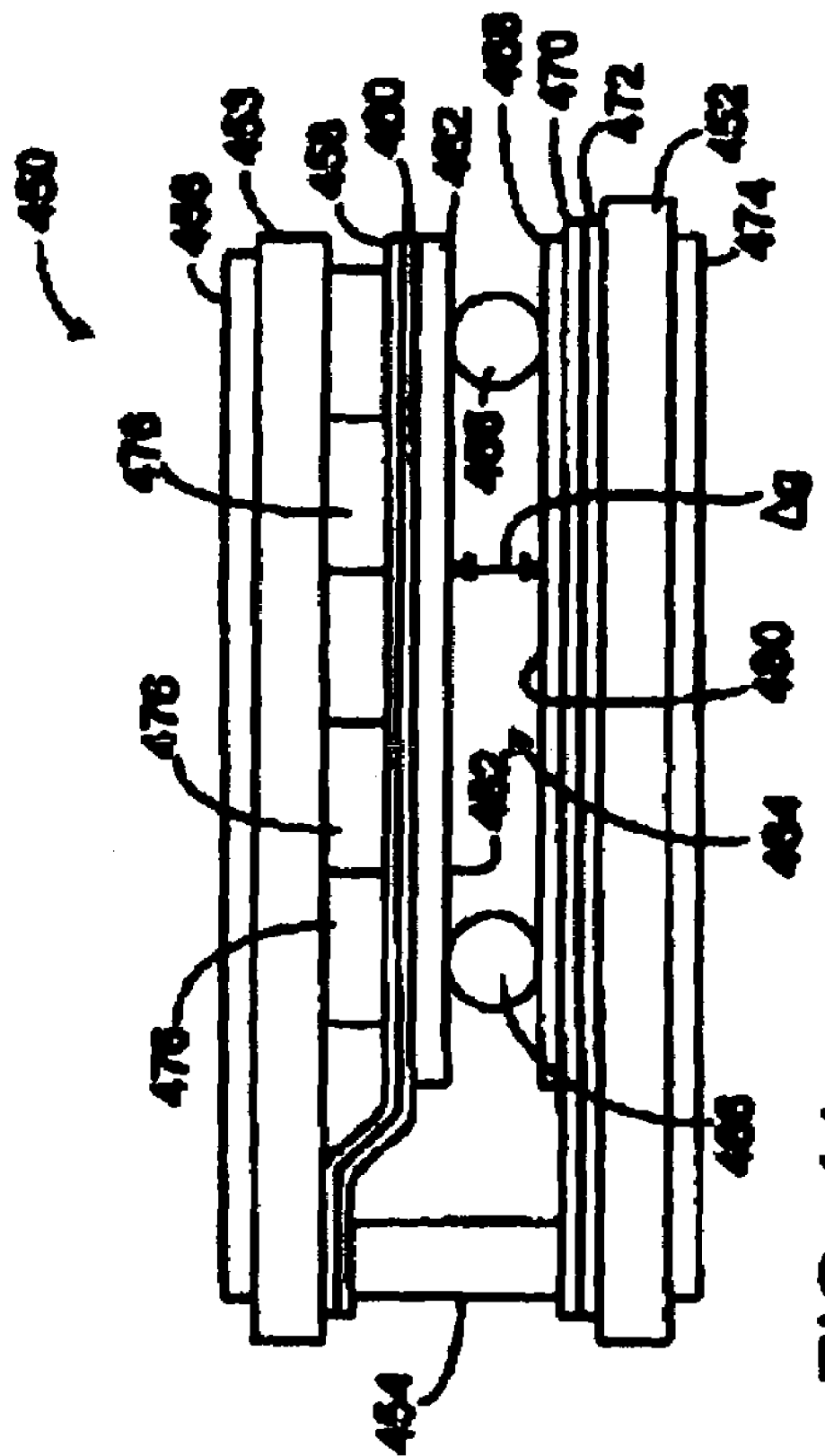
FIG. 11 is a schematic diagram of a passive matrix LCD 450 is composed of several layers.

Referring to FIG. 11, a passive matrix LCD 450 is composed of several layers. The main parts are two glass plates 452,453 connected by seals 454. A polarizer 456 is applied to the front glass plate 453 in order to polarize incoming light in a single direction. The polarized light passes through the front glass plate 453. An Indium Tin Oxide (ITO) layer 458 is used as an electrode. A passivation layer 460, sometimes called hard coat layer, based on SiOx is coated over the ITO 458 to electrically insulate the surface. Polyimide 462 is printed over the passivation layer 460 to align the liquid crystal fluid 464. The liquid crystal fluid is sensitive to electric fields and changes orientation when an electric field is applied. The liquid crystal is also optically active and rotates the polarization direction of the incoming light. The cell gap $\Delta g$, i.e., thickness of the liquid crystal layer 464, is determined by spacers 466, which keep the two glass plates 452,453 at a fixed distance. When there is no electric potential from the front plate 453 to the rear plate 452, the polarized light is rotated 90.degree. as it passes through the liquid crystal layer 464. When an electric potential is applied from one plate to the other plate the light is not rotated. After the light has passed through the liquid crystal layer 464, it passes through another polyimide layer 468, another hard coat layer 470, a rear ITO electrode 472, and the rear glass plate 452. Upon reaching a rear polarizer 474, the light either transmitted through or absorbed, depending on whether or not it has been rotated 90.degree. The cell 450 may include filters 476 or other colorizing elements to provide a color display.

The cell gap $\Delta g$ determines to a great extent the opto-electrical properties of the LCD, e.g., the contrast ratio and brightness. Cell gap control during manufacturing is critical to obtaining uniform, quality displays. The actual cell gap may differ from the dimensions of spacers 466 because, during assembly, pressure or vacuum is applied to introduce the liquid crystal medium, seals 454 cure and may change dimensions, and the added liquid crystal medium generates capillary forces between plates 452,453. Both before and after adding the liquid crystal medium 464, surfaces 480,482 of plates 452,453 reflect light that results in an interference pattern indicative of the cell gap $\Delta g$. The low coherence nature of the interference signal either itself or in combination with the described interference signal processing techniques can be used to monitor properties of the cell including the cell gap $\Delta g$ during manufacture even in the presence of interfaces formed by other layers of the cell.

An exemplary method can include obtaining a low coherence interference signal including interference patterns indicative of the cell gap $\Delta g$ prior to adding layer 464. The cell gap (or other spatial property of the cell) is determined from the interference patterns and can be compared to a specified value. Manufacturing conditions, e.g., a pressure or vacuum applied to plates 452,453 can be changed to modify the cell gap $\Delta g$ if a difference between the specified value and the determined cell gap exceeds tolerances. This process can be repeated until achieving the desired cell gap. Liquid crystal medium is then introduced into the cell. The amount of liquid crystal medium to be added can be determined from the measured spatial property of the cell. This can avoid over- or underfilling the cell. The filling process can also be monitored by observing interference signals from the surfaces 480,482. Once the cell has been filed, additional low coherence interference patterns are obtained to monitor the cell gap $\Delta g$ (or other spatial property). Again, the manufacturing conditions can be changed so that the cell gap is maintained or brought within tolerances.

Laser Scribing and Cutting

Lasers can be used to scribe objects in preparation for separating different, concurrently manufactured structures, e.g., microelectronics structures. The quality of separation is related to the scribing conditions, e.g., laser focus size, laser power, translation rate of the object, and scribe depth. Because the density of features of the structure may be large, the scribe lines may be adjacent thin film or layers of the structures. Interfaces associated with the thin film or layers may create interference patterns that appear when interferometry is used to determine the scribe depth. The methods and systems described herein can be used to determine the scribe depth even in the presence of such adjacent films or layers.

An exemplary method can include scribing one or more electronic structures and separating the structures along the scribe lines. Before and/or after separation, low coherence interference signals can be used to determine the depth of scribe. Other scribing conditions are known, e.g., laser spot size, laser power, translation rate. The scribe depth can be determined from the interference signals. The quality of separation as a function of the scribing conditions, including the scribe depth, can be determined by evaluating the separated structures. Based on such determinations, the scribing conditions necessary to achieve a desired separation quality can be determined. During continued manufacturing, low coherence interference signals can be obtained from scribed regions to monitor the process. Scribing conditions can be changed to maintain or bring the scribe properties within tolerances.

EXAMPLES

Determining a spatial property of a measurement object is further described the context of the five following non-limiting examples.

1. Determining a Surface Height Profile of a Single-Surface Measurement Object (Simulated Data)

Figure 12:
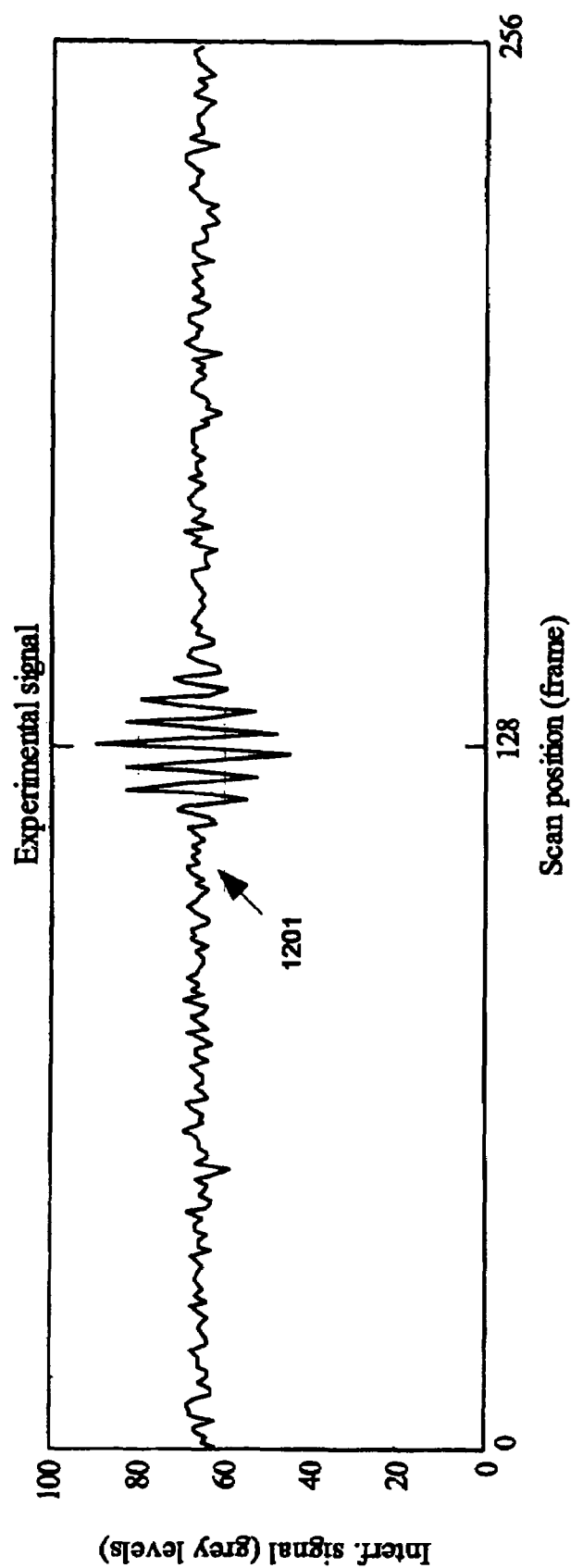
FIG. 12 is a plot of a simulated SWLI measurement signal 1201.

Referring to FIG. 12, simulated interference signal 1201 is obtained from a single point on a solid silicon dioxide object. Interference signal 1201 is but one of a total 101 interference signals representing a linear trace across the object surface. For convenience, the remaining 100 interference signals are not shown. The silicon dioxide object surface has an approximately spherical profile with PV=600 nm. The interferometer system uses an irradiation wavelength of 550 nm with a bandwidth of 100 nm. The bandwidth is Gaussian in wavenumber. The numerical aperture of the system is 0.01 for normal incidence, collimated light. Each interference signal has a full scale digital resolution of 256 grey scale steps. The average signal strength is 20 grey levels amplitude AC above 65 grey levels DC. The signals have random noise having a standard deviation of 2 grey levels. This is a solid surface example with no film structure and thus a symmetric model signal and the magnitude-based merit function of Eq.(27) will be used to obtain a surface height profile.

Figure 13B:
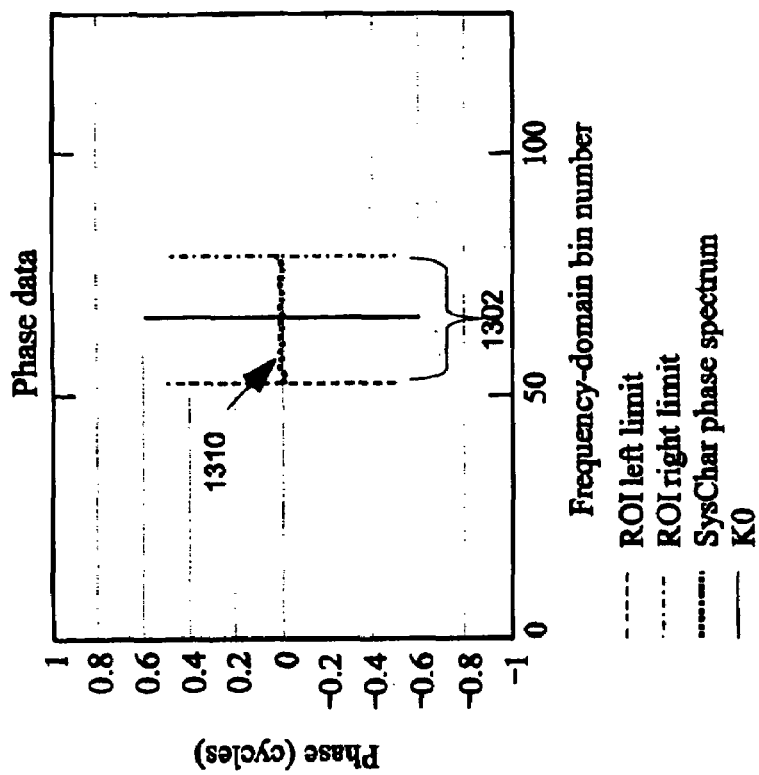
FIG. 13b is a plot of phase data for the system characterization spectrum derived from measurement signal 1201.
Figure 13A:
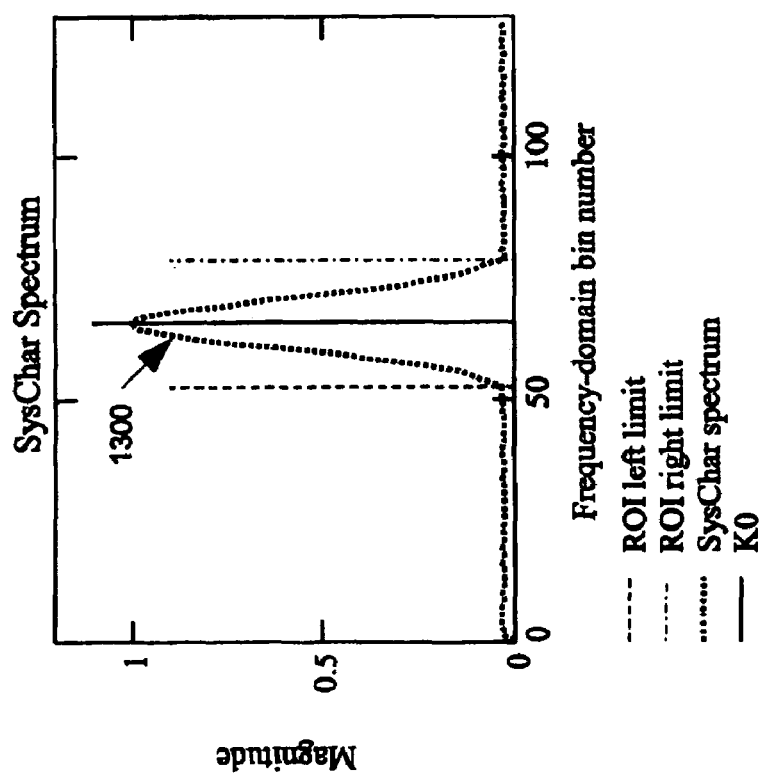
FIG. 13a is a plot of the system characterization spectrum derived from measurement signal 1201.

The 101 interference signals are transformed to an inverse domain using the Fourier transform. The transformed interference signals are used to prepare a transformed template including contributions from all of the transformed interference signals. The transformed signals are averaged, using the techniques described above, to produce transformed system characterization intensity data. Referring to FIGS. 13a and 13b, the magnitude spectrum 1300 and phase 1310 of the transformed SysChar data are shown. The system characterization spectrum is peaked at a value $K^0$. A region of interest 1302 is shown as centered about the peak. Note the uniform noise floor of the magnitude spectrum 1300, due to the averaging over 101 signals.

Figure 14:
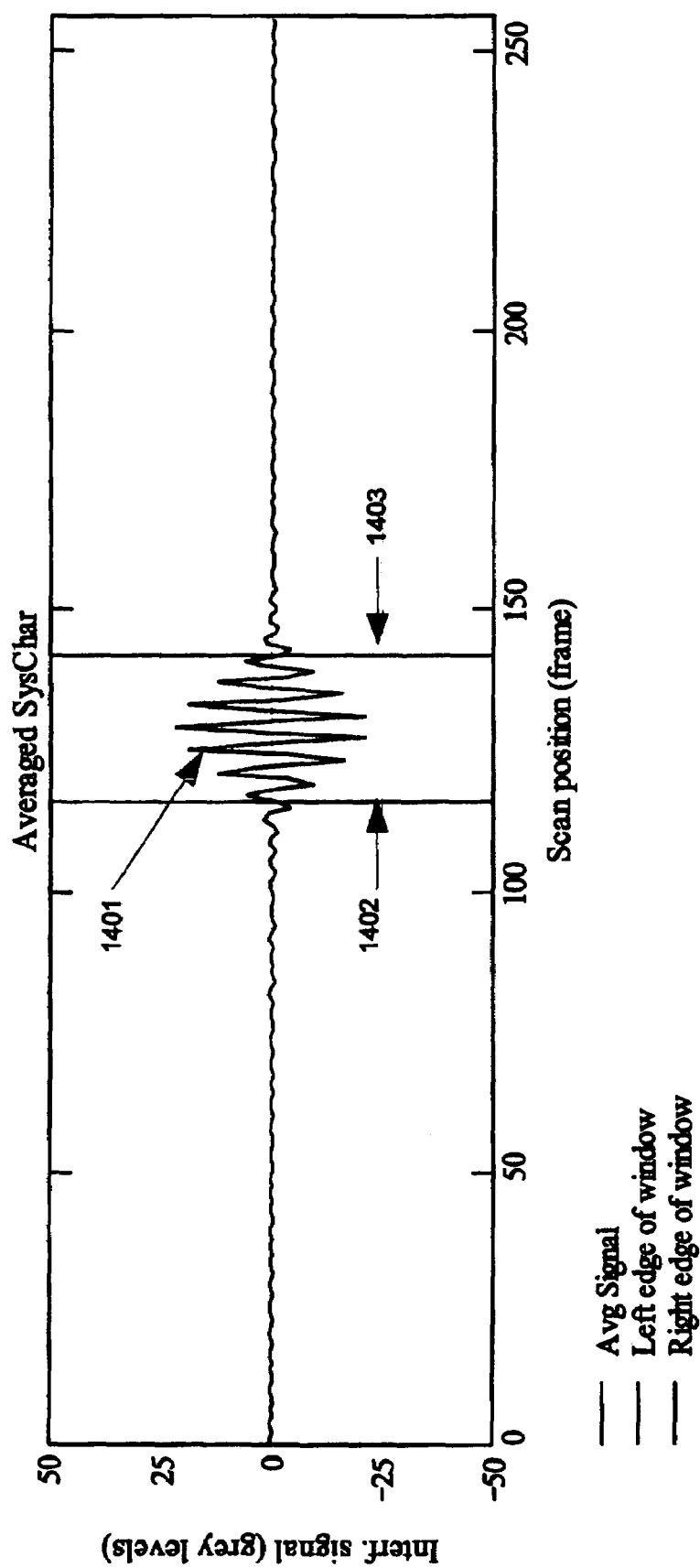
FIG. 14 is a plot of averaged system characterization data derived from measurement signal 1201.

Referring to FIG. 14, averaged system characterization intensity data 1401 from which the model signal $\tilde{T}$ is extracted is shown in the scan position domain. The boundaries of the window 1402, 1403 are also shown. Note the absence of random noise as compared with FIG. 12 due to averaging and ROI filtering in the frequency domain.

Referring to FIG. 15a, symmetric model signal $\tilde{T}$ 1501 is shown. FIG. 15b shows model signal $\tilde{T}$ 1501 multiplied by a window function 1502.

Figure 16A:
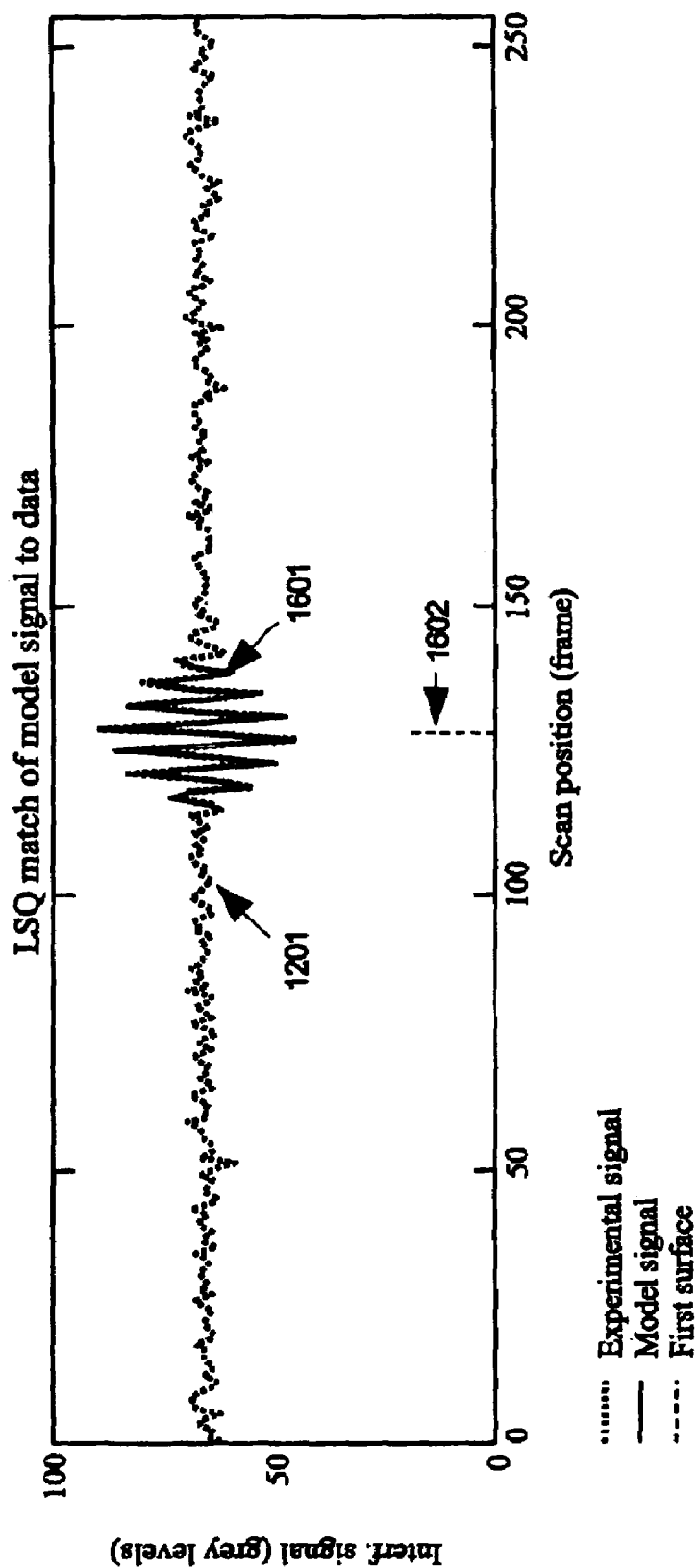
FIG. 16a is a plot showing the result of the LSQ pattern matching analysis of measurement signal 1201.

Referring to FIG. 16a, the model signal 1601 has been fit to the simulated data set 1201 of FIG. 12 using the sliding window LSQ technique. The model signal is shown at the best fit camera frame $z^{best}$ 1602, after applying the parameters $m^{dc}$, m, $\phi$ found by LSQ analysis for this position. A similar fit is performed for the remaining 100 interference signals.

Figure 16B:
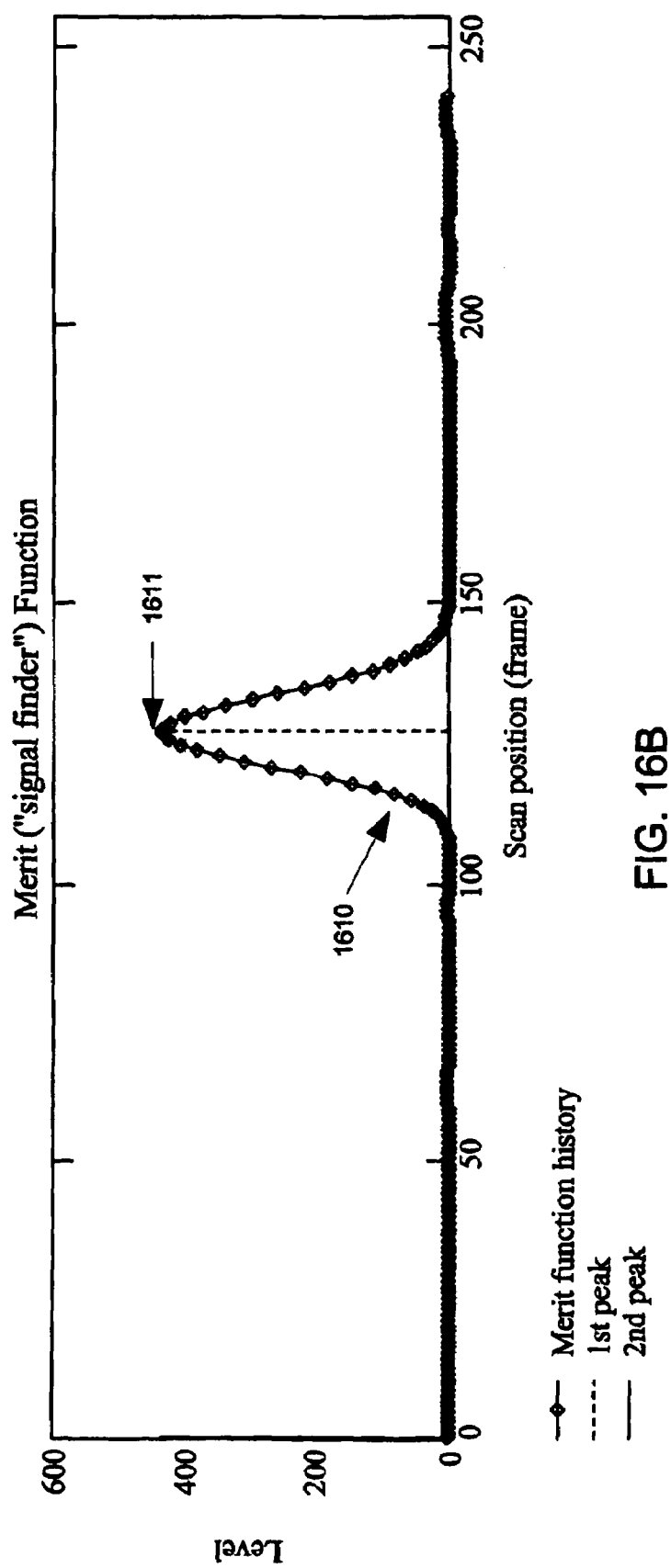
FIG. 16b is a plot of the merit function obtained from the LSQ pattern matching analysis of measurement signal 1201.

Referring to FIG. 16b the magnitude-based merit function 1610 $\Pi^m$ of Eq. (27) for the LSQ fit is plotted as a function of scan position. The peak value 1611 is identified with the top-surface reflection. As this is a solid surface example, there is no second peak.

Figure 17B:
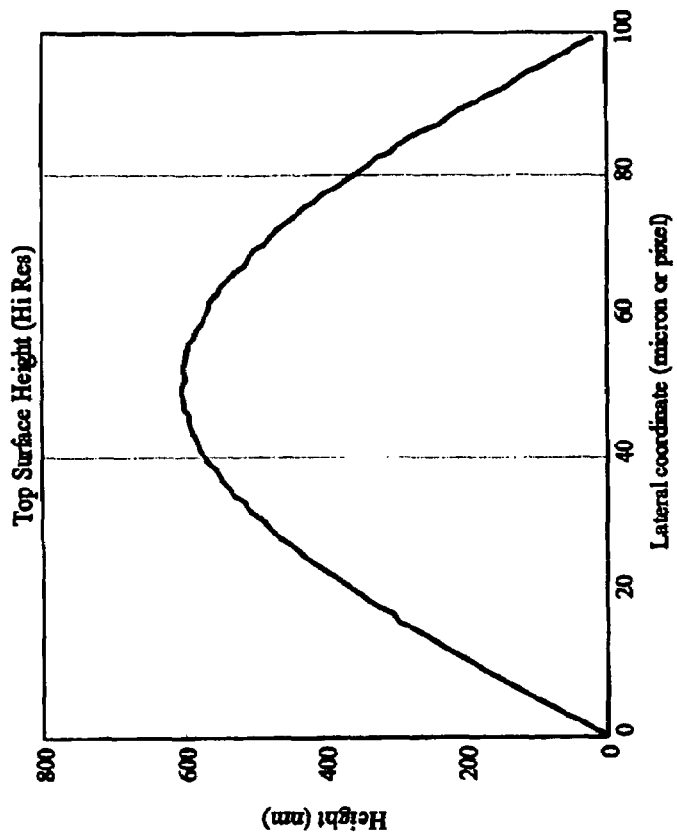
FIG. 17b is a plot of the high resolution top surface height profile obtained from the LSQ pattern matching analysis of measurement signal 1201.
Figure 17A:
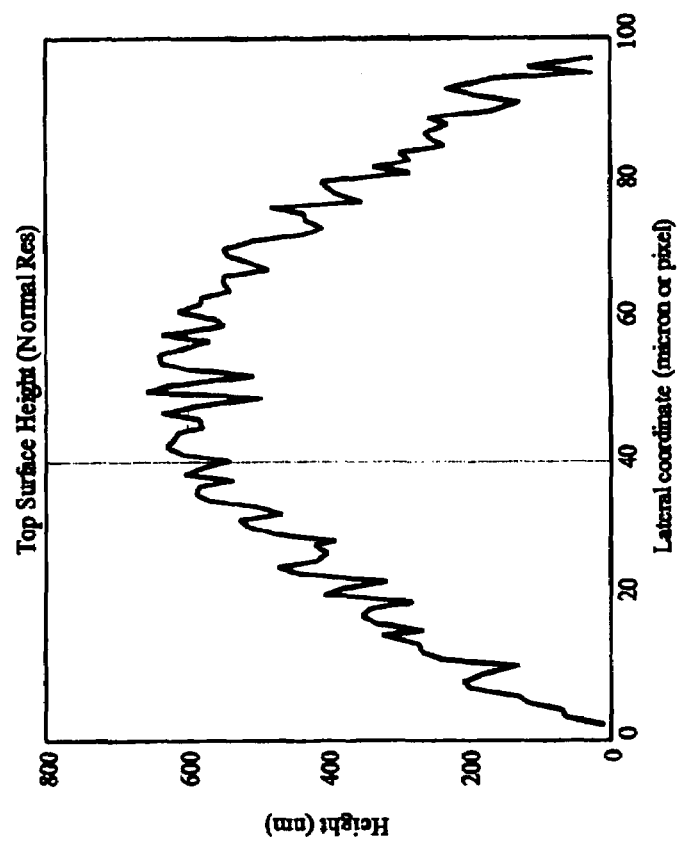
FIG. 17a is a plot of the normal resolution top surface height profile obtained from the LSQ pattern matching analysis of measurement signal 1201.

Referring to FIGS. 17a and 17b, the surface height of the measurement object is shown as a function of lateral position across the object surface as determined from the model signal 1501 and 101 interference signals. FIG. 17a shows a surface height profile using a normal resolution (LSQ-Norm) height calculation. FIG. 17b shows a surface height profile using a high resolution (LSQ-High) height calculation.

2. Determining a Surface Height Profile of a Multiple-Surface Measurement Object (Simulated Data)

Simulated interference signals are obtained from 101 points in a linear scan across an object composed of a layer of silicon dioxide on a silicon substrate. The film thickness ranges from 1000 nm at edges to 1600 nm in the middle. The top surface has an approximately spherical profile with PV=600 nm. The interferometer system uses an irradiation wavelength of 550 nm with a bandwidth of 100 nm. The bandwidth is Gaussian in wavenumber. The numerical aperture of the system is 0.01 for normal incidence, collimated light. Each interference signal has a full scale digital resolution of 256 grey scale steps. The average signal strength is 20 grey levels amplitude AC above 80 grey levels DC. The signals have random noise having a standard deviation of 2 grey levels. Unlike the previous example, this is a multiple surface example with film structure. Thus an asymmetric model signal and the LSQ fit based merit function of Eq.(28) will be used to obtain a surface height profile.

Figure 18:
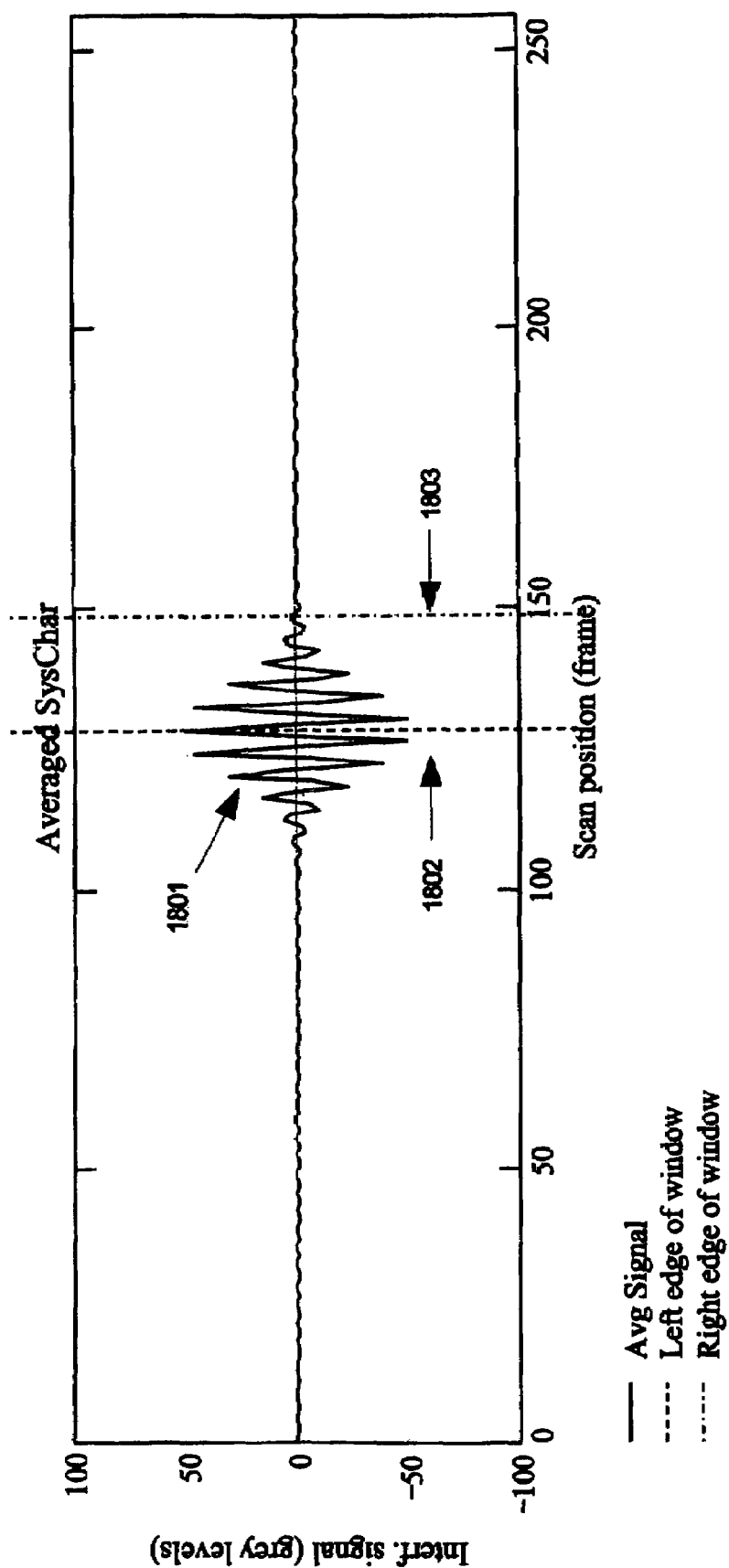
FIG. 18 is a plot of averaged system characterization data from example 2.

Referring to FIG. 18, averaged system characterization intensity data 1801 from which the model signal $\tilde{T}$ is extracted is shown in the scan position domain. The boundaries of the window 1802, 1803 are also shown. Note that only the right-hand or leading-edge portion of the signal is retained within the window. This will provide an asymmetric model function.

Figure 19B:
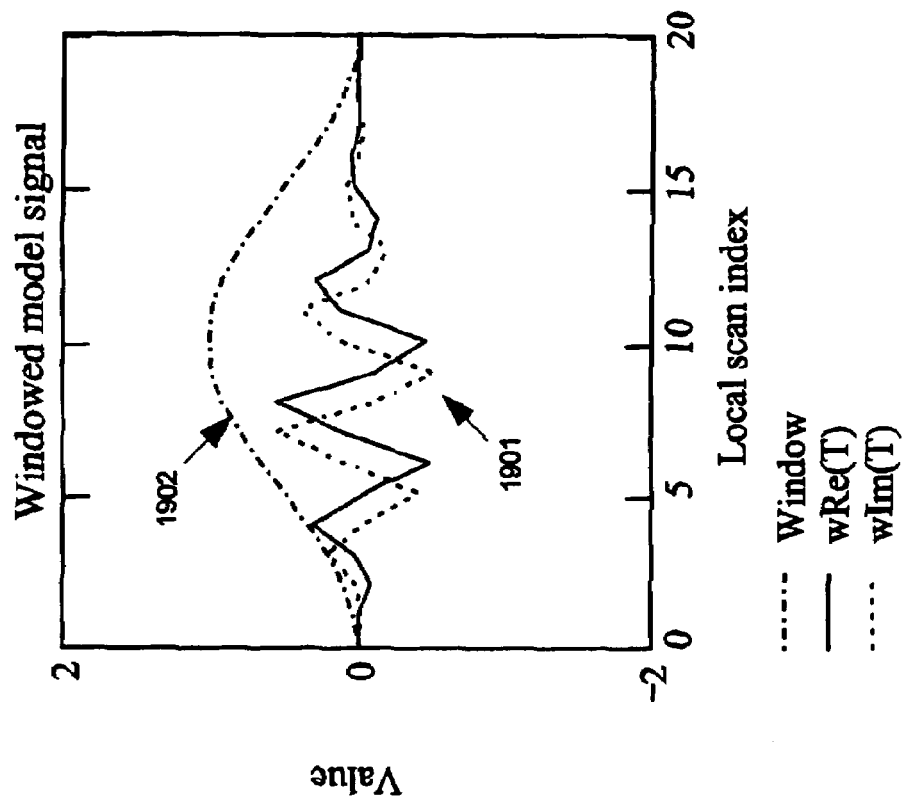
FIG. 19b is a plot of the windowed asymmetric model signal for use in the sliding windows LSQ pattern matching analysis described in example 2.
Figure 19A:
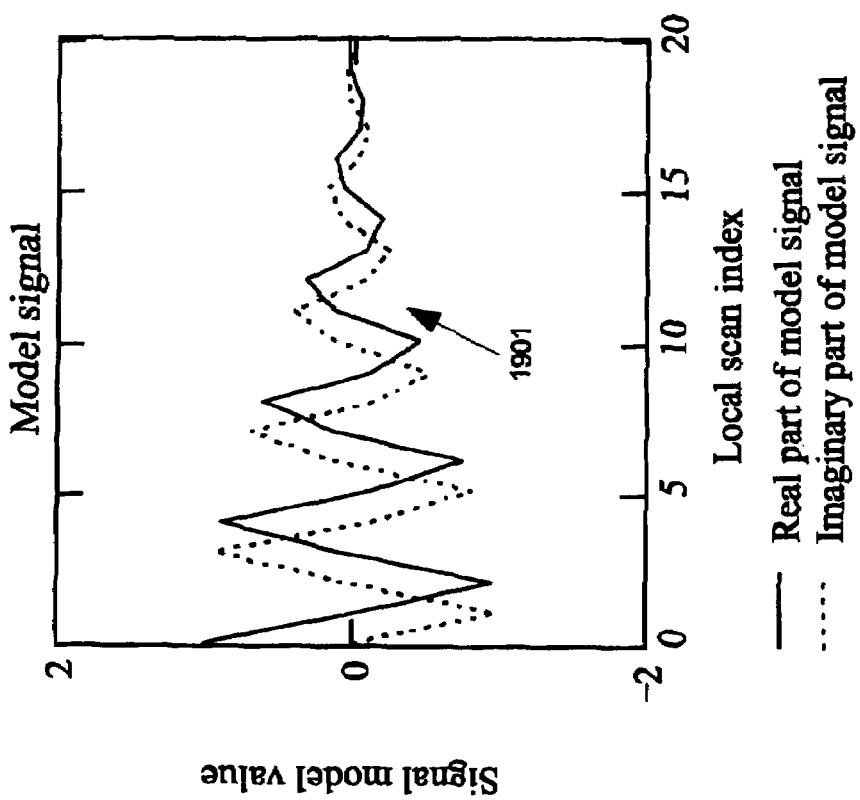
FIG. 19a is a plot of the asymmetric model signal for use in the sliding windows LSQ pattern matching analysis described in example 2.

Referring to FIG. 19a, asymmetric model signal $\tilde{T}$ 1901 is shown. FIG. 19b shows model signal $\tilde{T}$ 1901 multiplied by a window function 1902.

Figure 20A:
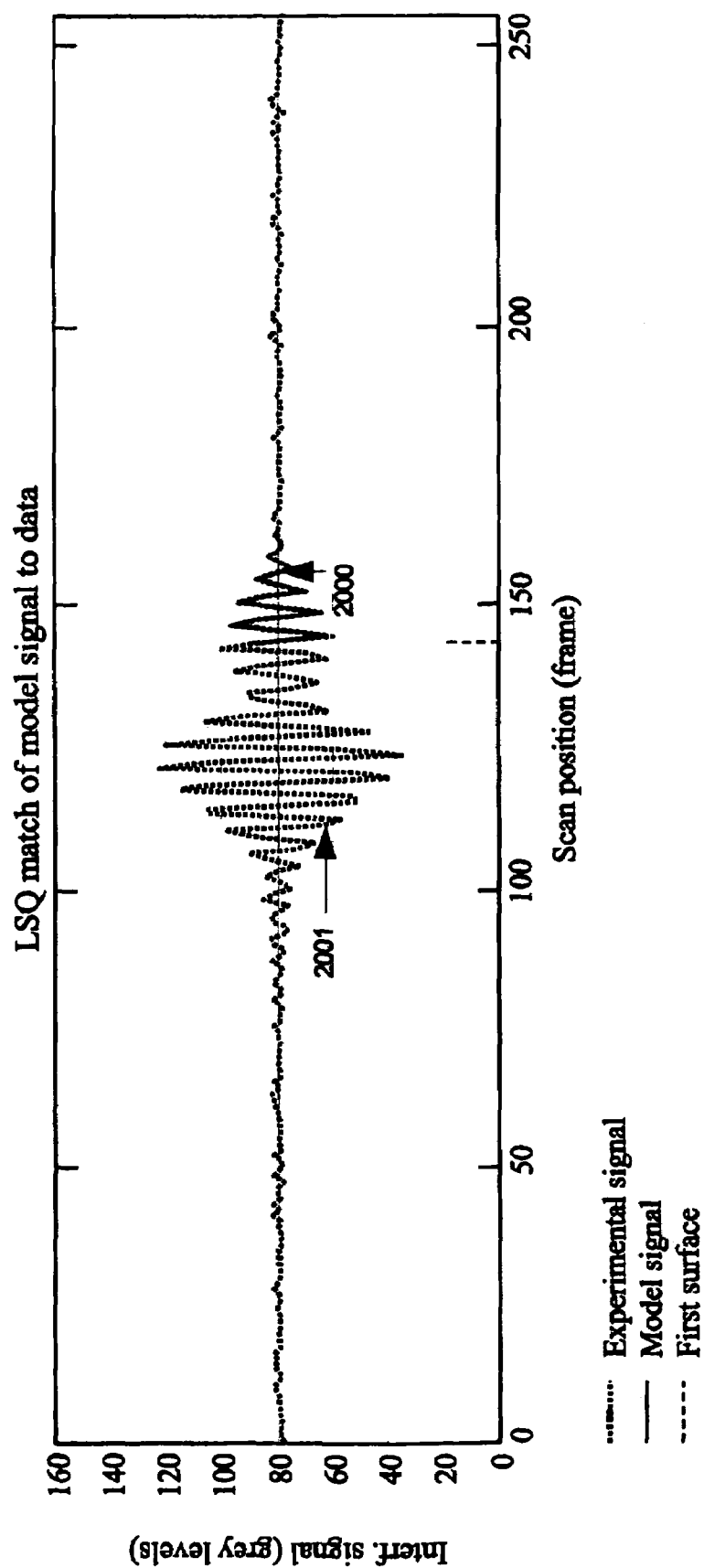
FIG. 20a is a plot showing the result of the LSQ pattern matching analysis described in example 2.

Referring to FIG. 20a, the model signal 2000 has been fit to the simulated data set 2001 using the sliding window LSQ technique. The model signal is shown at the best fit camera frame $z^{best}$, after applying the parameters $m^{dc}$, m, $\phi$ found by LSQ analysis for this position. A similar fit is performed for the remaining 100 interference signals.

Figure 20B:
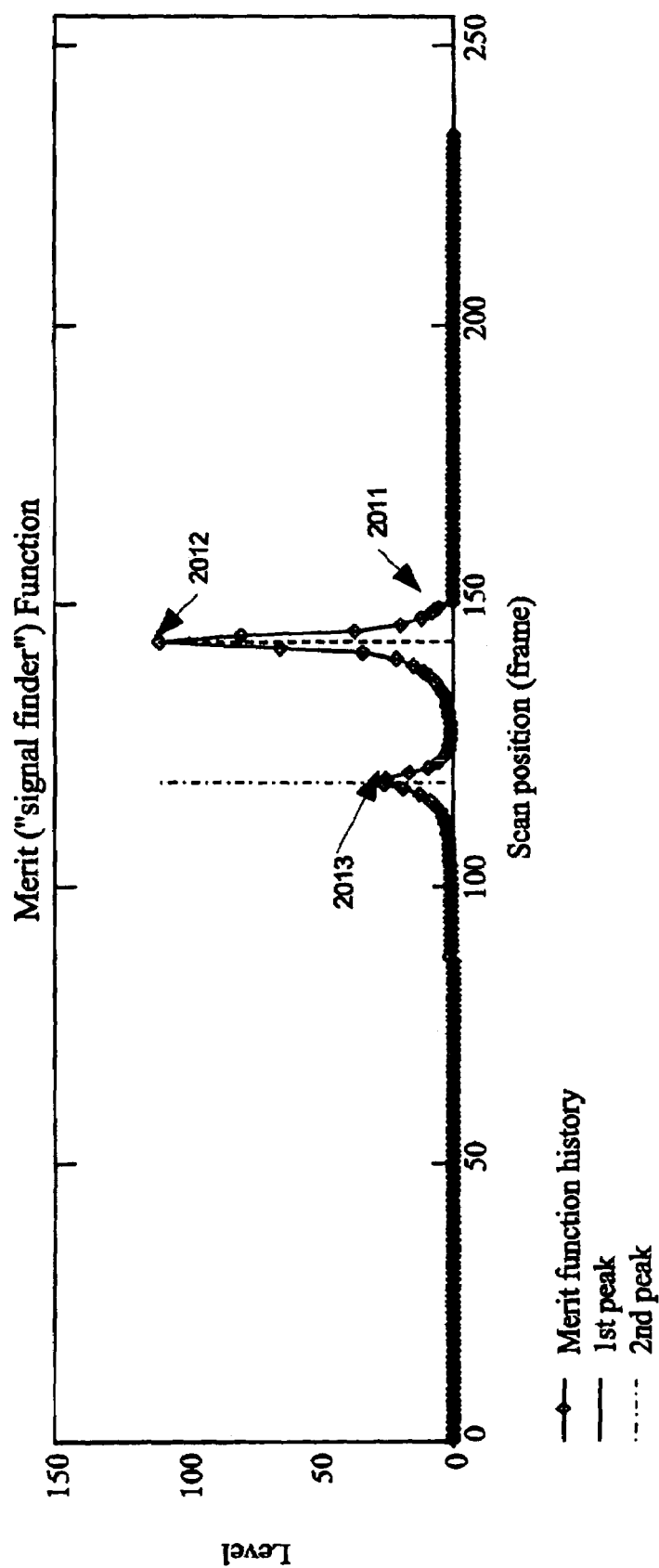
FIG. 20b is a plot of the merit function obtained from the LSQ pattern matching analysis described in example 2.

Referring to FIG. 20b the fit-based merit function 2011 $\Pi^x$ of Eq. (28) for the LSQ fit is plotted as a function of scan position. The peak value 2012 is identified with the top-surface reflection. Note that the left-hand peak 2013 corresponding to the second surface is shorter than the first peak, even though the signal strength is greater at this position, because the fit is better at the leading edge.

Figure 21B:
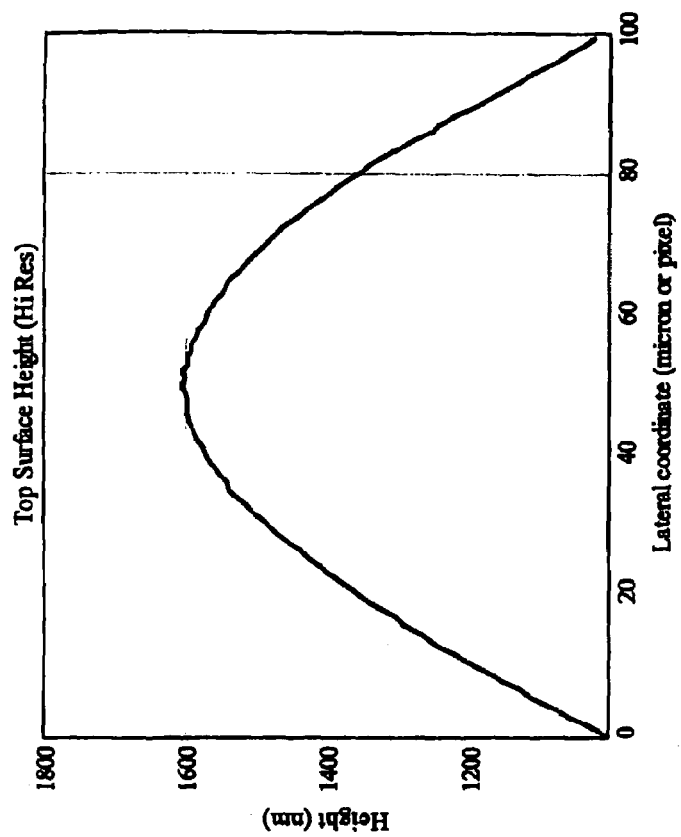
FIG. 21b is a plot of the high resolution top surface height profile obtained from the LSQ pattern matching analysis described in example 2.
Figure 21A:
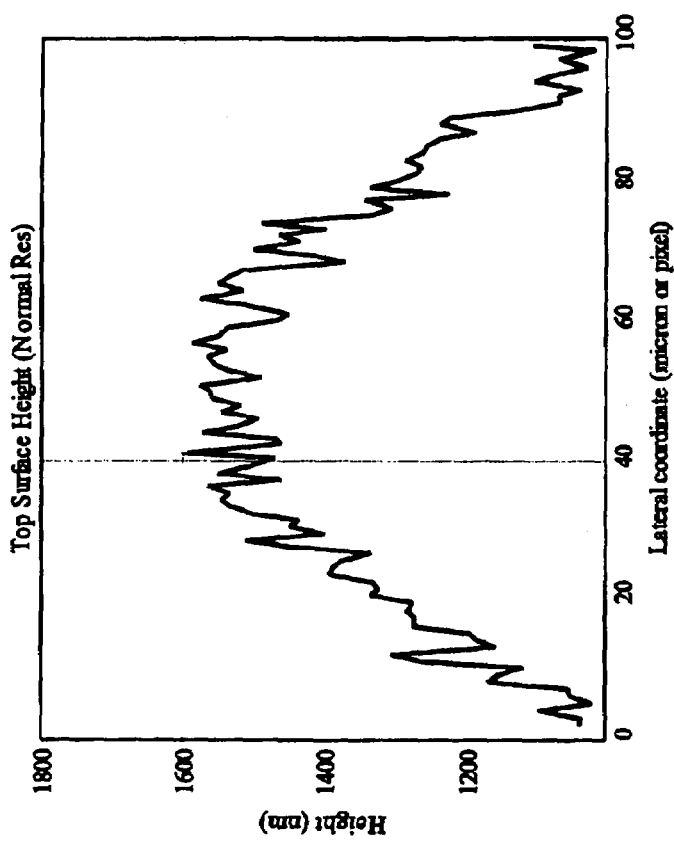
FIG. 21a is a plot of the normal resolution top surface height profile obtained from the LSQ pattern matching analysis described in example 2.

Referring to FIGS. 21a and 21b, the surface height of the measurement object is shown as a function of lateral position across the object surface as determined from the model signal 1501 and 101 interference signals. FIG. 21a shows a surface height profile using a normal resolution (LSQ-Norm) height calculation. FIG. 21b shows a surface height profile using a high resolution (LSQ-High) height calculation.

3. Determining a Surface Height Profile of a Multiple-Surface Thin Film Measurement Object (Simulated)

Simulated interference signal data are obtained from 101 points in a linear scan across an object composed of a layer of silicon dioxide on a silicon substrate. The film thickness increases from 0 nm at the left edge to 2500 nm at the right edge in increments of 25 nm. The top surface is flat. The interferometer system uses an irradiation wavelength of 550 nm with a bandwidth of 100 nm. The bandwidth is Gaussian in wavenumber. The numerical aperture of the system is 0.01 for normal incidence, collimated light. Each interference signal has a full scale digital resolution of 256 grey scale steps. The average signal strength is 20 grey levels amplitude AC above 80 grey levels DC. The signals have random noise having a standard deviation of 2 grey levels. As in the previous example, this is a multiple surface example with film structure. Thus an asymmetric model signal and the LSQ fit based merit function of Eq.(28) will be used to obtain a surface height profile.

Figure 22A:
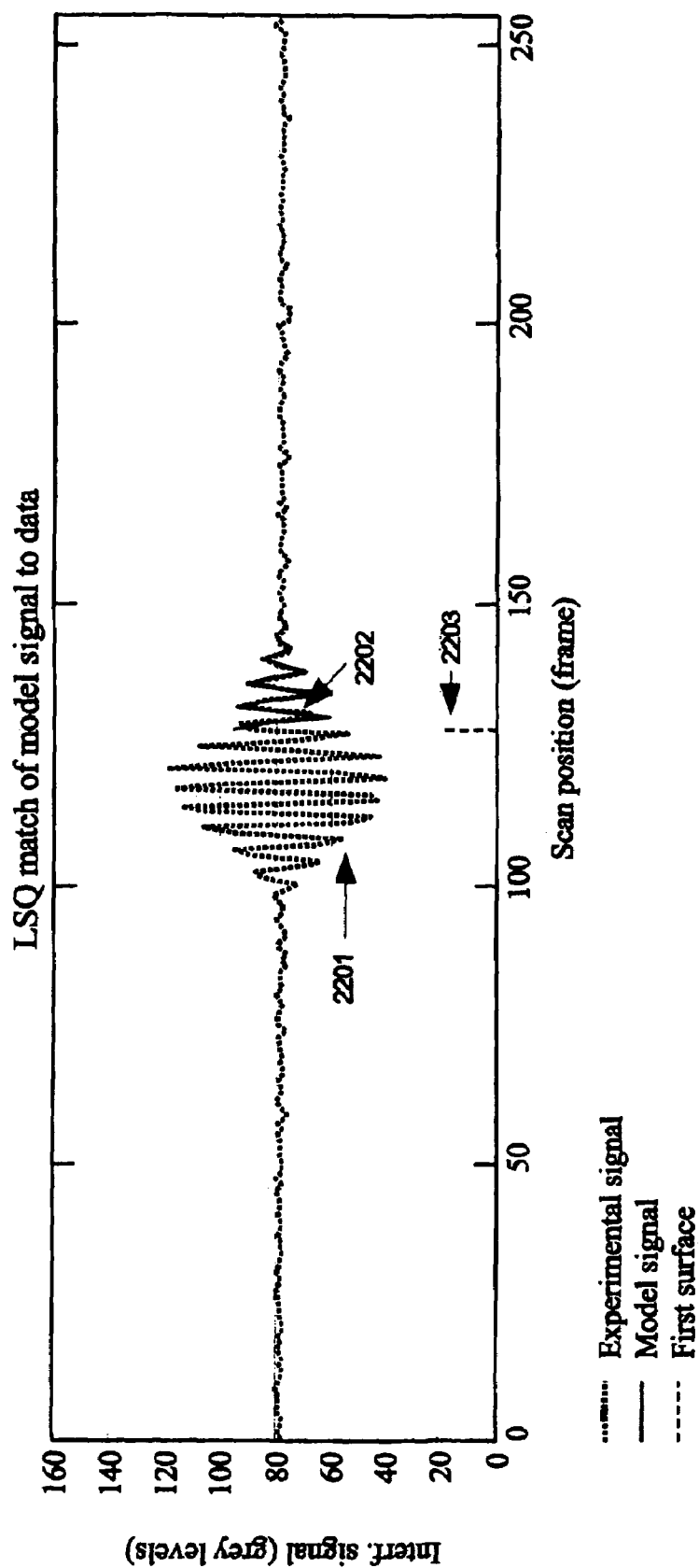
FIG. 22a is a plot showing the result of the LSQ pattern matching analysis described in example 3.

Referring to FIG. 22a, the model signal has been fit to the simulated interferometer signal data 2201 using the sliding window LSQ technique. The model 2202 signal is shown at the best fit camera frame 2203 $z^{best}$, after applying the parameters $m^{dc}$, m, $\phi$ found by LSQ analysis for this position. Note that the two surface signals are not separable by signal strength, yet the sliding window LSQ technique correctly identifies the leading edge.

Figure 22B:
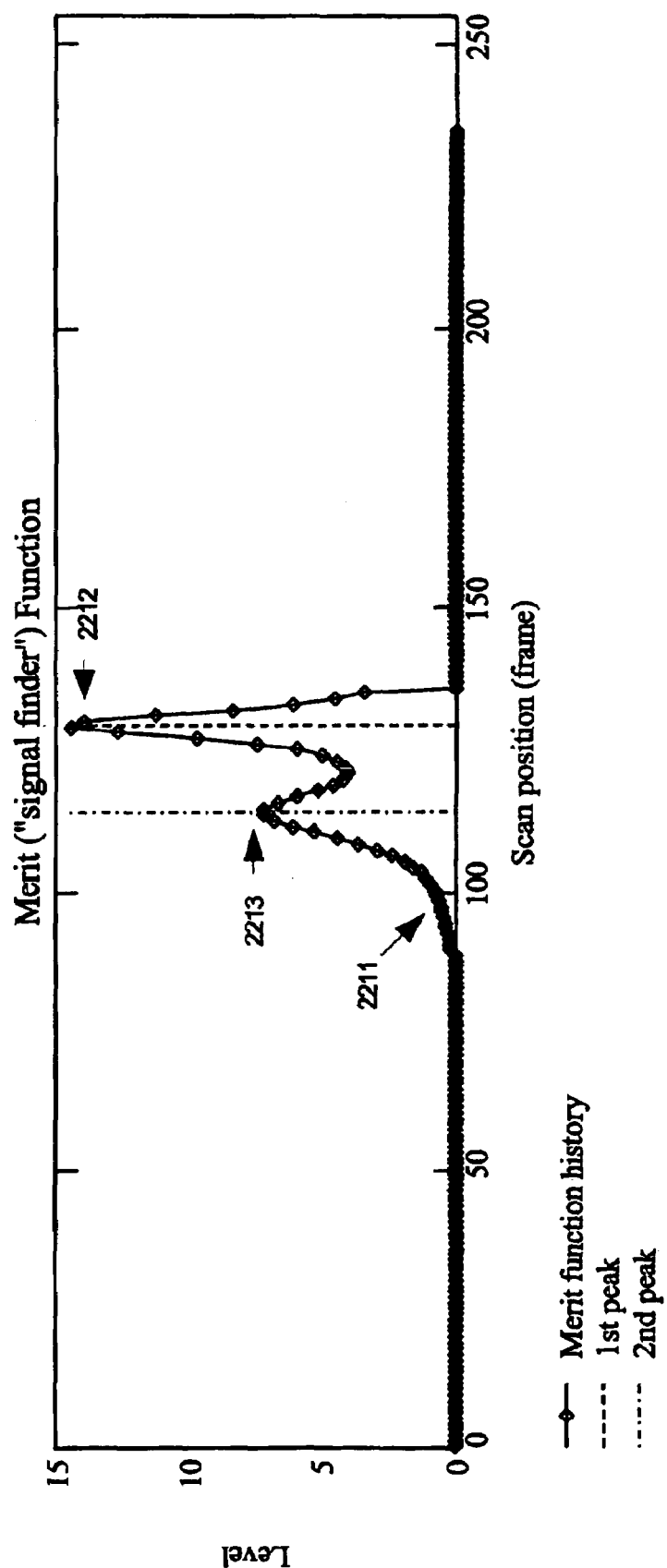
FIG. 22b is a plot of the merit function obtained from the LSQ pattern matching analysis described in example 3.

Referring to FIG. 22b the fit-based merit function 2211 $\Pi^{\chi}$ of Eq. (28) for the LSQ fit is plotted as a function of scan position. The peak value 2212 is identified with the top-surface reflection. Note that a left-hand peak 2213 for the second surface is present, even though the two signals seem inseparable.

Figure 23:
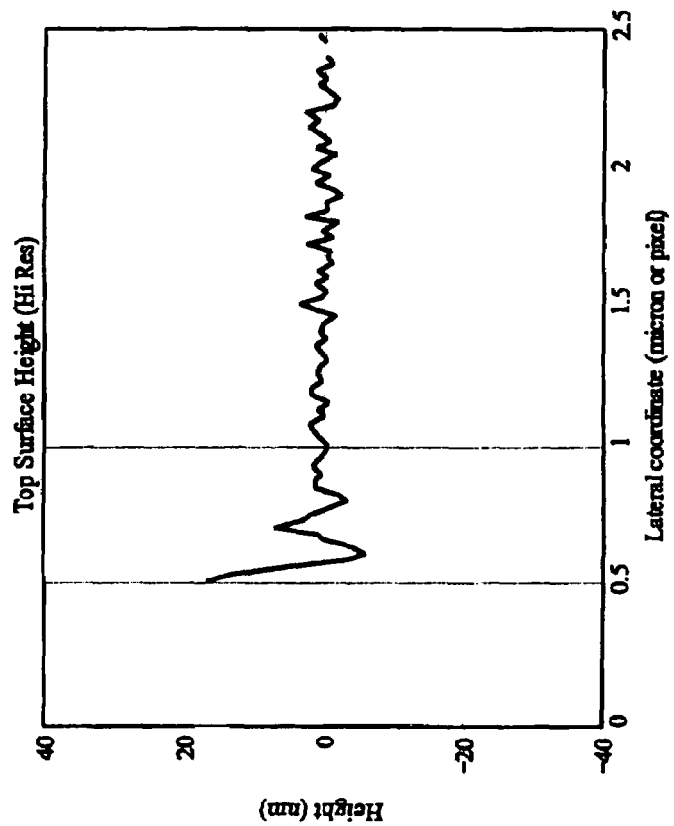
FIG. 23a is a plot of the normal resolution top surface height profile obtained from the LSQ pattern matching analysis described in example 3.
FIG. 23b is a plot of the high resolution top surface height profile obtained from the LSQ pattern matching analysis described in example 3.
Figure 23A:
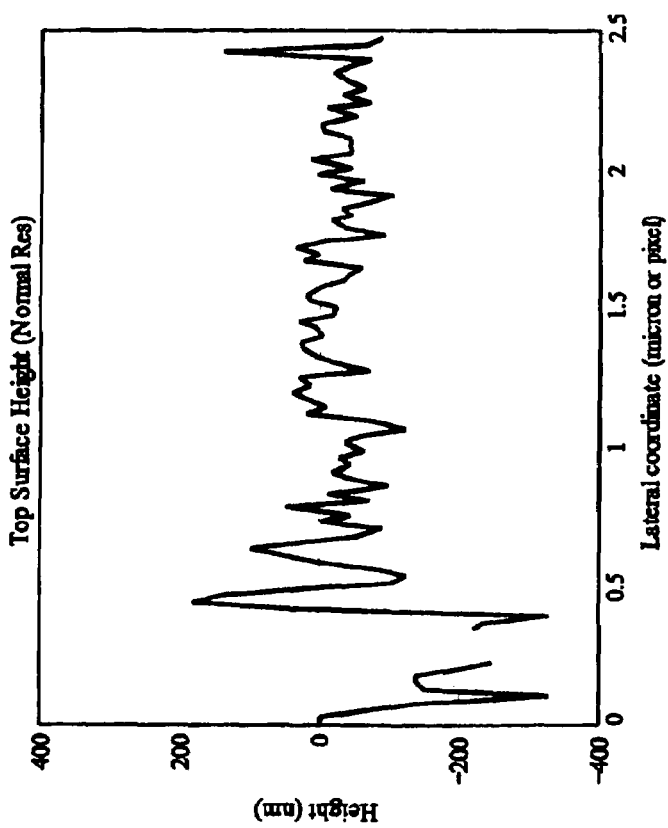

Referring to FIGS. 23a and 23b, the surface height of the measurement object is shown as a function of lateral position across the object surface as determined from the model signal 1501 and 101 interference signals. FIG. 21a shows a surface height profile using a normal resolution (LSQ-Norm) height calculation. FIG. 21b shows a surface height profile using a high resolution (LSQ-High) height calculation. The lateral coordinate is the film thickness in microns. Recall that the surface height profile of the measurement object is flat, so that the ideal result would be a horizontal line at zero. The best results are obtained for 0.7 microns and above; and reasonably correct results are obtained for film thickness down to 0.5 microns. This compares favorably with the 1.0-micron failure point of dot product based techniques.

4. Determining a Surface Height Profile of a Multiple-Surface Measurement Object (Real Data)

Figure 24:
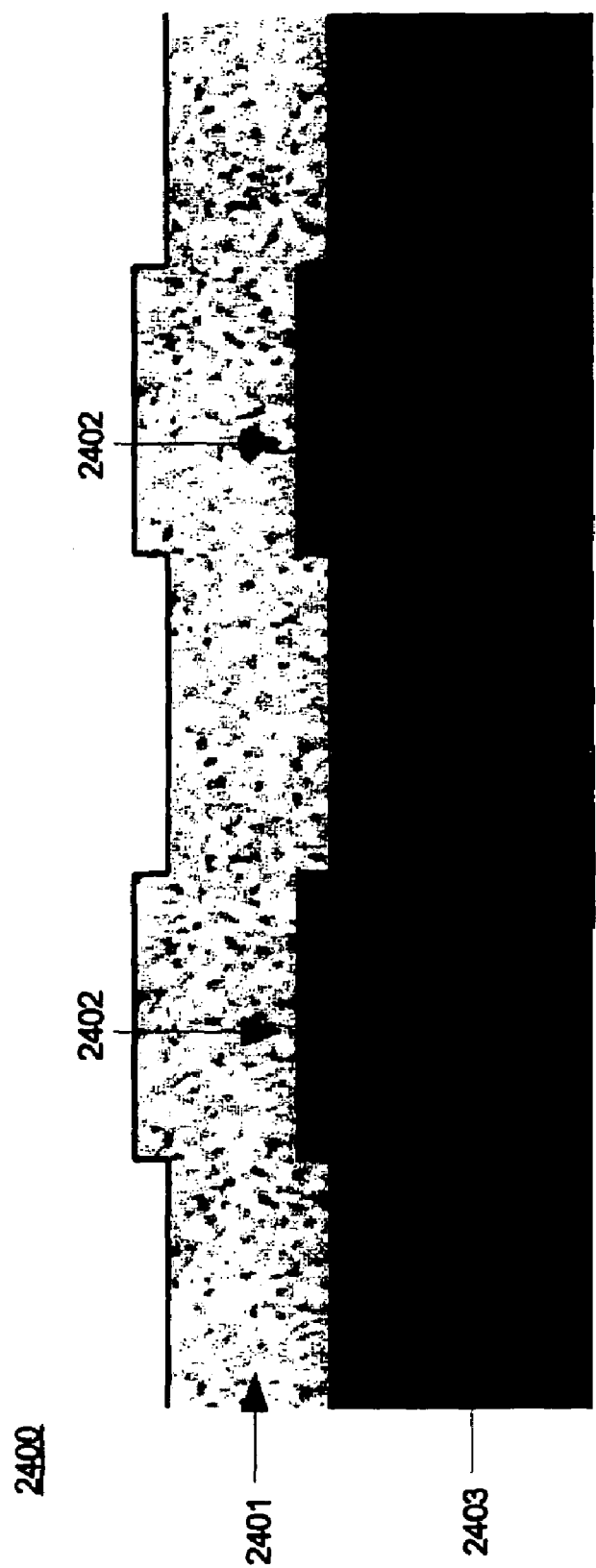
FIG. 24 is a schematic diagram of measurement object 2400 composed of a 600 nm think layer of conformal photoresist 2401 over a pair of square aluminum pads 2402 on a silicon substrate 2403.

Interference signal data are obtained in a linear scan across a measurement object 2400. Referring to FIG. 24, the measurement object 2400 is composed of a 600 nm think layer of conformal photoresist 2401 over a pair of square aluminum pads 2402 on a silicon substrate 2403. As in the previous example, this is a multiple surface example with film structure. Thus an asymmetric model signal and the LSQ fit based merit function of Eq.(28) will be used to obtain a surface height profile.

Figure 24A:
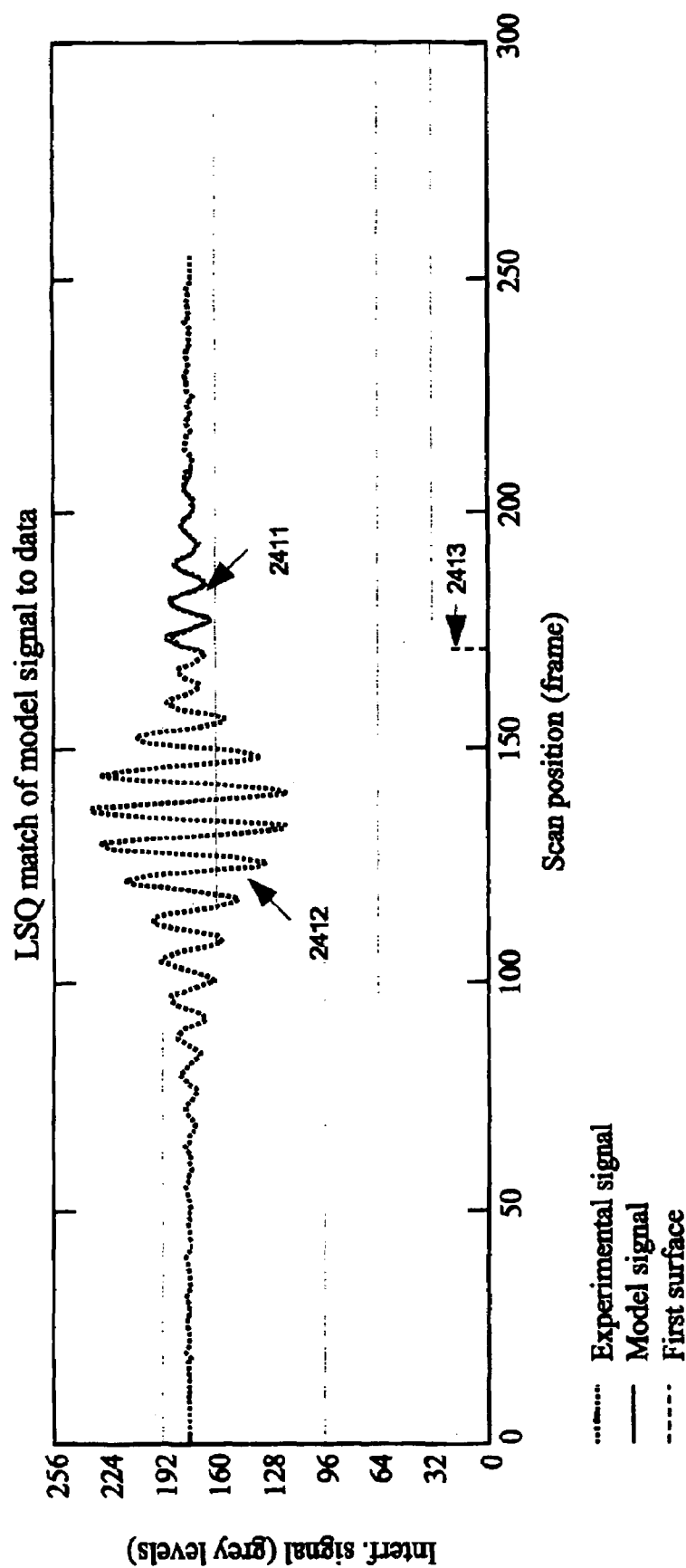
FIG. 24a is a plot showing the result of the LSQ pattern matching analysis of the SWLI signal from a point on measurement object 2400.
Figure 25B:
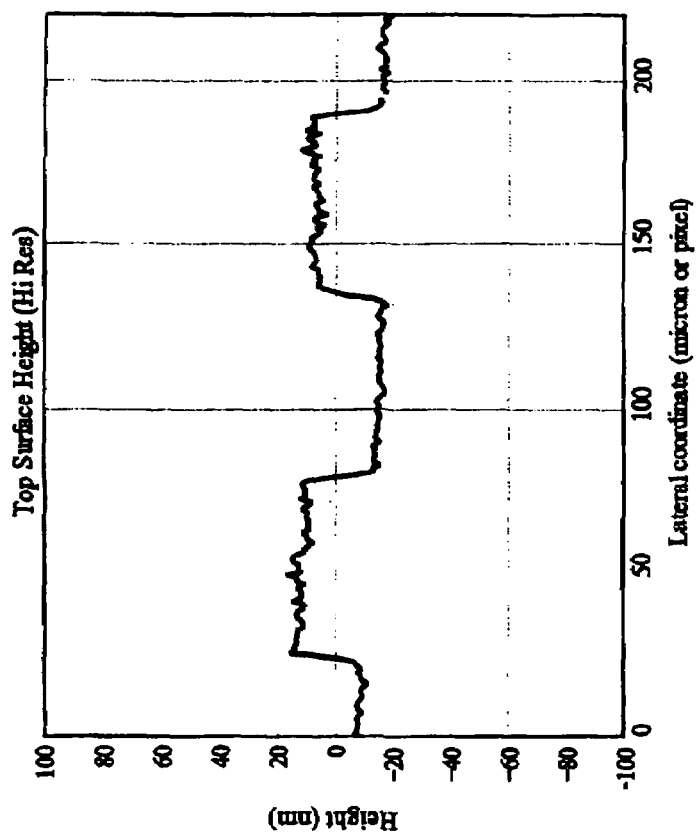
FIG. 25b is a plot of the high resolution top surface height profile obtained from the LSQ pattern matching analysis of a SWLI signal from measurement object 2400.
Figure 25A:
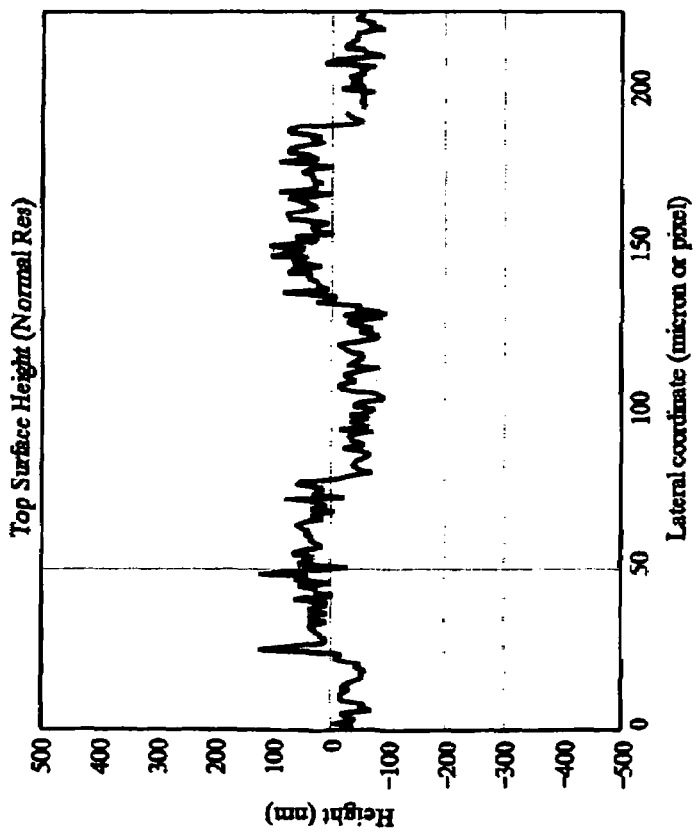
FIG. 25a is a plot of the normal resolution top surface height profile obtained from the LSQ pattern matching analysis of the SWLI signal from measurement object 2600.

Referring to FIG. 24a, the model signal 2411 has been fit to the interferometer signal data 2412 using the sliding window LSQ technique. The model signal 2411 is shown at the best fit camera frame 2413 $z^{best}$, after applying the parameters $m^{dc}$, m, $\phi$ found by LSQ analysis for this position. Note the first-surface signal is difficult to identify because of the weakness of the signal and the distortion caused by the overlap of the first- and second-surface signals. The sliding window LSQ technique with an asymmetric model signal identifies the right-hand portion of the first surface signal, where the data are relatively undistorted by the second surface Referring to FIGS. 25a and 25b, the surface height of the measurement object is shown as a function of lateral position across the object. FIG. 25a shows a surface height profile using a normal resolution (LSQ-Norm) height calculation. FIG. 25b shows a surface height profile using a high resolution (LSQ-High) height calculation. The higher areas correspond to measurements over the Al pads.

5. Determining a Surface Height Profile of a Multiple-Surface Measurement Object (Real Data)

Figure 26:
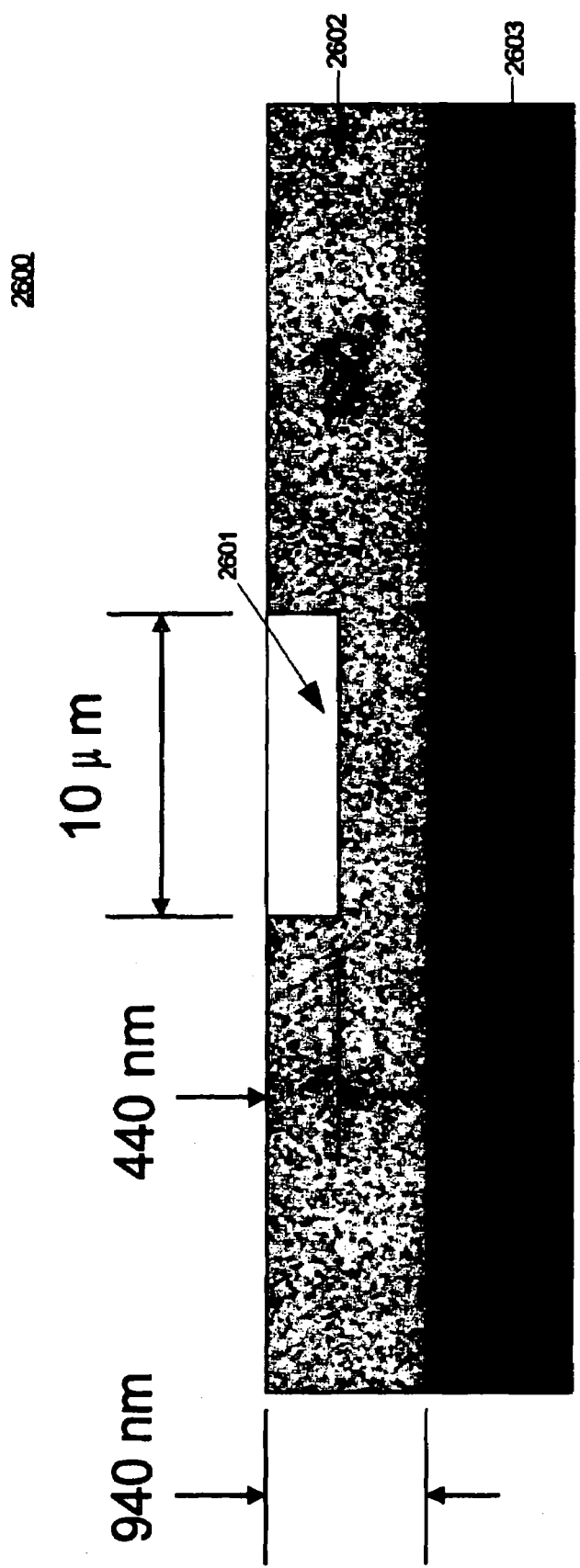
FIG. 26 is a schematic diagram of measurement object 2600 which features a 10-micron wide, 440-nm deep trench 2601 in a nominal 940-nm thickness of silicon dioxide 2602 on a silicon substrate 2603.

Interference signal data are obtained in a linear scan across a measurement object 2600. Referring to FIG. 26, the measurement object 2600 features a 10-micron wide, 440-nm deep trench 2601 in a nominal 940-nm thickness of silicon dioxide 2602 on a silicon substrate 2603. As in the previous example, this is a multiple surface example with film structure. Thus an asymmetric model signal and the LSQ fit based merit function of Eq.(28) will be used to obtain a surface height profile.

Figure 27:
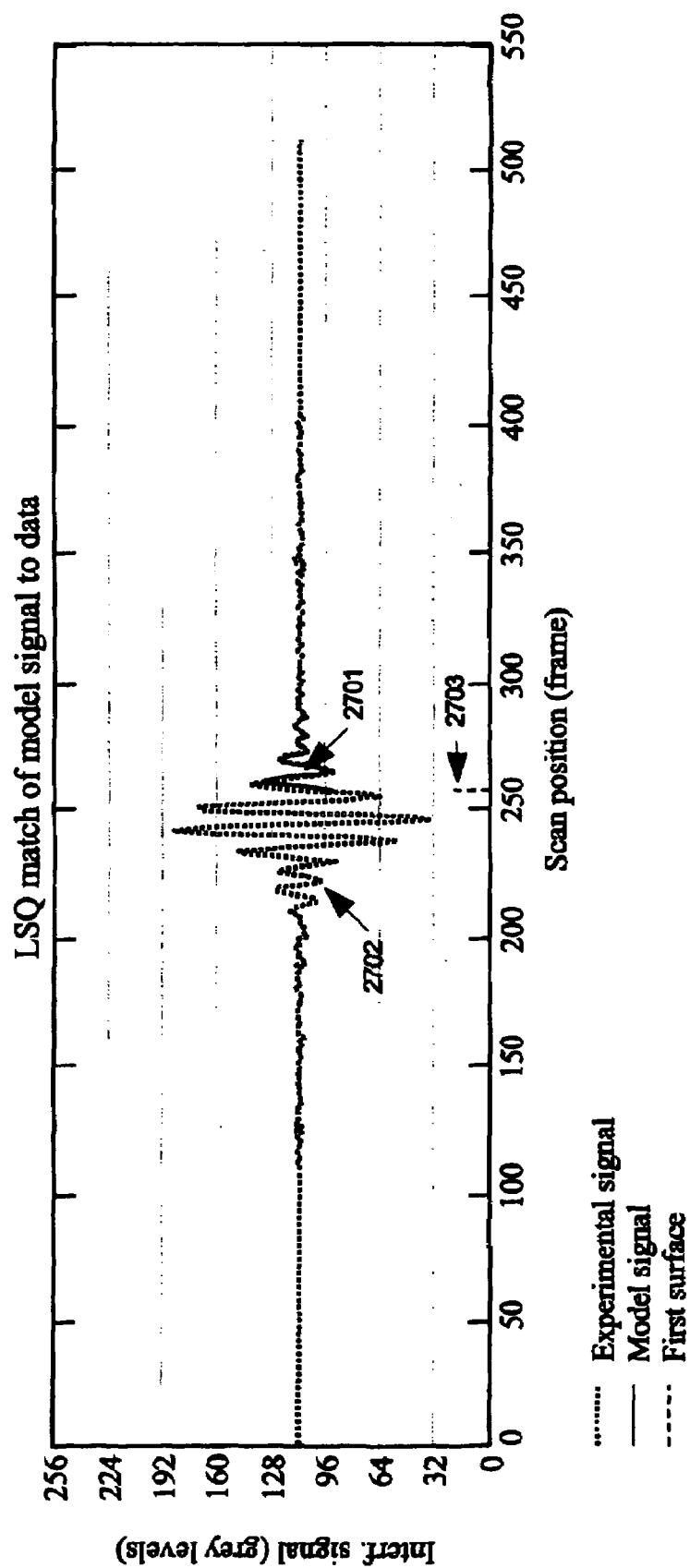
FIG. 27 is a plot showing the result of the LSQ pattern matching analysis of the SWLI signal from a point on measurement object 2600.

Referring to FIG. 27, the model signal 2701 has been fit to the interferometer signal data 2702 using the sliding window LSQ technique. The model signal 2701 is shown at the best fit camera frame 2703 $z^{best}$, after applying the parameters $m^{dc}$, m, $\phi$ found by LSQ analysis for this position. Note that the two surface signals are not separable by signal strength, yet the sliding window LSQ technique correctly identifies the leading edge.

Figure 28B:
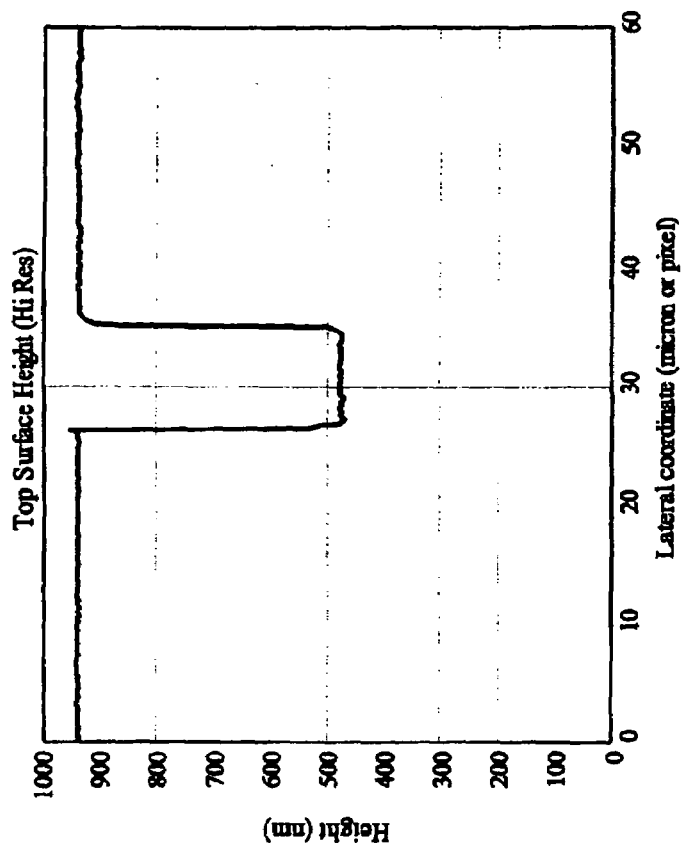
FIG. 28b is a plot of the high resolution top surface height profile obtained from the LSQ pattern matching analysis of the SWLI signal from measurement object 2600.
Figure 28A:
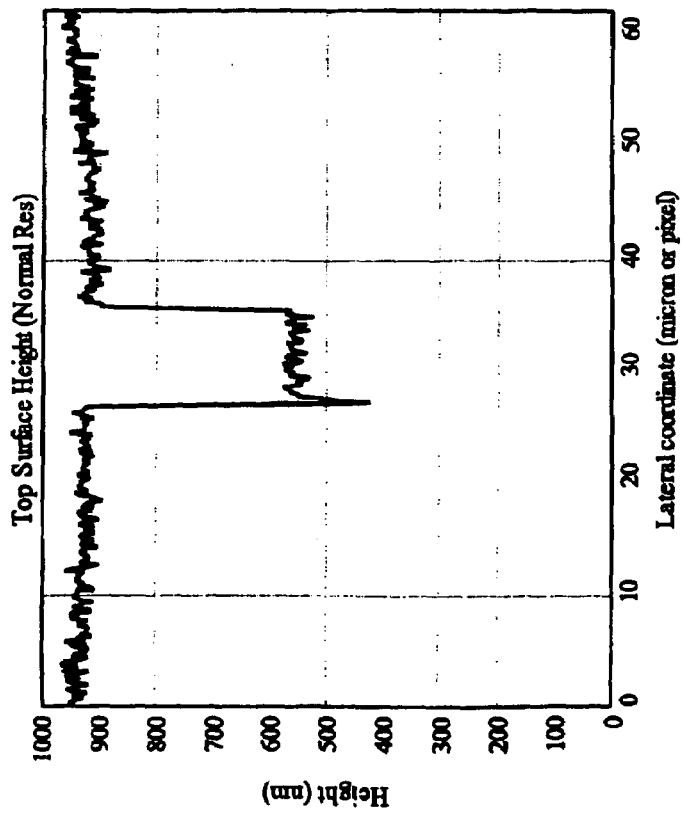
FIG. 28a is a plot of the normal resolution top surface height profile obtained from the LSQ pattern matching analysis of the SWLI signal from measurement object 2600.

Referring to FIGS. 28a and 28b, the surface height of the measurement object is shown as a function of lateral position across the object. FIG. 28a shows a surface height profile using a normal resolution (LSQ-Norm) height calculation. FIG. 28b shows a surface height profile using a high resolution (LSQ-High) height calculation. The profiles have been offset in height so that the areas outside the trench are 940 nm high. The trench measures 460 nm deep with respect to the top surface, and 480 nm thick with respect to the supposed substrate position based on an assumed thickness of 940 nm outside the trench.

Extensions: Compensation for Scan Errors and Vibration

In further embodiments, the system and method can modified to accommodate arbitrary scan increments, unlike conventional PSI, which requires a constant-velocity scan. For example, one can implement a conventional scanning interferometer with a low-cost distance measuring interferometer (DMI), or some other technique, to monitor true scanning motion, together with software correction using an LSQ technique.

The extension of the sliding-window LSQ method to known unequal scans involves some changes to the algorithm. The principal difference is that there must be a different model signal $\tilde{T}$ for every scan index z, and consequently, there must also be a different fit matrix $\Xi$ at each position. The correct model signal $\tilde{T}$ follows from the DFT of Eq.(13) when one includes the known scan errors. These now z-dependent vectors $\tilde{T}$ and matrices $\Xi$ are calculated in advance, so there is no impact on processing time. The calculations of Eq.(21) are complicated somewhat by having to keep track of the correct index for $\tilde{T}$ and $\Xi$ at each scan position, but there are no extra multiplies or other operations to perform. With this straightforward modification, we can compensate for any arbitrary scan error.

Computer Program

Any of the computer analysis methods described above can be implemented in hardware or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

Embodiments relate to interferometry systems and methods for determining information about a test object. Additional information about suitable low-coherence interferometry systems, electronic processing systems, software, and related processing algorithms is disclosed in commonly owed U.S. Patent Applications published as US-2005-0078318-A1 entitled "METHODS AND SYSTEMS FOR INTERFEROMETRIC ANALYSIS OF SURFACES AND RELATED APPLICATIONS," US-2004-0189999-A1 entitled "PROFILING COMPLEX SURFACE STRUCTURES USING SCANNING INTERFEROMETRY," and US-2004-0085544-A1 entitled "INTERFEROMETRY METHOD FOR ELLIPSOMETRY, REFLECTOMETRY, AND SCATTEROMETRY MEASUREMENTS, INCLUDING CHARACTERIZATION OF THIN FILM STRUCTURES," the contents of which are incorporated herein by reference.

A number of embodiments of the invention have been described. Nevertheless, it will be understood that various modifications may be made without departing from the spirit and scope of the invention.

What is claimed is:

1. A method comprising:
providing a scanning interferometry signal produced by a scanning interferometer for a first location of a test object;
providing a model function of the scanning interferometry signal produced by the scanning interferometer, wherein the model function is parametrized by one or more parameter values;
fitting the model function to the scanning interferometry signal for each of a series of shifts in scan position between the model function and the scanning interferometry signal by varying the parameter values; and
determining information about the test object at the first location based on the fitting.

2. The method of claim 1, further comprising:
providing a scanning interferometry signal produced by the scanning interferometer for each of additional locations of the test object;
fitting the model function to each of the scanning interferometry signals corresponding to the additional locations of the test object for each of a series of shifts in scan positions between the model function and the respective scanning interferometry signal by varying the parameter values; and
determining information about the test object at the additional locations based on the additional fitting.

3. The method of claim 2, wherein the interferometry signal for each location of the test object is expressible as comprising an intensity value for each of a series of global scan positions of the scanning interferometer.

4. The method of claim 3, wherein the model function is expressible as comprising an intensity value for each of a series of local scan positions, and wherein the fitting comprises fitting the model function to each of the interferometry signals with the model function centered on each of the global scan positions corresponding to the series of shifts in scan position between the model function and the respective scanning interferometry signal by varying the parameter values.

5. The method of claim 4, wherein, for each of the locations of the test object, the fitting comprises determining which of the series of shifts in scan positions between the model function and the respective scanning interferometry signal produces an optimum fit.

6. The method of claim 5, wherein the determining information comprises determining a surface height profile for the test object based on the shift in scan position corresponding to the optimum fit for each of the locations.

7. The method of claim 5, wherein the test object comprises a thin film, and wherein the determining information comprises determining a thickness profile for the thin film based on the shift in scan position corresponding to the optimum fit for each of the locations.

8. The method of claim 5, wherein the determining which of the series of shifts in scan positions produces the optimum fit comprises comparing the model function and the respective interferometry signal to determine the degree of similarity between the model function and the respective interferometry signal.

9. The method of claim 8, wherein determining which of the series of shifts in scan positions produces the optimum fit comprises calculating a metric indicative of the degree of similarity between the model function and the respective interferometry signal.

10. The method of claim 9, wherein determining which of the series of shifts in scan positions produces the optimum fit comprises determining a shift in scan position for which the corresponding metric indicates a high degree of similarity between the model function and the respective interferometry signal.

11. The method of claim 9, wherein, for each of the locations on the test object, the metric is related to a sum $$\sum_{z=0}^{N} g(I_z, f_z)$$

where $I_z$ is the intensity value of the interferometer signal at the $z^{th}$ member of the set of global scan positions, $f_z$ is the intensity value of the model function at the $z^{th}$ member of the set of global scan positions, and g is some function which depends on $I_z$ and $f_z$.

12. The method of claim 11 wherein the metric is related to the sum of the squares of the differences between the intensity value of the model function and the intensity value of the interferometer signal at each of the series of global scan positions.

13. The method of claim 11 wherein and the metric is related to the absolute value of the difference between the intensity value of the model function and the intensity value of the interferometer signal at each of the series of global scan positions.

14. The method of claim 9, wherein the metric is additionally based on the magnitude of the model function.

15. The method of claim 4,
wherein the test object comprises a thin film;
wherein the fitting comprises, for each of the locations, determining a first shift of the series of shifts of scan position which corresponds to a first optimal fit and determining a second shift of the series of shifts of scan position which corresponds to a second optimal fit; and
wherein the determining information comprises determining a thickness profile for the thin film based on the first and second shifts in scan position for each of the locations.

16. The method of claim 5, wherein, for each of the locations, the fitting further comprises determining an estimate for one or more the parameter values based on the optimum fit.

17. The method of claim 16, wherein the determining of the information about the test object is based on the shift in scan position and at least one of the parameter value estimates corresponding to the optimum fit for each of the locations.

18. The method of claim 1, wherein the parameter values comprise a phase value, an average magnitude value, and an offset value.

19. The method of claim 2, wherein, for each of the locations, the fitting comprises determining an estimate for one or more the parameter values based on an optimum fit of the model function to the respective interferometry signal.

20. The method of claim 19, wherein the fitting determines an estimate for an average magnitude parameter value for each of the locations, and the determining information about the test object comprises determining a fringe-free image of the test object based on the estimates for the average magnitude parameter values.

21. The method of claim 20, wherein the fitting further provides surface height information for the test object, and wherein the information about test object comprises the fringe-free image and a surface height profile.

22. The method of claim 20, wherein the fitting further provides thickness profile information for a thin film in the test object, and wherein the information about test object comprises the fringe-free image and the thickness profile.

23. The method of claim 2, wherein the test object comprises a first and second interface.

24. The method of claim 23, wherein the first interface is an outer surface of the object and the second interface is beneath the outer surface, wherein the outer surface is an outer surface of a layer of photoresist overlying a substrate and the second interface is defined between the outer surface of the photoresist and the substrate.

25. The method of claim 24, comprising determining a spatial property of the outer surface based on the fitting and modifying a relative position of the object and a photolithography system based on the spatial property.

26. The method of claim 23, wherein the first interface is an outer surface of the object and the method comprises:
prior to the providing the scanning interferometer signal, removing a material from the outer surface of the object;
determining a spatial property of the outer surface of the object based on the fitting; and
removing additional material from the outer surface of the object based on the spatial property.

27. The method of claim 23, wherein the first and second interfaces are interfaces of a liquid crystal cell.

28. The method of claim 23, comprising:
prior to providing the scanning interferometer signal, irradiating the object with a laser to form a scribe line;
determining a spatial property of a portion of the object including the scribe line based on the fitting; and
performing additional scribing of the same object or a different object based on the spatial property.

29. The method of claim 23, comprising:
prior to providing the scanning interferometer signal, forming the first and second interfaces during a solder bump process.

30. The method of claim 2, further comprising controlling the operation of a semiconductor process tool based on the information determined about the test object at each location.

31. The method of claim 2, further comprising controlling a semiconductor process based on the information determined about the test object at each location.

32. An apparatus comprising:
a scanning interferometer configured to provide a scanning interferometry signal for each of multiple locations of a test object; and
an electronic processor configured to analyze the interferometry signals, the electronic processor configured to fit a model function of the scanning interferometry signal produced by the scanning interferometer to the scanning interferometry signal corresponding to each of one or more of the locations of the test object, for each of a series of shifts in scan position between the model function and the respective scanning interferometry signal, by varying one or more parameter values parametrizing the model function, and determine information about the test object based on the fit.

33. The apparatus of claim 32, wherein the electronic processor is configured to fit the model function to the interferometry signal corresponding to each of multiple locations of the test object.

34. The apparatus of claim 32, wherein the parameter values comprise a phase value, an average magnitude value, and an offset value.

35. The apparatus of claim 33, wherein the model function is expressible as comprising an intensity value for each of a series of local scan positions, and wherein the fitting comprises fitting the model function to each of the interferometry signals with the model function centered on each of the global scan positions corresponding to the series of shifts in scan position between the model function and the respective scanning interferometry signal by varying the parameter values.

36. The apparatus of claim 35, wherein, for each of the locations of the test object, the fitting comprises determining which of the series of shifts in scan positions between the model function and the respective scanning interferometry signal produces an optimum fit.

37. The apparatus of claim 36, wherein the determining information comprises determining a surface height profile for the test object based on the shift in scan position corresponding to the optimum fit for each of the locations.

38. The apparatus of claim 36, wherein the test object comprises a thin film, and wherein the determining information comprises determining a thickness profile for the thin film based on the shift in scan position corresponding to the optimum fit for each of the locations.

39. The apparatus of claim 36, wherein the determining which of the series of shifts in scan positions produces the optimum fit comprises comparing the model function and the respective interferometry signal to determine the degree of similarity between the model function and the respective interferometry signal.

40. The apparatus of claim 39, wherein determining which of the series of shifts in scan positions produces the optimum fit comprises calculating a metric indicative of the degree of similarity between the model function and the respective interferometry signal.

41. The apparatus of claim 40, wherein determining which of the series of shifts in scan positions produces the optimum fit comprises determining a shift in scan position for which the corresponding metric indicates a high degree of similarity between the model function and the respective interferometry signal.

42. The apparatus of claim 35,
wherein the test object comprises a thin film;
wherein the fitting comprises, for each of the locations, determining a first shift of the series of shifts of scan position which corresponds to a first optimal fit and determining a second shift of the series of shifts of scan position which corresponds to a second optimal fit; and
wherein the determining information comprises determining a thickness profile for the thin film based on the first and second shifts in scan position for each of the locations.

43. An apparatus comprising a computer readable medium storing a program configured to cause a processor to fit a model function of a scanning interferometry signal produced by a scanning interferometer to a scanning interferometry signal corresponding to each of one or more of locations of the test object measured by the scanning interferometer, for each of a series of shifts in scan position between the model function and the respective scanning interferometry signal, by varying one or more parameter values parametrizing the model function, determine information about the test object based on the fit.

44. An apparatus comprising:
a means for providing an interferometry signal for each of multiple locations of a test object; and
a means for processing configured to analyze the interferometry signals, the means for processing configured to fit a model function of the interferometry signal produced by the means for providing to the interferometry signal corresponding to each of one or more of the locations of the test object, for each of a series of shifts in scan position between the model function and the respective interferometry signal, by varying one or more parameter values parametrizing the model function, and determine information about the test object based on the fit.

45. The method of claim 1, further comprising: outputting information related to the determined information about the test object.

46. The apparatus of claim 44, wherein the program is further configured to cause the processor to output information related to the determined information about the test object.

* * * * *